(12) United States Patent
Sanders et al.

(10) Patent No.: US 8,753,637 B2
(45) Date of Patent: *Jun. 17, 2014

(54) BINDING PARTNERS FOR THE THYROTROPIN RECEPTOR AND USES THEREOF

(75) Inventors: Jane Sanders, St. Mellons (GB); Jadwiga Furmaniak, Thornhill (GB); Bernard Rees Smith, Old St. Mellons (GB)

(73) Assignee: RSR Limited, Pentwyn, Cardiff (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/339,111

(22) Filed: Dec. 28, 2011

(65) Prior Publication Data

US 2012/0276117 A1 Nov. 1, 2012

Related U.S. Application Data

(62) Division of application No. 10/537,280, filed as application No. PCT/GB03/05171 on Nov. 28, 2003, now Pat. No. 8,110,664.

(30) Foreign Application Priority Data

Nov. 29, 2002 (GB) .................................. 0227964.4
Jan. 29, 2003 (GB) .................................. 0302140.9
Jun. 27, 2003 (GB) .................................. 0315147.9

(51) Int. Cl.
*A61K 39/395* (2006.01)
*C07H 21/04* (2006.01)
*C07K 16/00* (2006.01)
*C12P 21/08* (2006.01)

(52) U.S. Cl.
USPC ................ 424/172.1; 530/388.22; 530/389.1; 536/23.53

(58) Field of Classification Search
None
See application file for complete search history.

(56) References Cited

U.S. PATENT DOCUMENTS

| | | | |
|---|---|---|---|
| 5,565,332 A | 10/1996 | Hoogenboom et al. | |
| 5,840,853 A | 11/1998 | Segre et al. | |
| 6,537,760 B1 * | 3/2003 | Bergmann et al. | 435/7.1 |

FOREIGN PATENT DOCUMENTS

| | | |
|---|---|---|
| EP | 0719858 A2 | 7/1996 |
| EP | 1078986 A2 | 2/2001 |
| WO | 91/09137 | 6/1991 |
| WO | WO 9109137 A1 * | 6/1991 |
| WO | WO 9826294 A1 * | 6/1998 |
| WO | 9964865 | 12/1999 |
| WO | 03/018632 A2 | 3/2003 |

OTHER PUBLICATIONS

Oda et al., (J Mol Endocrinology. Apr. 1998; 20(2):233-44) (cited on Applicant's IDS filed Feb. 15, 2012).*
Akamizu et al., (Endocrinology. Apr. 1999;140(4):1594-1601) (cited on Applicant's IDS filed Feb. 15, 2012).*
Kohn et al., (J Clin Endo and Metab. 1997;82(12):3998-4009) (cited on Applicant's IDS filed Feb. 15, 2012).*

(Continued)

*Primary Examiner* — Cherie M Stanfield
(74) *Attorney, Agent, or Firm* — Larson & Anderson, LLC

(57) ABSTRACT

A binding partner for the TSH receptor, which binding partner comprises, or is derived from, a human monoclonal or recombinant antibody, or one or more fragments thereof, reactive with the TSH receptor, uses thereof, methods of diagnosis and therapy employing the same, and anti-idiotypic antibodies thereto.

22 Claims, 10 Drawing Sheets

(56) References Cited

OTHER PUBLICATIONS

UniProt, Accession No. P16473 (sequence version 1), Aug. 1, 1990.
Akamizu, T. et al., Characterization of Recombinant Monoclonal Antithyrotropin Receptor Antibodies (TSHRAbs) Derived from Lymphocytes of Patients with Graves' Disease: Epitope and Binding Study of Two Stimulatory TSHRAbs*, Endocrinology, 1999, pp. 1594-1601, vol. 140, No. 4.
Akamizu, T. et al., Molecular Analysis of Stimulatory Anti-Thyrotropin Receptor Antibodies (TSAbs) Involved in Graves' Disease, Journal of Immunology, 1996, pp. 3148-3152, vol. 157.
Chazenbalk, G. D. et al, Thyroid-stimulating autoantibodies in Graves disease preferentially recognize the free A subunit, not the thyrotropin holoreceptor, Journal of Clinical Investigation, 2002, pp. 209-217, vol. 110, No. 2.
Cundiff, J. G. et al., Studies Using Recombinant Fragments of Human TSH Receptor Reveal Apparent Diversity in the Binding Specificities of Antibodies That Block TSH Binding to Its Receptor or Stimulate Thyroid Hormone Production, the Journal of Clinical Endocrinology & Metabolism, 2001, pp. 4254-4260.
Kohn, L. D. et al., Characterization of Monoclonal Thyroid-Stimulating and Thyrotropin Binding-Inhibiting Autoantibodies from a Hashimotos Patient Whose Children Had Intrauterine and Neonatal Thyroid Disease, Journal of Clinical Endocrinology and Metabolism, 1997, pp. 3998-4009, vol. 82, No. 12.
Bulow Pedersen, I. et al., TSH-receptor antibody measurement for differentiation of hyperthyroidism into Graves' disease and multinodular toxic goitre: a comparison of two competitive binding assays, Clinical Endocrinology, 2001, pp. 381-390, vol. 55.
Sanders, J. et al., The Interaction of TSH Receptor Autoantibodies with 125 I-Labelled TSH Receptor, The Journal of Clinical Endocrinology & Metabolism, 1999, pp. 3797-3802, vol. 84, No. 10.
Shepherd, P.S. et al., Identification of an important thyrotrophin binding site on the human thyrotrophin receptor using monoclonal antibodies, Molecular and Cellular Endocrinology, 1999, pp. 197-206, vol. 149.
Van Der Heijden, J. H. W. et al., Limitations of the semisynthetic library approach for obtaining human monoclonal autoantibodies to the thyrotropin receptor of Graves' disease, Clin Exp Immunol, 1999, pp. 205-212, vol. 118.
Valente, L. A. et al., Monoclonal antibodies to the thyrotropin receptor: Stimulating and blocking antibodies derived from the lymphocytes of patients with Graves disease, Proc Natl Acad. Sci USA, 1982, pp. 6680-6684, vol. 79.
Yoshida, T. et al, Monoclonal Antibodies to the Thyrotropin Receptor Bind to a 56-kDa Subunit of the Thyrotropin Receptor and Show Heterogeneous Bioactivities*, The Journal of Biological Chemistry, 1988, pp. 16341-16347, vol. 263, No. 31.
Zhong, X. et al., Cloning and sequence analysis of light variable region gene of anti-human retinoblastoma monoclonal antibody, Yan Ke Xue Bao, 2002, pp. 185-189, vol. 18, No. 3 (Abstract).
Saper et al., Magic Peptides, Magic Antibodies: Guidelines for Appropriate Controls for Immunohistochemistry, The Journal of Comparative Neurology, 2003, pp. 161-163, vol. 465.
NCBI Accession No. M32215, Misrahi, M. et al., Cloning, sequencing and expression of human TSH receptor, 1995.
Costagliola, et al., Monoclonal Antibodies with Thyroid Stimulating Activity, at Last, Thyroid, 2002, pp. 1039-1041, vol. 12, No. 12.
Ando, T. et al., Monoclonal antibodies to the thyrotropin receptor, Clin Devel Immunol, 2005, pp. 137-143, vol. 12, No. 2.
Ando, T. et al., A monoclonal thyroid-stimulating antibody, the Journal of Clinical Investigation, 2002, pp. 1667-1674, vol. 110, No. 11.
Sanders, J. et al., Thyroid-Stimulating Monoclonal Antibodies, Thyroid, 2002, pp. 1043-1050, vol. 12, No. 12.
Rapoport, B. et al., The Thyrotropin (TSH) Receptor: Interaction with TSH and Autoantibodies, Endocrine Reviews, 1998, (downloaded from edrv.endojournals.org by on Apr. 18, 2008), pp. 673 and 698, vol. 19, No. 8.
Chen, S. et al., Analysis of Autoantibody Epitopes on Steroid 21-Hydroxylase Using a Panel of Monoclonal Antibodies, Journal of Clinical Endocrinology and Metabolism, 1998, pp. 2977-2986, vol. 83, No. 8.
Collet, T.A. et al., A binary plasmid system for shuffling combinatorial antibody libraries, Proc. Natl. Acad. Sci. USA, 1992, pp. 10026-10030, vol. 89.
Latif, R. et al., Oligomerization of the Human Thyrotropin Receptor, The Journal of Biological Chemistry, 2001, pp. 45217-45224, vol. 276, No. 48.
Myers, M. A. et al., Conformational Epitopes on the Diabetes Autoantigen GAD65 Identified by Peptide Phage Display and Molecular Modeling, The Journal of Immunology, 2000, pp. 3830-3838, vol. 165.
Morris, J. C. et al., Structure-Function Studies of the Human Thyrotropin Receptor, the Journal of Biological Chemistry, 1993, pp. 10900-10905, vol. 268, No. 15.
Bolton, J. et al., Measurement of Thyroid-stimlating Hormone Receptor Autoantibodies by ELISA, Clinical Chemistry, 1999, pp. 2285-2287, vol. 45, No. 12.
Oda, Y. et al., Binding characteristics of antibodies to the TSH receptor, Journal of Molecular Endocrinology, 1998, pp. 233-244, vol. 20.
Prentice, L. et al., Thyrotropin (ISH) Receptor Autoantibodies Do Not Appear to Bind to the TSH Receptor Produced in an in Vitro Transcription/Translation System, Journal of Clinical Endocrinology and Metabolism, 1997, pp. 1288-1292, vol. 82, No. 4.
Sanger, F. et al., DNA sequencing with chain-terminating inhibitors, Proceedings of the National Academy of Sciences of the USA, 1977, pp. 5463-5467, vol. 74, No. 12.

* cited by examiner caaatgcagctggtgcagtctggagcagaggtgaaaaagcccggggagtc       50
<u>PCR primer</u> tctgaagatctcctgtagggttctggatacaggtttacc<span style="border:1px solid">agctactgga</span>       100
                                          CDR I <span style="border:1px solid">tcaac</span>tgggtgcgccagctgcccgggaaaggcctagagtggatgggc<span style="border:1px solid">agg</span>       150
                                                    CDR II <span style="border:1px solid">attgatcctactgactcttataccaagtacagtccatccttcaaaggc</span>ca       200 cgtcaccgtctcagctgacaagtccatcaacactgcctacctgcagtgga       250 gcagcctgaaggcctcggacaccggcatgtattactgtgcgagg<span style="border:1px solid">ctgaa</span>       300
                                               CDR III <span style="border:1px solid">ccggggctatagcagcacctggtccgtaaat</span>tggggccagggaaccctggt       350
<u>constant region</u>
caccgtctcctcagcctccaccaagggcccatcggtcttcccc       394

SEQ ID NO: 14

Fig. 4

QVQLVQSGAEVKKPGESLKISCRGSGYRFT<span style="border:1px solid">SYWIN</span>WVRQLPGKGLEWMG<span style="border:1px solid">R</span>       50
                                 CDR I <span style="border:1px solid">IDPTDSYTNYSPSFKG</span>HVTVSADKSINTAYLQWSSLKASDTGMYYCAR<span style="border:1px solid">LE</span>       100
CDR II <span style="border:1px solid">PGYSSTWSVN</span>WGQGTLVTVSSASTKGPSVFP       131
CDR III                   constant region

SEQ ID NO: 5

Fig. 5

```
ctgcctgtgctgactcagccaccctcggtgtctggagcccccaggcagag    50
  PCR primer
ggtcaccatctcctgtTctggaaacagctccaacatcggaaataatgctg    100
                                CDR I
taaacTggtaccagcagctcccaggaaaggctcccaaactcctcatttat    150 tatgatgatcaactgccctcaggggtctctgaccgattctctggctccag    200
  CDR II
gtctggcacctccgcctccctggccatccgtgggctccagtctgaggatg    250 aggctgattattactgtAcatcatgggatgacagtctggatagtcaactg    300
                                CDR III
ttcggcggagggaccaggctgaccgtcctaggt                    333
```

Fig. 6

SEQ ID NO: 15

```
LTVLTQPPSVSGAPRQRVTISCSGNSSNIGNNAVNWYQQLPGKAPKLLIY    50
                      CDR I

YDDQLPSGVSDRFSGSRSGTSASLAIRGLQSEDEADYYCFSWDDSLDSQL    100
 CDR II                                 CDR III

FGGGTRLTVLG                                          111
```

SEQ ID NO: 6

Fig. 7

```
gacgtccagatccagcagcctgggactgagcttgtgaagcctggggcttc    50
    PCR primer
agtgagactgtcctgcaaggcttctggctacaccttcacc acctactgga    100
                                          CDR I
tgcac tgggtgaagcagaggcctggacaaggccttgagtggatcgga gag    150
                                                 CDR II
attgatccttctgatagttatactaactataatcaaaagttcaagggc aa    200 ggccacattgactgtagacaaatcctccagcacagcctacatgcacctca    250
                                              CDR III
gcagcctgacatctgaggactctgcggtctattactgttcaaga aactac    300 ggtagtggctactactttgactac tggggccaaggcaccactctcacagt    350 ctcctcag ccaaaacaacacccc                              373
         constant region
                                        SEQ ID NO: 33
```

Fig. 9

```
DVQIQQPGTELVKPGASVRLSCKASGYTFT TYWMH WVKQRPGQGLEWIG E    50
PCR primer                      CDR I
IDPSDSYTNYNQKFKG KATLTVDKSSSTAYMHLSSLTSEDSAVYYCSR NY    100
 CDR II                                              CDR III
GSGYYFDY WGQGTTLTVSS AKTTP                              124
                     constant region
                                        SEQ ID NO: 23
```

Fig. 10

```
ggcgttgagatgacacagtcgccagcaatcatgtctgcatctccagggga        50
    PCR primer gaaggtcaccatgacctgcagtgccagctcaagtgtaagttacatgcact        100
                       CDR I ggtaccagcagaagtcaggcacctcccccaaaagatggatttatgacaca        150
                                                CDR II tccaaactggcttctggagtccctgctcgcttcagtggcagtgggtctgg        200
CDR II gacctcttactctctcacaatcagcagcatggagactgaagatgctgcca        250

CDR III
cttattactgccagcagtggagtagtaacccgtggacgttcggtggaggc        300 accaaactggaaatcaaacggctgatgctgc                           331
                constant region
```

SEQ ID NO: 38

Fig. 11

```
GVEMTQSPAIMSASPGEKVTMTCSASSSVSYMHWYQQKSGTSPKRWIYDT         50
PCR primer           CDR I SKLASGVPARFSGSGSGTSYSLTISSMETEDAATYYCQQWSSNPWTFGGG        100
CDR II                                CDR III TKLEIKRLML                                                110
    constant region
```

SEQ ID NO: 28

Fig. 12

SEQUENCE LISTING

```
<160> NUMBER OF SEQ ID NOS: 38

<210> SEQ ID NO 1
<211> LENGTH: 121
<212> TYPE: PRT
<213> ORGANISM: Homo sapiens

<400> SEQUENCE: 1

Gln Val Gln Leu Val Gln Ser Gly Ala Glu Val Lys Lys Pro Gly Glu
1               5                   10                  15

Ser Leu Lys Ile Ser Cys Arg Gly Ser Gly Tyr Arg Phe Thr Ser Tyr
            20                  25                  30

Trp Ile Asn Trp Val Arg Gln Leu Pro Gly Lys Gly Leu Glu Trp Met
        35                  40                  45

Gly Arg Ile Asp Pro Thr Asp Ser Tyr Thr Asn Tyr Ser Pro Ser Phe
    50                  55                  60

Lys Gly His Val Thr Val Ser Ala Asp Lys Ser Ile Asn Thr Ala Tyr
65                  70                  75                  80

Leu Gln Trp Ser Ser Leu Lys Ala Ser Asp Thr Gly Met Tyr Tyr Cys
                85                  90                  95

Ala Arg Leu Glu Pro Gly Tyr Ser Ser Thr Trp Ser Val Asn Trp Gly
            100                 105                 110

Gln Gly Thr Leu Val Thr Val Ser Ser
        115                 120

<210> SEQ ID NO 2
<211> LENGTH: 5
<212> TYPE: PRT
<213> ORGANISM: Homo sapiens
```

```
<400> SEQUENCE: 2

Ser Tyr Trp Ile Asn
1               5

<210> SEQ ID NO 3
<211> LENGTH: 17
<212> TYPE: PRT
<213> ORGANISM: Homo sapiens

<400> SEQUENCE: 3

Arg Ile Asp Pro Thr Asp Ser Tyr Thr Asn Tyr Ser Pro Ser Phe Lys
1               5                   10                  15

Gly

<210> SEQ ID NO 4
<211> LENGTH: 12
<212> TYPE: PRT
<213> ORGANISM: Homo sapiens

<400> SEQUENCE: 4

Leu Glu Pro Gly Tyr Ser Ser Thr Trp Ser Val Asn
1               5                   10

<210> SEQ ID NO 5
<211> LENGTH: 131
<212> TYPE: PRT
<213> ORGANISM: Homo sapiens

<400> SEQUENCE: 5

Gln Val Gln Leu Val Gln Ser Gly Ala Glu Val Lys Lys Pro Gly Glu
1               5                   10                  15

Ser Leu Lys Ile Ser Cys Arg Gly Ser Gly Tyr Arg Phe Thr Ser Tyr
                20                  25                  30

Trp Ile Asn Trp Val Arg Gln Leu Pro Gly Lys Gly Leu Glu Trp Met
            35                  40                  45

Gly Arg Ile Asp Pro Thr Asp Ser Tyr Thr Asn Tyr Ser Pro Ser Phe
        50                  55                  60

Lys Gly His Val Thr Val Ser Ala Asp Lys Ser Ile Asn Thr Ala Tyr
65                  70                  75                  80

Leu Gln Trp Ser Ser Leu Lys Ala Ser Asp Thr Gly Met Tyr Tyr Cys
                85                  90                  95

Ala Arg Leu Glu Pro Gly Tyr Ser Ser Thr Trp Ser Val Asn Trp Gly
            100                 105                 110

Gln Gly Thr Leu Val Thr Val Ser Ser Ala Ser Thr Lys Gly Pro Ser
        115                 120                 125

Val Phe Pro
    130

<210> SEQ ID NO 6
<211> LENGTH: 111
<212> TYPE: PRT
<213> ORGANISM: Homo sapiens

<400> SEQUENCE: 6

Leu Thr Val Leu Thr Gln Pro Pro Ser Val Ser Gly Ala Pro Arg Gln
1               5                   10                  15

Arg Val Thr Ile Ser Cys Ser Gly Asn Ser Ser Asn Ile Gly Asn Asn
                20                  25                  30

Ala Val Asn Trp Tyr Gln Gln Leu Pro Gly Lys Ala Pro Lys Leu Leu
            35                  40                  45
```

```
Ile Tyr Tyr Asp Asp Gln Leu Pro Ser Gly Val Ser Asp Arg Phe Ser
        50                  55                  60

Gly Ser Arg Ser Gly Thr Ser Ala Ser Leu Ala Ile Arg Gly Leu Gln
 65                  70                  75                  80

Ser Glu Asp Glu Ala Asp Tyr Tyr Cys Thr Ser Trp Asp Ser Leu
                85                  90                  95

Asp Ser Gln Leu Phe Gly Gly Gly Thr Arg Leu Thr Val Leu Gly
            100                 105                 110
```

<210> SEQ ID NO 7
<211> LENGTH: 13
<212> TYPE: PRT
<213> ORGANISM: Homo sapiens

<400> SEQUENCE: 7

```
Ser Gly Asn Ser Ser Asn Ile Gly Asn Asn Ala Val Asn
 1               5                  10
```

<210> SEQ ID NO 8
<211> LENGTH: 7
<212> TYPE: PRT
<213> ORGANISM: Homo sapiens

<400> SEQUENCE: 8

```
Tyr Asp Asp Gln Leu Pro Ser
 1               5
```

<210> SEQ ID NO 9
<211> LENGTH: 11
<212> TYPE: PRT
<213> ORGANISM: Homo sapiens

<400> SEQUENCE: 9

```
Thr Ser Trp Asp Asp Ser Leu Asp Ser Gln Leu
 1               5                  10
```

<210> SEQ ID NO 10
<211> LENGTH: 363
<212> TYPE: DNA
<213> ORGANISM: Homo sapiens

<400> SEQUENCE: 10

```
caaatgcagc tggtgcagtc tggagcagag gtgaaaaagc ccggggagtc tctgaagatc    60
tcctgtaggg gttctggata caggtttacc agctactgga tcaactgggt gcgccagctg   120
cccgggaaag gcctagagtg gatgggcagg attgatccta ctgactctta taccaactac   180
agtccatcct tcaaaggcca cgtcaccgtc tcagctgaca gtccatcaa cactgcctac   240
ctgcagtgga gcagcctgaa ggcctcggac accggcatgt attactgtgc gaggctcgaa   300
ccgggctata gcagcacctg gtccgtaaat tggggccagg gaaccctggt caccgtctcc   360
tca                                                                 363
```

<210> SEQ ID NO 11
<211> LENGTH: 15
<212> TYPE: DNA
<213> ORGANISM: Homo sapiens

<400> SEQUENCE: 11

```
agctactgga tcaac                                                    15
```

<210> SEQ ID NO 12

```
<211> LENGTH: 51
<212> TYPE: DNA
<213> ORGANISM: Homo sapiens

<400> SEQUENCE: 12
aggattgatc ctactgactc ttataccaac tacagtccat ccttcaaagg c            51

<210> SEQ ID NO 13
<211> LENGTH: 36
<212> TYPE: DNA
<213> ORGANISM: Homo sapiens

<400> SEQUENCE: 13
ctcgaaccgg gctatagcag cacctggtcc gtaaat                             36

<210> SEQ ID NO 14
<211> LENGTH: 394
<212> TYPE: DNA
<213> ORGANISM: Homo sapiens

<400> SEQUENCE: 14
caaatgcagc tggtgcagtc tggagcagag gtgaaaaagc ccggggagtc tctgaagatc   60
tcctgtaggg gttctggata caggtttacc agctactgga tcaactgggt gcgccagctg  120
cccgggaaag gcctagagtg gatgggcagg attgatccta ctgactctta taccaactac  180
agtccatcct tcaaaggcca cgtcaccgtc tcagctgaca agtccatcaa cactgcctac  240
ctgcagtgga gcagcctgaa ggcctcggac accggcatgt attactgtgc gaggctcgaa  300
ccgggctata gcagcacctg gtccgtaaat tggggccagg gaaccctggt caccgtctcc  360
tcagcctcca caagggccc atcggtcttc cccc                               394

<210> SEQ ID NO 15
<211> LENGTH: 333
<212> TYPE: DNA
<213> ORGANISM: Homo sapiens

<400> SEQUENCE: 15
ctgcctgtgc tgactcagcc accctcggtg tctggagccc ccaggcagag ggtcaccatc   60
tcctgttctg gaaacagctc caacatcgga aataatgctg taaactggta ccagcagctc  120
ccaggaaagg ctcccaaaac tctcatttat tatgatgatc aactgccctc agggtctct   180 gaccgattct ctggctccag gtctggcacc tccgcctccc tggccatccg tgggctccag  240
tctgaggatg aggctgatta ttactgtaca tcatgggatg acagcctgga tagtcaactg  300
ttcggcggag ggaccaggct gaccgtccta ggt                               333

<210> SEQ ID NO 16
<211> LENGTH: 39
<212> TYPE: DNA
<213> ORGANISM: Homo sapiens

<400> SEQUENCE: 16
tctggaaaca gctccaacat cggaaataat gctgtaaac                          39

<210> SEQ ID NO 17
<211> LENGTH: 21
<212> TYPE: DNA
<213> ORGANISM: Homo sapiens

<400> SEQUENCE: 17
tatgatgatc aactgccctc a                                             21
```

```
<210> SEQ ID NO 18
<211> LENGTH: 33
<212> TYPE: DNA
<213> ORGANISM: Homo sapiens

<400> SEQUENCE: 18
acatcatggg atgacagcct ggatagtcaa ctg                                    33

<210> SEQ ID NO 19
<211> LENGTH: 119
<212> TYPE: PRT
<213> ORGANISM: Mus sp.

<400> SEQUENCE: 19

Asp Val Gln Ile Gln Gln Pro Gly Thr Glu Leu Val Lys Pro Gly Ala
1               5                   10                  15

Ser Val Arg Leu Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ser Arg Asn Tyr Gly Ser Gly Tyr Tyr Phe Asp Tyr Trp Gly Gln Gly
            100                 105                 110

Thr Thr Leu Thr Val Ser Ser
        115

<210> SEQ ID NO 20
<211> LENGTH: 5
<212> TYPE: PRT
<213> ORGANISM: Mus sp.

<400> SEQUENCE: 20

Thr Tyr Trp Met His
1               5

<210> SEQ ID NO 21
<211> LENGTH: 17
<212> TYPE: PRT
<213> ORGANISM: Mus sp.

<400> SEQUENCE: 21

Glu Ile Asp Pro Ser Asp Ser Tyr Thr Asn Tyr Asn Gln Lys Phe Lys
1               5                   10                  15

Gly

<210> SEQ ID NO 22
<211> LENGTH: 10
<212> TYPE: PRT
<213> ORGANISM: Mus sp.

<400> SEQUENCE: 22

Asn Tyr Gly Ser Gly Tyr Tyr Phe Asp Tyr
1               5                   10

<210> SEQ ID NO 23
<211> LENGTH: 124
```

```
<212> TYPE: PRT
<213> ORGANISM: Mus sp.

<400> SEQUENCE: 23

Asp Val Gln Ile Gln Gln Pro Gly Thr Glu Leu Val Lys Pro Gly Ala
1               5                   10                  15

Ser Val Arg Leu Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Thr Ala Tyr
65                  70                  75                  80

Met His Leu Ser Ser Leu Thr Ser Glu Asp Ser Ala Val Tyr Tyr Cys
            85                  90                  95

Ser Arg Asn Tyr Gly Ser Gly Tyr Tyr Phe Asp Tyr Trp Gly Gln Gly
            100                 105                 110

Thr Thr Leu Thr Val Ser Ser Ala Lys Thr Thr Pro
            115                 120

<210> SEQ ID NO 24
<211> LENGTH: 106
<212> TYPE: PRT
<213> ORGANISM: Mus sp.

<400> SEQUENCE: 24

Gly Val Glu Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Thr Glu
65                  70                  75                  80

Asp Ala Ala Thr Tyr Tyr Cys Gln Gln Trp Ser Ser Asn Pro Trp Thr
            85                  90                  95

Phe Gly Gly Gly Thr Lys Leu Glu Ile Lys
            100                 105

<210> SEQ ID NO 25
<211> LENGTH: 10
<212> TYPE: PRT
<213> ORGANISM: Mus sp.

<400> SEQUENCE: 25

Ser Ala Ser Ser Ser Val Ser Tyr Met His
1               5                   10

<210> SEQ ID NO 26
<211> LENGTH: 7
<212> TYPE: PRT
<213> ORGANISM: Mus sp.

<400> SEQUENCE: 26

Asp Thr Ser Lys Leu Ala Ser
1               5
```

<210> SEQ ID NO 27
<211> LENGTH: 9
<212> TYPE: PRT
<213> ORGANISM: Mus sp.

<400> SEQUENCE: 27

Gln Gln Trp Ser Ser Asn Pro Trp Thr
1               5

<210> SEQ ID NO 28
<211> LENGTH: 110
<212> TYPE: PRT
<213> ORGANISM: Mus sp.

<400> SEQUENCE: 28

Gly Val Glu Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Thr Glu
65                  70                  75                  80

Asp Ala Ala Thr Tyr Tyr Cys Gln Gln Trp Ser Ser Asn Pro Trp Thr
                85                  90                  95

Phe Gly Gly Gly Thr Lys Leu Glu Ile Lys Arg Leu Met Leu
            100                 105                 110

<210> SEQ ID NO 29
<211> LENGTH: 357
<212> TYPE: DNA
<213> ORGANISM: Mus sp.

<400> SEQUENCE: 29
gacgtccaga tccagcagcc tgggactgag cttgtgaagc ctggggcttc agtgagactg      60
tcctgcaagg cttctggcta caccttcacc acctactgga tgcactgggt gaagcagagg     120
cctggacaag gccttgagtg gatcggagag attgatcctt ctgatagtta tactaactat     180
aatcaaaagt tcaagggcaa ggccacattg actgtagaca atcctccag cacagcctac      240 atgcacctca gcagcctgac atctgaggac tctgcggtct attactgttc aagaaactac     300
ggtagtggct actactttga ctactggggc caaggcacca ctctcacagt ctcctca       357

<210> SEQ ID NO 30
<211> LENGTH: 15
<212> TYPE: DNA
<213> ORGANISM: Mus sp.

<400> SEQUENCE: 30
acctactgga tgcac                                                       15

```
<210> SEQ ID NO 31
<211> LENGTH: 51
<212> TYPE: DNA
<213> ORGANISM: Mus sp.

<400> SEQUENCE: 31
gagattgatc cttctgatag ttatactaac tataatcaaa agttcaaggg c            51

<210> SEQ ID NO 32
<211> LENGTH: 30
<212> TYPE: DNA
<213> ORGANISM: Mus sp.

<400> SEQUENCE: 32
aactacggta gtggctacta ctttgactac                                    30

<210> SEQ ID NO 33
<211> LENGTH: 373
<212> TYPE: DNA
<213> ORGANISM: Mus sp.

<400> SEQUENCE: 33
gacgtccaga tccagcagcc tgggactgag cttgtgaagc ctggggcttc agtgagactg   60
tcctgcaagg cttctggcta caccttcacc acctactgga tgcactgggt gaagcagagg  120
cctggacaag gccttgagtg gatcggagag attgatcctt ctgatagtta tactaactat  180
aatcaaaagt tcaagggcaa ggccacattg actgtagaca atcctccag cacagcctac   240 atgcacctca gcagcctgac atctgaggac tctgcggtct attactgttc aagaaactac  300
ggtagtggct actactttga ctactggggc caaggcacca ctctcacagt ctcctcagcc  360
aaaacaacac ccc                                                     373

<210> SEQ ID NO 34
<211> LENGTH: 318
<212> TYPE: DNA
<213> ORGANISM: Mus sp.

<400> SEQUENCE: 34
ggcgttgaga tgacacagtc gccagcaatc atgtctgcat ctccagggga aaggtcacc    60 atgacctgca gtgccagctc aagtgtaagt tacatgcact ggtaccagca gaagtcaggc  120
acctccccca aaagatggat ttatgacaca tccaaactgg cttctggagt ccctgctcgc  180
ttcagtggca gtgggtctgg gacctcttac tctctcacaa tcagcagcat ggagactgaa  240
gatgctgcca cttattactg ccagcagtgg agtagtaacc cgtggacgtt cggtggaggc  300
accaaactgg aaatcaaa                                                318

<210> SEQ ID NO 35
<211> LENGTH: 30
<212> TYPE: DNA
<213> ORGANISM: Mus sp.

<400> SEQUENCE: 35
agtgccagct caagtgtaag ttacatgcac                                    30

<210> SEQ ID NO 36
<211> LENGTH: 21
<212> TYPE: DNA
<213> ORGANISM: Mus sp.

<400> SEQUENCE: 36
gacacatcca aactggcttc t                                             21
```

```
<210> SEQ ID NO 37
<211> LENGTH: 27
<212> TYPE: DNA
<213> ORGANISM: Mus sp.

<400> SEQUENCE: 37
cagcagtgga gtagtaaccc gtggacg                                          27

<210> SEQ ID NO 38
<211> LENGTH: 331
<212> TYPE: DNA
<213> ORGANISM: Mus sp.

<400> SEQUENCE: 38
ggcgttgaga tgacacagtc gccagcaatc atgtctgcat ctccagggga gaaggtcacc      60
atgacctgca gtgccagctc aagtgtaagt tacatgcact ggtaccagca gaagtcaggc     120
acctccccca aaagatggat ttatgacaca tccaaactgg cttctggagt ccctgctcgc     180
ttcagtggca gtgggtctgg gacctcttac tctctcacaa tcagcagcat ggagactgaa     240
gatgctgcca cttattactg ccagcagtgg agtagtaacc cgtggacgtt cggtggaggc     300
accaaactgg aaatcaaacg gctgatgctg c                                    331
```

BINDING PARTNERS FOR THE THYROTROPIN RECEPTOR AND USES THEREOF

BACKGROUND OF THE INVENTION

The present invention is concerned with binding partners (such as monoclonal or recombinant antibodies) for the thyrotropin receptor (TSH receptor or TSHR) and uses thereof.

Thyrotropin or thyroid stimulating hormone (TSH) is a pituitary hormone which plays a key role in regulating the function of the thyroid. Its release is stimulated by the hormone TRH formed in the hypothalamus and TSH controls the formation and release of the important, thyroid hormones thyroxine (T4) and tri-iodothyronine (T3). On the basis of a feedback mechanism, the thyroid hormone content of serum controls the release of TSH. The formation of T3 and T4 by thyroid cells is stimulated by TSH by a procedure in which the TSH released by the pituitary binds to the TSH receptor of the thyroid cell membrane.

In Graves' disease (a common autoimmune disorder) TSH receptor antibodies (TRAb) are formed and these autoantibodies bind to the TSH receptor in such a way as to mimic the actions of TSH, stimulating the thyroid gland to produce high levels of thyroid hormones. These autoantibodies are described as having stimulating activity. In some patients, autoantibodies bind to the TSH receptor but do not stimulate thyroid hormone production and are described as having blocking activity. (J Sanders, Y Oda, S-A Roberts, M Maruyama, J Furmaniak, B Rees Smith; "Understanding the thyrotrophin receptor function-structure relationship" Balliere's Clinical Endocrinology and Metabolism; Ed T F Davies 1997; 11 (3): 451-479; pub Ballière Tindall, London).

Measurements of TSH receptor antibodies are important in the diagnosis and management of Graves' disease and other thyroid disorders. Currently three types of assay are used to measure TSH receptor antibodies:
(a) competitive binding assays which measure the ability of TSH receptor antibodies to inhibit the binding of TSH to preparations of TSH receptor;
(b) bioassays which measure the ability of TSH receptor antibodies to stimulate cells expressing the TSH receptor in culture; and
(c) immunoprecipitation of TSH receptor preparations with TSH receptor antibodies.

Measurement of TSH receptor antibodies using such assays are described in references:—
J Sanders, Y Oda, S-A Roberts, M Maruyama, J Furmaniak, B Rees Smith; "Understanding the thyrotrophin receptor function-structure relationship" Balliere's Clinical Endocrinology and Metabolism; Ed T F Davies 1997; 11 (3): 451-479; pub Ballière Tindall, London.
Sanders, Y Oda, S Roberts, A Kiddie, T Richards, J Bolton, V McGrath, S Walters, D Jaskolski, J Furmaniak, B Rees Smith; "The interaction of TSH receptor autoantibodies with $^{125}$I-labelled TSH receptor"; Journal of Clinical Endocrinology and Metabolism 1999; 84 (10): 3797-3802.

It has been recognised for many years that human monoclonal antibodies to the TSH receptor derived from patients' lymphocytes would be valuable reagents for understanding the pathogenesis of Graves' disease and for developing new methods of measuring TSH receptor antibodies for example as replacements for TSH in competitive binding assays. Also, as the patient's serum TSH receptor antibodies are usually powerful thyroid stimulators (TSH agonists) stimulating human monoclonal TSH receptor antibodies would be valuable for in vivo applications when tissue containing the TSH receptor (eg thyroid tissue or thyroid cancer tissue) required stimulation. Furthermore, as some patient serum TSH receptor antibodies are powerful TSH antagonists (blocking antibodies) human monoclonal TSH receptor antibodies which are TSH antagonists would be valuable for in vivo applications when the activity of tissue containing the TSH receptor (eg thyroid tissue or thyroid cancer tissue) required inactivation or to be made unresponsive to TSH, TSH receptor antibodies or other stimulators.

It has also been recognised that one of the major advantages of human monoclonal TSH receptor antibodies over TSH in such in vitro and/or in vivo applications would be the relative ease with which antibodies can be manipulated. For example, manipulation of the TSH receptor binding region of the monoclonal antibodies so as to change their characteristics, such as affinity and biological characteristics including their degree of TSH agonist or antagonist activities. Also, monoclonal antibodies will have a much longer half life than TSH in vivo and this may have considerable advantages in certain in vivo applications. Furthermore, the half life of antibodies can be manipulated easily, for example antibody Fab fragments have a much shorter half life than intact IgG. These general properties of TSH receptor antibodies are described in the publications such as B Rees Smith, S M McLachlan, J Furmaniak; "Autoantibodies to the thyrotropin receptor"; Endocrine Reviews 1988; 9: 106-121; B Rees Smith, K J Dorrington, D S Munro; "The thyroid stimulating properties of long-acting thyroid stimulator yG-globulin subunits"; Biochimica et Biophysica Acta 1969; 192: 277-285; K J Dorrington, D S Munro; "The long acting thyroid stimulator"; Clinical Pharmacology and Therapeutics 1966; 7: 788-806.

A still further advantage of human monoclonal TSH receptor antibodies could be in their use to identify and provide new types of TSH receptor antibody binding sites. For example by the generation of antibodies to the regions of the human monoclonal TSH receptor antibodies which bind the TSH receptor. Some of the anti-idiotypic antibodies produced in this way could have potential as new ligands for assays of TSH receptor antibodies, TSH and related compounds. Also they may be effective agents in vivo for regulating the action of TSH receptor antibodies, TSH and related compounds.

Other methods of identifying and providing new types of antibody binding sites using monoclonal antibodies are well known. For example by antibody screening of phage-displayed random peptide libraries as described by J C Scott and G P Smith; "Searching for peptide ligands with an epitope library"; Science 1990; 249 (4967): 386-390 and M A Myers, J M Davies, J C Tong, J Whisstock, M Scealy, I R MacKay, M J Rowley; "Conformational epitopes on the diabetes autoantigen $GAD_{65}$ identified by peptide phage display and molecular modelling"; Journal of Immunology 2000; 165: 3830-3838. Antibody screening of non-peptide compounds and libraries of non-peptide compounds can also be carried out.

New types of TSH receptor antibody binding sites identified and provided using these procedures may also be useful as new ligands in assays for TSH receptor antibodies, TSH and related compounds. Furthermore they may be effective agents in vivo for regulating the action of TSH receptor antibodies, TSH and related compounds.

In view of the potential value of human monoclonal TSH receptor antibodies there have been considerable efforts over many years to produce such antibodies (see for example B Rees Smith, S M McLachlan, J Furmaniak; "Autoantibodies to the thyrotropin receptor"; Endocrine Reviews 1988; 9: 106-121. However, to date these efforts have been unsuccessful (see for example S M McLachlan, B Rapoport; "Monoclonal, human autoantibodies to the TSH receptor—The Holy Grail and why are we looking for it"; Journal of Clinical Endocrinology and Metabolism 1996; 81: 3152-3154 and J H W van der Heijden, T W A de Bruin, K A F M Gludemans, J de Kruif, J P Banga, T Logtenberg; "Limitations of the semi-synthetic library approach for obtaining human monoclonal autoantibodies to the thyrotropin receptor of Graves' disease"; Clinical and Experimental Immunology 1999; 118: 205-212).

SUMMARY OF THE INVENTION

The present provides a binding partner for TSH receptor. The binding partner comprises or is derived from
(a) a human monoclonal antibody reactive with the TSH receptor;
(b) a recombinant antibody reactive with the TSH receptor; or
(c) a fragment of a human monoclonal antibody or a recombinant antibody reactive with the TSH receptor.

The binding partner of the invention can be used in therapeutic and diagnostic applications, and for identification of epitope regions on TSH receptor.

BRIEF DESCRIPTION OF THE DRAWINGS

FIG. 4 shows the nucleotide sequence of hMAb TSHR1 Heavy chain V, D and J region with the primer, CDR and constant region sites labeled (Seq ID No: 14).

FIG. 5 shows the amino acid sequence of hMAb TSHR1 Heavy chain V, D and J region with the CDR and constant regions labeled (Seq ID No: 5).

FIG. 6 shows the nucleotide sequence of hMAb TSHR1 Light chain with the primer and CDR sites labeled (Seq ID No: 14).

FIG. 7 shows the amino acid sequence of hMAb TSHR1 Light chain with the CDR sites labeled (Seq ID No: 6).

FIG. 9 shows the nucleotide sequence of 9D33 Heavy chain with primer, CDR and constant region sites marked. (Seq. ID No. 33).

FIG. 10 shows the amino acid sequence of 9D33 Heavy chain with primer, CDR and constant region sites marked. (Seq. ID No. 23).

FIG. 11 shows the nucleotide sequence of 9D33 light chain with primer, CDR and constant region sites marked. (Seq. ID No. 38).

FIG. 12 shows the amino acid sequence of 9D33 light chain with primer, CDR and constant region sites marked. (Seq. ID No. 28).

DETAILED DESCRIPTION OF THE INVENTION

Figure 1:
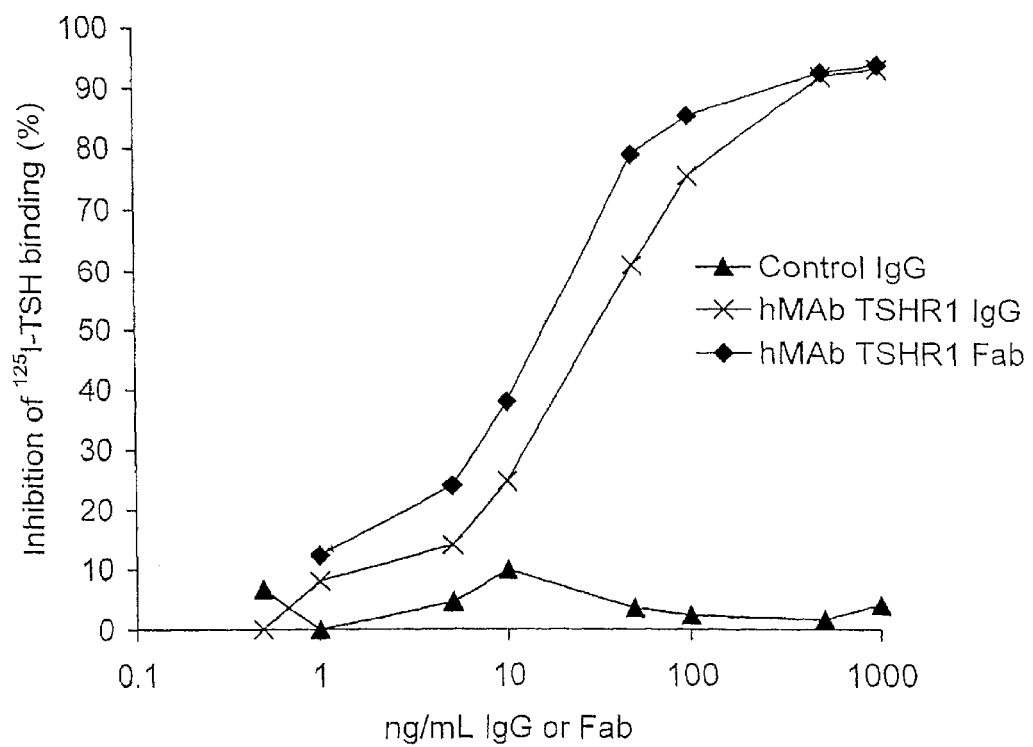
FIG. 1 shows inhibition of TSH binding to TSH Receptor in the presence of a binding partner of the invention. The control IgG was a human monoclonal antibody to $GAD_{65}$.

It is an object of the present invention to provide a binding partner for the TSH receptor capable of interacting with the TSH receptor in a manner comparable to the interaction of TSH receptor autoantibodies with the TSH receptor, in particular it is an object of the present invention to provide human monoclonal antibodies to the TSH receptor exhibiting a comparable interaction therewith as seen with TSH receptor antibodies present in the sera of patients with hyperthyroid Graves' disease and also to provide recombinant preparations thereof. The considerable difficulties of producing human monoclonal TSH receptor antibodies have been overcome in the invention described herein. In particular the successful production of a human monoclonal TSH receptor antibody with the characteristics of the autoantibodies found in the sera of patients with hyperthyroid Graves' disease is described. The human TSH receptor monoclonal antibody we have produced (described herein as hMAb TSHR 1) binds to the TSH receptor with high affinity and in such a way that small amounts of the antibody inhibit labelled TSH binding to the TSH receptor and small amounts act as powerful thyroid stimulators. Fab fragments of the antibody and recombinant Fab preparations are similarly effective thyroid stimulators and inhibitors of labelled TSH binding as intact IgG. Monoclonal Fab and/or intact IgG can be labelled with $^{125}I$ or biotin and shown to bind to the TSH receptor. Such binding is inhibited by TSH receptor autoantibodies in patient sera.

There is provided by the present invention, therefore, a binding partner for the TSH receptor, which binding partner comprises, or is derived from, a human monoclonal or recombinant antibody, or one or more fragments thereof, reactive with the TSH receptor.

In particular, there is provided by the present invention a binding partner for the TSH receptor, which binding partner comprises, or is derived from, a human monoclonal antibody, or one or more fragments thereof, reactive with the TSH receptor.

In particular, there is provided by the present invention a binding partner for the TSH receptor, which binding partner comprises, or is derived from, a human recombinant antibody, or one or more fragments thereof, reactive with the TSH receptor.

In particular, there is provided by the present invention a human monoclonal antibody, or one or more fragments thereof, reactive with the TSH receptor.

In particular, there is provided by the present invention a human recombinant antibody, or one or more fragments thereof, reactive with the TSH receptor. Particularly, the present invention provides one or more fragments of a human recombinant antibody reactive with the TSH receptor.

A binding partner according to the present invention, and in particular, a human monoclonal or recombinant antibody reactive with the TSH receptor according to the present invention can be further characterised by its ability to inhibit TSH binding to the TSH receptor, and/or its ability to stimulate the TSH receptor, both of which have been seen to be comparable to the respective inhibitory and stimulatory properties of TSH receptor autoantibodies present in sera obtained from patients with Graves' disease.

More particularly, a binding partner according to the present invention, and in particular a human monoclonal or recombinant antibody according to the present invention, can be characterised by an inhibitory activity with respect to TSH binding to the TSH receptor, of at least about 15 units of International Standard NIBSC 90/672 per mg, more preferably of at least about 30 units of International Standard NIBSC 90/672 per mg, more preferably of at least about 60 units of International Standard NIBSC 90/672 per mg, or more preferably of at least about 120 units of International Standard NIBSC 90/672 per mg, or one or more fragments of such a monoclonal or recombinant antibody.

More particularly, a binding partner according to the present invention, and in particular a human monoclonal or recombinant antibody according to the present invention, can be further characterised by a stimulatory activity with respect to cAMP production by cells expressing the TSH receptor, of at least about 30 units of International Standard NIBSC 90/672 per mg, more preferably of at least about 60 units of International Standard NIBSC 90/672 per mg, more preferably of at least about 120 units of International Standard NIBSC 90/672 per mg, or more preferably of at least about 240 units of International Standard NIBSC 90/672 per mg, or one or more fragments of such a monoclonal or recombinant antibody.

In a preferred embodiment of the present invention, a binding partner according to the present invention, and in particular a human monoclonal or recombinant antibody according to the present invention, can be characterised by:
(i) an inhibitory activity with respect to TSH binding to the TSH receptor, of at least about 15 units of International Standard NIBSC 90/672 per mg, more preferably of at least about 30 units of International Standard NIBSC 90/672 per mg, more preferably of at least about 60 units of International Standard NIBSC 90/672 per mg, or more preferably of at least about 120 units of International Standard NIBSC 90/672 per mg; and
(ii) a stimulatory activity with respect to cAMP production by cells expressing the TSH receptor, of at least about 30 units of International Standard NIBSC 90/672 per mg, more preferably of at leas about 60 units of International Standard NIBSC 90/672 per mg, more preferably of at least about 120 units of International Standard NIBSC 90/672 per mg, or more preferably of at least about 240 units of International Standard NIBSC 90/672 per mg;
or one or more fragments of such a monoclonal or recombinant antibody.

In the case where a binding partner according to the present invention comprises or is derived from one or more fragments of a monoclonal or recombinant antibody reactive with the TSH receptor, in particular for example one or more Fab fragments of a monoclonal or recombinant antibody reactive with the TSH receptor, it may be preferred that such a binding partner can be characterised by an inhibitory activity with respect to TSH binding to the TSH receptor, of at least about 30 units of International Standard NIBSC 90/672 per mg, more preferably of at least about 60 units of International Standard NIBSC 90/672 per mg, more preferably of at least about 120 units of International Standard NIBSC 90/672 per mg, or more preferably of at least about 240 units of International Standard NIBSC 90/672 per mg.

It may also be preferred in the case where a binding partner according to the present invention comprises or is derived from one or more fragments of a monoclonal or recombinant antibody reactive with the TSH receptor, in particular for example one or more Fab fragments of a monoclonal or recombinant antibody reactive with the TSH receptor, that such a binding partner can be characterised by a stimulatory activity with respect to cAMP production by cells expressing the TSH receptor, of at least about 50 units of International Standard NIBSC 90/672 per mg, more preferably of at least about 100 units of International Standard NIBSC 90/672 per mg, more preferably of at least about 200 units of International Standard NIBSC 90/672 per mg, or more preferably of at least about 400 units of International Standard NIBSC 90/672 per mg.

It may be still further preferred in the case where a binding partner according to the present invention comprises or is derived from one or more fragments of a monoclonal or recombinant antibody reactive with the TSH receptor, in particular for example one or more Fab fragments of a monoclonal or recombinant antibody reactive with the TSH receptor, that such a binding partner can be characterised by:
(i) an inhibitory activity with respect to TSH binding to the TSH receptor, of at least about 30 units of International Standard NIBSC 90/672 per mg, more preferably of at least about 60 units of International Standard NIBSC 90/672 per mg, more preferably of at least about 120 units of International Standard NIBSC 90/672 per mg, or more preferably of at least about 240 units of International Standard NIBSC 90/672 per mg; and
(ii) a stimulatory activity with respect to cAMP production by cells expressing the TSH receptor, of at least about 50 units of International Standard NIBSC 90/672 per mg, more preferably of at least about 100 units of International Standard NIBSC 90/672 per mg, more preferably of at least about 200 units of International Standard NIBSC 90/672 per mg, or more preferably of at least about 400 units of International Standard NIBSC 90/672 per mg.

In a preferred case the present invention provides a binding partner for the TSH receptor (typically a human monoclonal antibody), which binding partner is capable of binding to the TSH receptor preferably so as to stimulate the TSH receptor and which comprises an antibody $V_H$ domain selected from the group consisting of a $V_H$ domain as shown in SEQ ID NO. 1 and a $V_H$ domain comprising one or more $V_H$ CDRs with an amino acid sequence selected from SEQ ID NO. 2, SEQ ID NO. 3 and SEQ ID NO. 4.

In a first embodiment of the present invention, there is, therefore, provided a binding partner for the TSH receptor (typically a human monoclonal antibody), which binding partner is capable of binding to the TSH receptor preferably so as to stimulate the TSH receptor and which comprises an antibody $V_H$ domain as shown in SEQ ID NO. 1.

In a second embodiment of the present invention there is, therefore, provided a binding partner for the TSH receptor (typically a human monoclonal antibody), which binding partner is capable of binding to the TSH receptor preferably so as to stimulate the TSH receptor and which comprises an antibody $V_H$ domain comprising one or more $V_H$ CDRs with an amino acid sequence selected from SEQ ID NO. 2, SEQ ID NO. 3 and SEQ ID NO. 4.

It will be appreciated that a binding partner according to the present invention can comprise an antibody $V_H$ domain substantially as hereinbefore described in the absence of an antibody $V_L$ domain. It is known that single immunoglobulin domains, especially $V_H$ domains, are capable of binding target antigens in a specific manner. Alternatively, a binding partner according to the present invention can comprise an antibody $V_H$ domain paired with an antibody $V_L$ domain to provide an antibody binding site comprising both $V_H$ and $V_L$ domains for a TSH receptor employing techniques well known in the art (Biochim. Biophys. Acta, 192 (1969) 277-285; Proc. Natl. Acad. Sci. USA, Vol. 89, pp 10026-10030, November 1992).

In a preferred case the present invention provides, however, a binding partner for the TSH receptor, which binding partner is capable of binding to the TSH receptor preferably so as to stimulate the TSH receptor and which comprises:

an antibody $V_H$ domain selected from the group consisting of:
    a $V_H$ domain as shown in SEQ ID NO. 1 and a $V_H$ domain comprising one or more $V_H$ CDRs with an amino acid sequence selected from SEQ ID NO. 2, SEQ ID NO. 3 and SEQ ID NO. 4; and/or an antibody $V_L$ domain selected from the group consisting of:
    a $V_L$ domain as shown in SEQ ID NO. 6 and a $V_L$ domain comprising one or more $V_L$ CDRs with an amino acid sequence selected from SEQ ID NO. 7, SEQ ID NO. 8 and SEQ ID NO. 9.

It may be preferred according to the present invention that a binding partner substantially as hereinbefore described comprises an antibody $V_H$ domain substantially as hereinbefore described paired with an antibody $V_L$ domain substantially as hereinbefore described to provide an antibody binding site comprising both $V_H$ and $V_L$ domains for the TSH receptor, although as discussed further an antibody $V_H$ domain, or an antibody $V_L$ domain, may be independently used to bind a TSH receptor. It will be appreciated, therefore, that a binding partner substantially as hereinbefore described can comprise an antibody $V_H$ domain substantially as hereinbefore described in the absence of an antibody $V_L$ domain. It will also be appreciated, therefore, that a binding partner substantially as hereinbefore described can comprise an antibody $V_L$ domain substantially as hereinbefore described in the absence of an antibody $V_H$ domain. Alternatively, a binding partner substantially as hereinbefore described can comprise an antibody $V_H$ domain paired with an antibody $V_L$ domain substantially as hereinbefore described to provide an antibody binding site comprising both $V_H$ and $V_L$ domains for the TSH receptor.

Preferred embodiments according to the present invention can thus include a binding partner substantially as hereinbefore described comprising an antibody $V_H$ domain as shown in SEQ ID NO. 1 paired with an antibody $V_L$ domain as shown in SEQ ID NO. 6 to provide an antibody binding site, comprising both these $V_H$ and $V_L$ domains for the TSH receptor.

It is further envisaged according to the present invention that $V_H$ domains substantially as hereinbefore described may be paired with $V_L$ domains other than those specifically described herein. It is also further envisaged according to the present invention that $V_L$ domains substantially as hereinbefore described may be paired with $V_H$ domains other than those specifically described herein.

According to a further embodiment of the present invention there is provided a binding partner substantially as hereinbefore described for the TSH receptor, which binding partner is capable of binding to the TSH receptor so as to stimulate the TSH receptor and which can comprise:

an antibody $V_H$ domain comprising:
    a $V_H$ domain comprising one or more $V_H$ CDRs with an amino acid sequence selected from SEQ ID NO. 2, SEQ ID NO. 3 and SEQ ID NO. 4; and/or an antibody $V_L$ domain comprising:
    a $V_L$ domain comprising one or more $V_L$ CDRs with an amino acid sequence selected from SEQ ID NO. 7, SEQ ID NO. 8 and SEQ ID NO. 9.

One or more CDRs as referred to above may be taken from the hereinbefore described $V_1$ and $V_L$ domains and incorporated into a suitable framework. For example, the amino acid sequence of one or more CDRs substantially as hereinbefore described may be incorporated into framework regions of antibodies differing from hMAb TSHR 1 specifically disclosed herein, such antibodies thereby incorporating the one or more CDRs and being capable of binding to the TSH receptor, preferably to stimulate the TSH receptor substantially as hereinbefore described. Alternatively, the present invention may provide a polypeptide capable of binding to the TSH receptor so as to stimulate the TSH receptor substantially as hereinbefore described and comprising the primary structural conformation of amino acids as represented by one or more CDRs as specifically described herein, optionally together with further amino acids, which further amino acids may enhance the binding affinity of one or more CDRs as described herein for the TSH receptor or may have substantially no role in affecting the binding properties of the polypeptide for the TSH receptor.

The present invention, also encompasses variants, analogs, derivatives and fragments of the specific human monoclonal antibody described herein, $V_H$ domains, CDRs and polypeptides disclosed herein, which variants, analogs, derivatives and fragments retain the ability to interact with the TSH receptor (such as for example to stimulate the TSH receptor) substantially as hereinbefore described.

The terms "variants", "analogs", "derivatives" and "fragments" as used herein can be characterised as antibodies, antibody fragments or polypeptides which retain essentially the same biological function or activity as a human monoclonal antibody having a $V_H$ domain as shown in SEQ ID NO. 1 and a $V_L$ domain as shown in SEQ ID NO. 6 and in particular in respect of the binding properties thereof for the TSH receptor. Suitably, variants, analogs, derivatives and fragments, and variants, analogs and derivatives of the fragments as described herein, have a primary structural conformation of amino acids in which several or a few (such as 5 to 10, 1 to 5 or 1 to 3) amino acid residues of a human monoclonal antibody having a $V_H$ domain as shown in SEQ ID NO. 1 and a $V_L$ domain as shown in SEQ ID NO. 6 are substituted, deleted or added, in any combination. Especially preferred among these are silent substitutions, additions and deletions which do not alter or substantially alter the biological activity or function of a human monoclonal antibody having a $V_H$ domain as shown in SEQ ID NO. 1 and a $V_L$ domain as shown in SEQ ID NO. 6. Conservative substitutions can be preferred as hereinafter described in greater detail.

More particularly, variants, analogs or derivatives of a human monoclonal antibody having a $V_H$ domain as shown in SEQ ID NO. 1 and a $V_L$ domain as shown in SEQ ID NO. 6 according to the present invention may be ones in which one or more of the amino acid residues are substituted with a conserved or non-conserved amino acid residue (preferably a conserved amino acid residue), or ones in which one or more of the amino acid resides includes a substituent group or the like. Such variants, derivatives and analogs are deemed to be within the scope of those skilled in the art from the teachings herein.

Most typically, variants, analogs or derivatives are those that vary from a reference human monoclonal antibody having a $V_H$ domain as shown in SEQ ID NO. 1 and a $V_L$ domain as shown in SEQ ID NO. 6 by conservative amino acid substitutions. Such substitutions are those that substitute a given amino acid by another amino acid of like characteristics. Typically seen as conservative substitutions are the replacements, one for another, among the aliphatic amino acids A, V, L and I; among the hydroxyl residues S and T; among the acidic residues D and E; among the amide residues N and Q; among the basic residues K and R; and among the aromatic residues F and Y.

It will be appreciated that the term fragment as used herein in particular relates to fragments of antibodies specifically as herein described and form an important aspect of the present invention.

In this way, a human monoclonal or recombinant antibody as provided by the present invention may be provided as any of the following fragments: (i) the Fab fragment consisting of $V_L$, $V_H$, $C_L$ and $C_H 1$ domains; (ii) the Fd fragment consisting of the $V_H$ and $C_H 1$ domains; (iii) the Fv fragment consisting of the $V_L$ and $V_H$ domains; (iv) the dAb fragment which consists of a $V_H$ domain; (v) isolated CDR regions; (vi) F (ab') 2 fragments, a bivalent fragment comprising two linked Fab fragments; and (vii) single chain Fv molecules (scFv), wherein a $V_H$ domain and a $V_L$ domain are linked by a peptide linker which allows the two domains to associate to form an antigen binding site.

Alternatively, a human monoclonal or recombinant antibody according to the present invention may comprise a whole IgG antibody, whereby the antibody includes variable and constant regions.

The present invention also provides a further binding partner capable of binding to the TSH receptor, which can compete for binding to the TSH receptor with a binding partner for the TSH receptor (typically a human monoclonal antibody) substantially as hereinbefore described, which further binding partner does not comprise TSH. Preferably, this further binding partner may comprise a further antibody having a binding site for an epitope region of the TSH receptor, and which can compete for binding to the TSH receptor with a binding partner for the TSH receptor (typically a human monoclonal antibody) substantially as hereinbefore described. A suitable such further binding partner can comprise a mouse monoclonal antibody, which can preferably be produced according to techniques substantially as described in the Examples, employing immunisation of mice with TSH receptor by techniques known in the art.

The present invention may also provide a further binding partner capable of binding to the TSH receptor, which can comprise, or is derived from, a human monoclonal or recombinant antibody, or one or more fragments thereof, reactive with the TSH receptor. In particular this further binding partner may comprise a further antibody having a binding site for an epitope region of the TSH receptor, which further antibody is capable of binding to the TSH receptor, and can compete for binding to the TSH receptor with a binding partner for the TSH receptor (typically a human monoclonal antibody) substantially as hereinbefore described. Suitably such a further binding partner can be derived from a specific binding partner as described herein, hMAb TSHR 1, by suitable mutagenesis techniques, such as spot mutations or the like, so as to obtain a further binding partner for the TSH receptor that can compete with a binding partner substantially as herein described (such as hMAb TSHR 1) for interaction with the TSH receptor.

Preferably a further binding partner for the TSH receptor can comprise a monoclonal or recombinant antibody and can be characterised by an inhibitory activity with respect to TSH binding to the TSH receptor, of at least about 15 units of International Standard NIBSC 90/672 per mg, more preferably of at least about 30 units of International Standard NIBSC 90/672 per mg, more preferably of at least about 60 units of International Standard NIBSC 90/672 per mg, or more preferably of at least about 120 units of International Standard NIBSC 90/672 per mg, or one or more fragments of the antibody. It may also be preferred that such a further binding partner according to the present invention, can be characterised by a stimulatory activity with respect to cAMP production by cells expressing the TSH receptor, of at least about 30 units of International Standard NIBSC 90/672 per mg, more preferably of at least about 60 units of International Standard NIBSC 90/672 per mg, more preferably of at least about 120 units of International Standard NIBSC 90/672 per mg, or more preferably of at least about 240 units of International Standard NIBSC 90/672 per mg, or one or more fragments of the antibody.

It may also be even more preferred that such a further binding partner of the present invention, can be characterised by:
(i) an inhibitory activity with respect to TSH binding to the TSH receptor, of at least about 15 units of International Standard NIBSC 90/672 per mg, more preferably of at least about 30 units of International Standard NIBSC 90/672 per mg, more preferably of at least about 60 units of International Standard NIBSC 90/672 per mg, or more preferably of at least about 120 units of International Standard NIBSC 90/672 per mg; and
(ii) a stimulatory activity with respect to cAMP production by cells expressing the TSH receptor, of at least about 30 units of International Standard NIBSC 90/672 per mg, more preferably of at least about 60 units of International Standard NIBSC 90/672 per mg, more preferably of at least about 120 units of International Standard NIBSC 90/672 per mg, or more preferably of at least about 240 units of International Standard NIBSC 90/672 per mg;
or one or more fragments thereof.

A preferred mouse monoclonal antibody providing a further binding partner according to the present invention comprises 9D33 prepared further to the Examples and having amino acid and polynucleotide sequences as illustrated by FIGS. 9 to 12 and Sequence Listings 19 to 38. According to the present invention, there is, therefore, provided a further binding partner for the TSH receptor (typically a mouse monoclonal antibody), which comprises an antibody $V_H$ domain as shown in SEQ ID NO. 19.

A further binding partner as provided by the present invention can also be characterised as comprising an antibody $V_H$ domain comprising one or more $V_H$ CDRs with an amino acid sequence selected from SEQ ID NO. 20, SEQ ID NO. 21 and SEQ ID NO. 22.

It will be appreciated that a further binding partner according to the present invention can comprise an antibody $V_H$ domain substantially as hereinbefore described in the absence of an antibody $V_L$ domain. It is known that single immunoglobulin domains, especially $V_H$ domains, are capable of binding target antigens in a specific manner. Alternatively, a further binding partner according to the present invention can comprise an antibody $V_H$ domain paired with an antibody $V_L$ domain to provide an antibody binding site comprising both $V_H$ and $V_L$ domains for a TSH receptor employing techniques well known in the art (Biochim. Biophys. Acta, 192 (1969) 277-285; Proc. Natl. Acad. Sci. USA, Vol. 89, pp 10026-10030, November 1992).

In a preferred case the present invention provides, however, a further binding partner for the TSH receptor, which further binding partner comprises:

an antibody $V_H$ domain selected from the group consisting of:
   a $V_H$ domain as shown in SEQ ID NO. 19 and a $V_H$ domain comprising one or more $V_H$ CDRs with an amino acid sequence selected from SEQ ID NO. 20, SEQ ID NO. 21 and SEQ ID NO. 22; and/or an antibody $V_L$ domain selected from the group consisting of:
   a $V_L$ domain as shown in SEQ ID NO. 24 and a $V_L$ domain comprising one or more $V_L$ CDRs with an amino acid sequence selected from SEQ ID NO. 25, SEQ ID NO. 26 and SEQ ID NO. 27.

It may be preferred according to the present invention that a further binding partner substantially as hereinbefore described comprises an antibody $V_H$ domain substantially as hereinbefore described paired with an antibody $V_L$ domain substantially as hereinbefore described to provide an antibody binding site comprising both $V_H$ and $V_L$ domains for the TSH receptor, although as discussed further an antibody $V_H$ domain, or an antibody $V_L$ domain, may be independently used to bind a TSH receptor. It will be appreciated, therefore, that a further binding partner substantially as hereinbefore described can comprise an antibody $V_H$ domain substantially as hereinbefore described in the absence of an antibody $V_L$ domain. It will also be appreciated, therefore, that a further binding partner substantially as hereinbefore described can comprise an antibody $V_L$ domain substantially as hereinbefore described in the absence of an antibody $V_H$ domain. Alternatively, a further binding partner substantially as hereinbefore described can comprise an antibody $V_H$ domain paired with an antibody $V_L$ domain substantially as hereinbefore described to provide an antibody binding site comprising both $V_H$ and $V_L$ domains for the TSH receptor.

Preferred embodiments according to the present invention can thus include a further binding partner substantially as hereinbefore described comprising an antibody $V_H$ domain as shown in SEQ ID NO. 19 paired with an antibody $V_L$ domain as shown in SEQ ID NO. 24 to provide an antibody binding site, comprising both these $V_H$ and $V_L$ domains for the TSH receptor.

It is further envisaged according to the present invention that $V_H$ domains substantially as hereinbefore described may be paired with $V_L$ domains other than those specifically described herein. It is also further envisaged according to the present invention that $V_L$ domains substantially as hereinbefore described may be paired with $V_H$ domains other than those specifically described herein.

According to a further embodiment of the present invention there is provided a further binding partner substantially as hereinbefore described for the TSH receptor, which further binding partner is capable of binding to the TSH receptor so as to inhibit stimulation of the TSH receptor and which can comprise:

an antibody $V_H$ domain comprising:
   a $V_H$ domain comprising one or more $V_H$ CDRs with an amino acid sequence selected from SEQ ID NO. 20, SEQ ID NO. 21 and SEQ ID NO. 22; and/or an antibody $V_L$ domain comprising:
   a $V_L$ domain comprising one or more $V_L$ CDRs with an amino acid sequence selected from SEQ ID NO. 25, SEQ ID NO. 26 and SEQ ID NO. 27.

One or more CDRs as referred to above may be taken from the hereinbefore described $V_H$ and $V_L$ domains and incorporated into a suitable framework. For example, the amino acid sequence of one or more CDRs substantially as hereinbefore described may be incorporated into framework regions of antibodies differing from 9D33 specifically disclosed herein, such antibodies thereby incorporating the one or more CDRs and being capable of binding to the TSH receptor. Alternatively, the present invention may provide a polypeptide capable of binding to the TSH receptor comprising the primary structural conformation of amino acids as represented by one or more CDRs as specifically described herein, optionally together with further amino acids, which further amino acids may enhance the binding affinity of one or more CDRs as described herein for the TSH receptor or may have substantially no role in affecting the binding properties of the polypeptide for the TSH receptor.

It will be appreciated that the term fragment as used herein in particular relates to fragments of antibodies specifically as herein described and form an important aspect of the present invention. In this way, a further binding partner according to the present invention may be provided as any of the following fragments: (i) the Fab fragment consisting of $V_L$, $V_H$, $C_L$ and $C_H 1$ domains; (ii) the Fd fragment consisting of the $V_H$ and $C_H 1$ domains; (iii) the Fv fragment consisting of the $V_L$ and $V_H$ domains; (iv) the dAb fragment which consists of a $V_H$ domain; (v) isolated CDR regions; (vi) F (ab') 2 fragments, a bivalent fragment comprising two linked Fab fragments; and (vii) single chain Fv molecules (scFv), wherein a $V_H$ domain and a $V_L$ domain are linked by a peptide linker which allows the two domains to associate to form an antigen binding site.

Alternatively, a mouse monoclonal or recombinant antibody according to the present invention, such as 9D33, may comprise a whole IgG antibody, whereby the antibody includes variable and constant regions.

There is also provided by the present invention a polynucleotide comprising:

(i) a nucleotide sequence as shown in SEQ ID NO. 10, SEQ ID NO. 11, SEQ ID NO. 12, SEQ ID NO. 13, SEQ ID NO. 15, SEQ ID NO. 16, SEQ ID NO. 17 or SEQ ID NO. 18, encoding an amino acid sequence of an antibody $V_H$ domain, $V_L$ domain, or CDR, as shown in SEQ ID NO. 1, SEQ ID NO. 2, SEQ ID NO. 3, SEQ ID NO. 4, SEQ ID NO. 6, SEQ ID NO. 7, SEQ ID NO. 8 or SEQ ID NO. 9;

(ii) a nucleotide sequence encoding a binding partner for the TSH receptor (typically a human monoclonal antibody) substantially as hereinbefore described, or encoding an amino acid sequence of an antibody $V_H$ domain, $V_L$ domain, or CDR, of a binding partner for the TSH receptor (typically a human monoclonal antibody) substantially as hereinbefore described;

(iii) a nucleotide sequence differing from any sequence of (i) in codon sequence due to the degeneracy of the genetic code;

(iv) a nucleotide sequence comprising an allelic variation of any sequence of (i);

(v) a nucleotide sequence comprising a fragment of any of the sequences of (i), (ii), (iii), or (iv) and in particular a nucleotide sequence comprising a fragment of any of the sequences of (i), (ii), (iii), (iv) or (v) and encoding a Fab fragment, a Fd fragment, a Fv fragment, a dAb fragment, an isolated CDR region, F (ab') 2 fragments or a scFv fragment, of a human monoclonal antibody substantially as hereinbefore described;

(vi) a nucleotide sequence differing from the any sequence of (i) due to mutation, deletion or substitution of a nucleotide base and encoding a binding partner for the TSH receptor (typically a human monoclonal antibody) substantially as hereinbefore described, or encoding an amino acid sequence of an antibody $V_H$ domain, $V_L$ domain, or CDR, of a binding partner for the TSH receptor (typically a human monoclonal antibody) substantially as hereinbefore described.

There is also provided by the present invention a polynucleotide comprising:

(i) a nucleotide sequence as shown in SEQ ID NO. 29, SEQ ID NO. 30, SEQ ID NO. 31, SEQ ID NO. 32, SEQ ID NO. 34, SEQ ID NO. 35, SEQ ID NO. 36 or SEQ ID NO. 37, encoding an amino acid sequence of an antibody $V_H$ domain, $V_L$ domain, or CDR, as shown in SEQ ID NO. 19, SEQ ID NO. 20, SEQ ID NO. 21, SEQ ID NO. 22, SEQ ID NO. 24, SEQ ID NO. 25, SEQ ID NO. 26 or SEQ ID NO. 27;

(ii) a nucleotide sequence encoding a further binding partner for the TSH receptor (typically a mouse monoclonal antibody) substantially as hereinbefore described, or encoding an amino acid sequence of an antibody $V_H$ domain, $V_L$ domain, or CDR, of a further binding partner for the TSH receptor (typically a mouse monoclonal antibody) substantially as hereinbefore described;

(iii) a nucleotide sequence differing from any sequence of (i) in codon sequence due to the degeneracy of the genetic code;

(iv) a nucleotide sequence comprising an allelic variation of any sequence of (i);

(v) a nucleotide sequence comprising a fragment of any of the sequences of (i), (ii), (iii), or (iv) and in particular a nucleotide sequence comprising a fragment of any of the sequences of (i), (ii), (iii), (iv) or (v) and encoding a Fab fragment, a Fd fragment, a Fv fragment, a dAb fragment, an isolated CDR region, F (ab') 2 fragments or a scFv fragment, of a mouse monoclonal antibody substantially as hereinbefore described;

(vi) a nucleotide sequence differing from the any sequence of (i) due to mutation, deletion or substitution of a nucleotide base and encoding a further binding partner for the TSH receptor (typically a mouse monoclonal antibody) substantially as hereinbefore described, or encoding an amino acid sequence of an antibody $V_H$ domain, $V_L$ domain, or CDR, of a further binding partner for the TSH receptor (typically a mouse monoclonal antibody) substantially as hereinbefore described.

Variant polynucleotides according to the present invention are suitably at least 70% identical over their entire length to any polynucleotide sequence of (i), most highly preferred are polynucleotides that comprise a region that is at least 80% identical over its entire length to any polynucleotide sequence of (i), polynucleotides at least 90% identical over their entire length to any polynucleotide sequence of (i) are particularly preferred, and among these particularly preferred polynucleotides, those with at least 95% identity are especially preferred.

The present invention further provides a biologically functional vector system which carries a polynucleotide substantially as hereinbefore described and which is capable of introducing the polynucleotide into the genome of a host organism.

The present invention also relates to host cells which are transformed with polynucleotides of the invention and the production of binding partners for the TSH receptor of the invention by recombinant techniques. Host cells can be genetically engineered to incorporate polynucleotides and express binding partners for the TSH receptor of the present invention.

The amino acid sequences of hMAb TSHR 1, a human monoclonal antibody according to the present invention, and nucleotide sequences coding therefor, the amino acid sequences of 9D33, a mouse monoclonal antibody which represents a further binding partner according to the present invention, and nucleotide sequences coding therefor, are shown in the Sequence listings as herein after described and can be assigned as follows.

For hMAb TSHR 1:

| Amino Acid Sequences | |
|---|---|
| SEQ ID NO. 1 | $V_H$ |
| SEQ ID NO. 2 | $V_H$ CDRI |
| SEQ ID NO. 3 | $V_H$ CDRII |
| SEQ ID NO. 4 | $V_H$ CDRIII |
| SEQ ID NO. 5 | Heavy chain variable and adjacent constant region |
| SEQ ID NO. 6 | $V_L$ |
| SEQ ID NO. 7 | $V_L$ CDRI |
| SEQ ID NO. 8 | $V_L$ CDRII |
| SEQ ID NO. 9 | $V_L$ CDRIII |
| Nucleotide Sequences | |
| SEQ ID NO. 10 | $V_H$ |
| SEQ ID NO. 11 | $V_H$ CDRI |
| SEQ ID NO. 12 | $V_H$ CDRII |
| SEQ ID NO. 13 | $V_H$ CDRIII. |
| SEQ ID NO. 14 | Heavy chain variable and adjacent constant region |
| SEQ ID NO. 15 | $V_L$ |
| SEQ ID NO. 16 | $V_L$ CDRI |
| SEQ ID NO. 17 | $V_L$ CDRII |
| SEQ ID NO. 18 | $V_L$ CDRIII |

For 9D33:

| Amino Acid Sequences | |
|---|---|
| SEQ ID NO. 19 | $V_H$ |
| SEQ ID NO. 20 | $V_H$ CDRI |
| SEQ ID NO. 21 | $V_H$ CDRII |
| SEQ ID NO. 22 | $V_H$ CDRIII |
| SEQ ID NO. 23 | Heavy chain variable and adjacent constant region |
| SEQ ID NO. 24 | $V_L$ |
| SEQ ID NO. 25 | $V_L$ CDRI |
| SEQ ID NO. 26 | $V_L$ CDRII |
| SEQ ID NO. 27 | $V_L$ CDRIII |
| SEQ ID NO. 28 | Light chain variable and adjacent constant region |
| Nucleotide Sequences | |
| SEQ ID NO. 29 | $V_H$ |
| SEQ ID NO. 30 | $V_H$ CDRI |
| SEQ ID NO. 31 | $V_H$ CDRII |
| SEQ ID NO. 32 | $V_H$ CDRIII |
| SEQ ID NO. 33 | Heavy chain variable and adjacent constant region |
| SEQ ID NO. 34 | $V_L$ |
| SEQ ID NO. 35 | $V_L$ CDRI |
| SEQ ID NO. 36 | $V_L$ CDRII |
| SEQ ID NO. 37 | $V_L$ CDRIII |
| SEQ ID NO. 38 | Light chain variable and adjacent constant region |

The above sequences for hMab TSHR1 can also be seen by reference to FIGS. 4, 5, 6 and 7, wherein:

FIG. 4 shows the hMab TSHR1 heavy chain nucleotide sequence, along with the adjacent constant region, annotated with the PCR primer, CDRI, CDRII, CDRIII and constant regions;

FIG. 5 shows the hMab TSHR1 heavy chain amino acid sequence, along with the adjacent constant region, annotated with the CDRI, CDRII, CDRIII and constant regions;

FIG. 6 shows the hMab TSHR1 light chain nucleotide sequence annotated with the PCR primer, CDRI, CDRII and CDRIII regions; and FIG. 7 shows the hMab TSHR1 light chain amino acid sequence annotated with the CDRI, CDRII and CDRIII regions.

It will be appreciated from the above that for the $V_H$ chain of hMab TSHR1 the nucleotide sequences of the CDRI, CDRII and CDRIII regions as shown in FIG. 4 correspond to the $V_H$CDRI, $V_H$CDRII and $V_H$CDRIII sequences shown in SEQ ID NO.s 11, 12 and 13 respectively, and that the amino acid sequences of the CDRI, CDRII and CDRIII regions as shown in FIG. 5 correspond to the $V_H$ CDRI, $V_H$ CDRII and $V_H$ CDRIII sequences shown in SEQ ID NO.s 2, 3 and 4 respectively. It will also be appreciated from the above that for the $V_L$ chain of hMab TSHR1 the nucleotide sequences of the CDRI, CDRII and CDRIII regions as shown in FIG. 6 correspond to the $V_L$ CDRI, $V_L$ CDRII and $V_L$ CDRIII sequences shown in SEQ ID NO.s 16, 17 and 18 respectively, and that the amino acid sequences of the CDRI, CDRII and CDRIII regions as shown in FIG. 7 correspond to the $V_L$ CDRI, $V_L$ CDRII and $V_L$ CDRIII sequences shown in SEQ ID NO.s 7, 8 and 9 respectively.

Analysis of the crystal structure of hMAb TSHRI Fab (determined by techniques known in the art) enabled refinement of the HC and LC nucleotide sequences determined using PCR primers which are degenerate. In particular, a HC sequencing artefact for nucleotides 115-120 was identified. Sequencing indicated cacgtg (transcribed to amino acids H is Val), whereas the crystal structure more reliably indicated amino acids Gln Leu (corresponding bases being cagctg), with the refined sequences being shown in the accompanying Figures and Sequence listings. Crystal structure analysis also enabled refinement of the HC and LC derived amino acid sequences particularly in the degenerate PCR primer region. In the case of the LC aa 2 was found to be Pro by RT-PCR but was Thr from the crystal structure. In the case of the HC aa 2 was found to be Met by RT-PCR but was Val from the crystal structure. Again, these refined sequences are shown in the accompanying Figures and Sequence listings.

The above sequences for 9D33 can also be seen by reference to FIGS. 9, 10, 11 and 12, wherein:

FIG. 9 shows the 9D33 heavy chain nucleotide sequence, along with the adjacent constant region, annotated with the PCR primer, CDRI, CDRII, CDRIII and constant regions;

FIG. 10 shows the 9D33 heavy chain amino acid sequence, along with the adjacent constant region, annotated with the PCR primer, CDRI, CDRII, CDRIII and constant regions;

FIG. 11 shows the 9D33 light chain nucleotide sequence annotated with the PCR primer, CDRI, CDRII, CDRIII and constant regions;

FIG. 12 shows the 9D33 light chain amino acid sequence annotated with the PCR primer, CDRI, CDRII, CDRIII and constant regions.

It will be appreciated from the above that for the $V_H$ chain of 9D33 the nucleotide sequences of the CDRI, CDRII and CDRIII regions as shown in FIG. 9 correspond to the $V_H$ CDRI, $V_H$CDRII and $V_H$CDRIII sequences shown in SEQ ID NO.s 30, 31 and 32 respectively, and that the amino acid sequences of the CDRI, CDRII and CDRIII regions as shown in FIG. 10 correspond to the $V_H$ CDRI, $V_H$ CDRII and $V_H$CDRIII sequences shown in SEQ ID NO.s 20, 21 and 22 respectively. It will also be appreciated from the above that for the $V_L$ chain of 9D33 the nucleotide sequences of the CDRI, CDRII and CDRIII regions as shown in FIG. 11 correspond to the $V_L$ CDRI, $V_L$ CDRII and $V_L$ CDRIII sequences shown in SEQ ID NO.s 35, 36 and 37 respectively, and that the amino acid sequences of the CDRI, CDRII and CDRIII regions as shown in FIG. 12 correspond to the $V_L$ CDRI, $V_L$ CDRII and $V_L$ CDRIII sequences shown in SEQ ID NO.s 25, 26 and 27 respectively.

The present invention also provides a process of providing a human monoclonal antibody to the TSH receptor substantially as hereinbefore described, which process comprises:
(i) providing a source of lymphocytes from a subject, which subject has TSH receptor antibody activity of greater than about 0.04 units of NIBSC 90/672 per mL of serum with respect to inhibition of TSH binding to the TSH receptor;
(ii) isolating lymphocytes from said lymphocyte source of (i);
(iii) immortalising the isolated lymphocytes; and
(iv) cloning the immortalised lymphocytes so as to produce an immortalised colony secreting a human monoclonal antibody to the TSH receptor substantially as hereinbefore described.

Alternatively, a process of providing a human monoclonal antibody to the TSH receptor substantially as hereinbefore described can be defined as a process which comprises:
(i) providing a source of lymphocytes from a subject, which subject has TSH receptor antibody activity of greater than about 0.1 units of NIBSC 90/672 per mL of serum with respect to stimulatory activity of cAMP production by cells expressing the TSH receptor;
(ii) isolating lymphocytes from said lymphocyte source of (i);
(iii) immortalising the isolated lymphocytes; and
(iv) cloning the immortalised lymphocytes so as to produce an immortalised colony secreting a human monoclonal antibody to the TSH receptor substantially as hereinbefore described.

Preferably a process according to the present invention comprises isolating lymphocytes from peripheral blood, thyroid tissue, spleen tissue, lymph nodes or bone marrow, most typically from peripheral blood. Typically, the source of lymphocytes for use in a method according to the present invention can be further characterised as being obtained from a subject having serum TSH receptor antibody levels of greater than about 0.1 units of NIBSC 90/672 per mL with respect to inhibition of TSH binding to the TSH receptor, or more typically greater than about 0.2 units of NIBSC 90/672 per mL with respect to inhibition of TSH binding to the TSH receptor, or more typically greater than about 0.3 units of NIBSC 90/672 per mL with respect to inhibition of TSH binding to the TSH receptor and preferably being in the range of about 0.3 to 0.5 units of NIBSC 90/672 per mL or greater with respect to inhibition of TSH binding to the TSH receptor. Alternatively, or additionally, the source of lymphocytes for use in a method according to the present invention can typically be further characterised as being obtained from a subject having serum TSH receptor antibody levels of greater than about 0.2 units of NIBSC 90/672 per mL with respect to stimulatory activity of cAMP production by cells expressing the TSH receptor, or more typically greater than about 0.5 units of NIBSC 90/672 per mL with respect to stimulatory activity of cAMP production by cells expressing the TSH receptor and preferably being in the range of about 0.5 to 1.0 units of NIBSC 90/672 per mL or greater with respect to stimulatory activity of cAMP production by cells expressing the TSH receptor. It will be appreciated from the above that the immune response to the TSH receptor of a subject from which lymphocytes are isolated should preferably be in a highly active phase.

Preferably a process according to the present invention comprises infecting the isolated lymphocytes with Epstein Barr virus, and suitably the thus immortalised lymphocytes are fused with a mouse/human cell line. Suitably a process according to the present invention further comprises screening the resulting clones for TSH receptor antibodies, for example by inhibition of $^{125}$I TSH binding to the TSH receptor in an assay system which has a sensitivity of at least about 1 unit/L of NIBSC 90/672.

The present invention further provides a process of preparing a human recombinant antibody, or one or more fragments thereof, to the TSH receptor, which process comprises cloning and expression of a human monoclonal antibody to the TSH receptor as provided by the present invention by a process substantially as hereinbefore described, or one or more fragments derived therefrom.

The present invention further provides a human monoclonal or recombinant antibody to the TSH receptor obtained by a process substantially as described above. Preferably such an obtained human monoclonal or recombinant antibody to the TSH receptor according to the present invention, can be characterised by an inhibitory activity with respect to TSH binding to the TSH receptor, of at least about 15 units of International Standard NIBSC 90/672 per mg, more preferably of at least about 30 units of International Standard NIBSC 90/672 per mg, more preferably of at least about 60 units of International Standard NIBSC 90/672 per mg, or more preferably of at least about 120 units of International Standard NIBSC 90/672 per mg, or one or more fragments of such a human monoclonal or recombinant antibody.

More particularly, it may be preferred that such a human monoclonal or recombinant antibody according to the present invention, can be further characterised by a stimulatory activity with respect to cAMP production by cells expressing the TSH receptor, of at least about 30 units of International Standard NIBSC 90/672 per mg, more preferably of at least about 60 units of International Standard NIBSC 90/672 per mg, more preferably of at least about 120 units of International Standard NIBSC 90/672 per mg, or more preferably of at least about 240 units of International Standard NIBSC 90/672 per mg, or one or more fragments of such a human monoclonal or recombinant antibody.

In a preferred embodiment of the present invention, such a human monoclonal or recombinant antibody according to the present invention, can be characterised by:
  (i) an inhibitory activity with respect to TSH binding to the TSH receptor, of at least about 15 units of International Standard NIBSC 90/672 per mg, more preferably of at least about 30 units of International Standard NIBSC 90/672 per mg, more preferably of at least about 60 units of International Standard NIBSC 90/672 per mg, or more preferably of at least about 120 units of International Standard NIBSC 90/672 per mg; and
  (ii) a stimulatory activity with respect to cAMP production by cells expressing the TSH receptor, of at least about 30 units of International Standard NIBSC 90/672 per mg, more preferably of at least about 60 units of International Standard NIBSC 90/672 per mg, more preferably of at least about 120 units of International Standard NIBSC 90/672 per mg, or more preferably of at least about 240 units of International Standard NIBSC 90/672 per mg;
or one or more fragments of such a human monoclonal or recombinant antibody.

It may also be preferred that one or more fragments of a thus obtained human monoclonal or recombinant antibody according to the present invention, in particular for example one or more Fab fragments thereof, can be characterised by an inhibitory activity with respect to TSH binding to the TSH receptor, of at least about 30 units of International Standard NIBSC 90/672 per mg, more preferably of at least about 60 units of International Standard NIBSC 90/672 per mg, more preferably of at least about 120 units of International Standard NIBSC 90/672 per mg, or more preferably of at least about 240 units of International Standard NIBSC 90/672 per mg. It may also be preferred that such one or more fragments can be characterised by a stimulatory activity with respect to cAMP production by cells expressing the TSH receptor, of at least about 50 units of International Standard NIBSC 90/672 per mg, or more preferably of at least about 100 units of International Standard NIBSC 90/672 per mg, or more preferably of at least about 200 units of International Standard NIBSC 90/672 per mg, or more preferably of at least about 400 units of International Standard NIBSC 90/672 per mg.

More preferably, such one or more Fab fragments can be characterised by:
  (i) an inhibitory activity with respect to TSH binding to the TSH receptor, of at least about 30 units of International Standard NIBSC 90/672 per mg, more preferably of at least about 60 units of International Standard NIBSC 90/672 per mg, more preferably of at least about 120 units of International Standard NIBSC 90/672 per mg, or more preferably of at least about 240 units of International Standard NIBSC 90/672 per mg; and
  (ii) a stimulatory activity with respect to cAMP production by cells expressing the TSH receptor, of at least about 50 units of International Standard NIBSC 90/672 per mg, or more preferably of at least about 100 units of International Standard NIBSC 90/672 per mg, or more preferably of at least about 200 units of International Standard NIBSC 90/672 per mg, or more preferably of at least about 400 units of International Standard NIBSC 90/672 per mg.

A process substantially as described above may further comprise a further process stage whereby the obtained human monoclonal or recombinant antibody is subjected to suitable further processing techniques (such as suitable mutagenesis techniques, such as spot mutations or the like), so as to obtain a further binding partner for the TSH receptor that can compete with a binding partner substantially as herein described (such as hMAb TSHR 1) for interaction with the TSH receptor. Such further processing techniques are well known to one of ordinary skill in the art. The present invention further provides a further binding partner to the TSH receptor obtained by such further processing techniques.

Preferably such a further binding partner for the TSH receptor can comprise a monoclonal or recombinant antibody and can be characterised by an inhibitory activity with respect to TSH binding to the TSH receptor, of at least about 15 units of International Standard NIBSC 90/672 per mg, more preferably of at least about 30 units of International Standard NIBSC 90/672 per mg, more preferably of at least about 60 units of International Standard NIBSC 90/672 per mg, or more preferably of at least about 120 units of International Standard NIBSC 90/672 per mg, or one or more fragments thereof. It may also be preferred that such a further binding partner according to the present invention, can be characterised by a stimulatory activity with respect to cAMP production by cells expressing the TSH receptor, of at least about 30 units of International Standard NIBSC 90/672 per mg, more preferably of at least about 60 units of International Standard NIBSC 90/672 per mg, more preferably of at least about 120 units of International Standard NIBSC 90/672 per mg, or more preferably of at least about 240 units of International Standard NIBSC 90/672 per mg, or one or more fragments thereof.

It may also be even more preferred that such a further binding partner of the present invention, can be characterised by:
- (i) an inhibitory activity with respect to TSH binding to the TSH receptor, of at least about 15 units of International Standard NIBSC 90/672 per mg, more preferably of at least about 30 units of International Standard NIBSC 90/672 per mg, more preferably of at least about 60 units of International Standard NIBSC 90/672 per mg, or more preferably of at least about 120 units of International Standard NIBSC 90/672 per mg; and
- (ii) a stimulatory activity with respect to cAMP production by cells expressing the TSH receptor, of at least about 30 units of International Standard NIBSC 90/672 per mg, more preferably of at least about 60 units of International Standard NIBSC 90/672 per mg, more preferably of at least about 120 units of International Standard NIBSC 90/672 per mg, or even more preferably of at least about 240 units of International Standard NIBSC 90/672 per mg;

or one or more fragments thereof.

A binding partner for the TSH receptor (typically a human monoclonal or recombinant antibody) according to the present invention may have diagnostic and therapeutic applications.

Accordingly, a binding partner for the TSH receptor (typically a human monoclonal or recombinant antibody) according to the present invention can be employed in screening methods for detecting autoantibodies to the TSH receptor in patient sera and also in diagnostic methods. In this way, a binding partner for the TSH receptor (typically a human monoclonal or recombinant antibody) according to the present invention can be employed in place of, or in addition to, competitors hitherto described for use in screening methods for detecting autoantibodies to the TSH receptor and also in diagnostic methods. Similarly, a binding partner for the TSH receptor (typically a human monoclonal or recombinant antibody) according to the present invention can be employed in place of, or in addition to, competitors hitherto described for use in kits for use in detecting autoantibodies to the TSH receptor.

The present invention also provides, therefore, a method of screening for autoantibodies to the TSH receptor in a sample of body fluid obtained from a subject suspected of suffering from, susceptible to, having or recovering from autoimmune disease associated with an immune reaction to a TSH receptor, said method comprising:
- (a) providing said sample of body fluid from said subject;
- (b) providing one or more pairs of binding molecules, wherein a first molecule of said binding pair comprises a binding partner or further binding partner for the TSH receptor (typically a human monoclonal or recombinant antibody) according to the present invention and a second molecule of said binding pair comprises a binding region with which said binding partner or further binding partner interacts;
- (c) contacting said sample with said one or more pairs of binding molecules so as to permit said second molecule of said binding pair to interact with either (i) autoantibodies to the TSH receptor present in said sample, or (ii) said binding partner or further binding partner for the TSH receptor (typically a human monoclonal or recombinant antibody); and
- (d) monitoring the interaction of said second molecule of said binding pair with said autoantibodies present in said sample, thereby providing an indication of the presence of said autoantibodies to the TSH receptor in said sample.

Figure 3A:
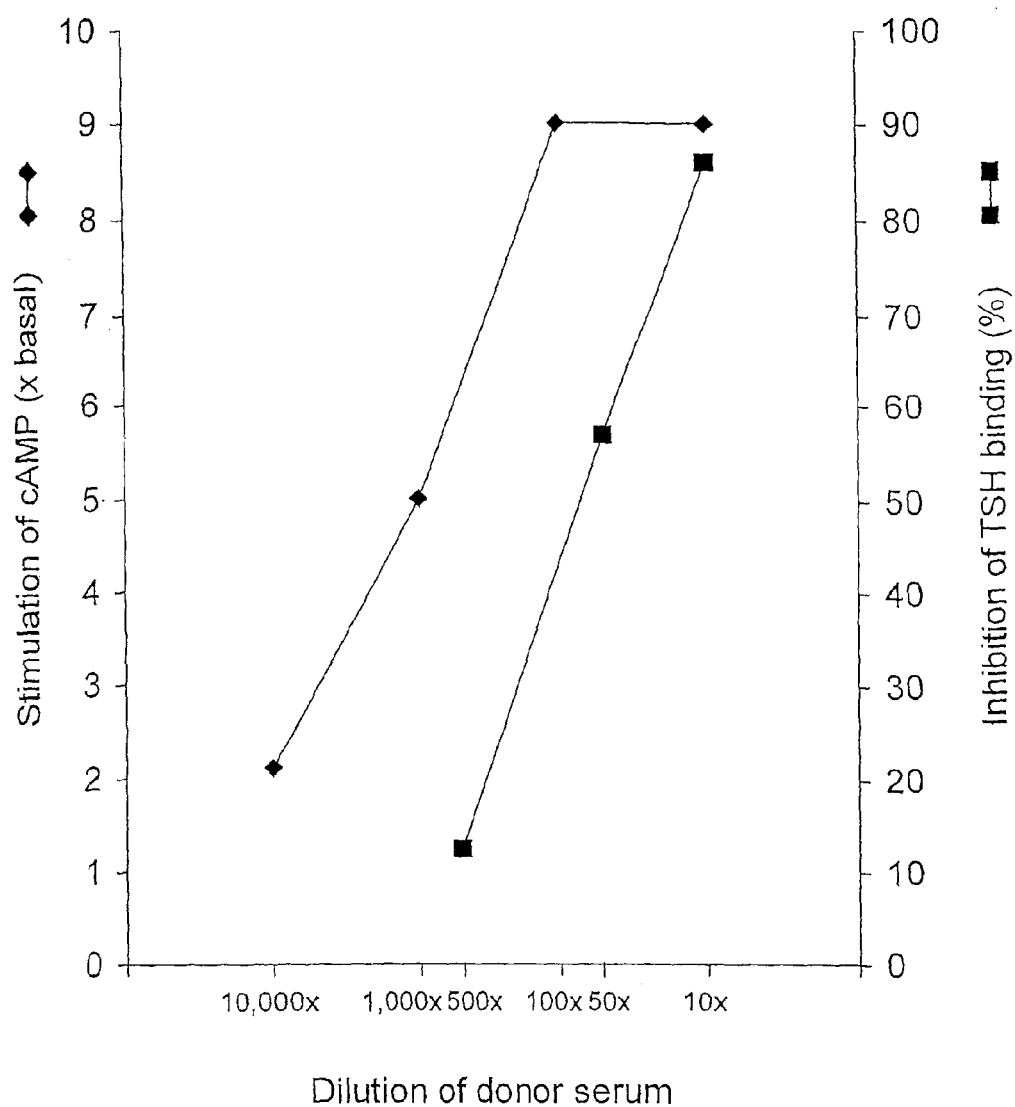
FIG. 3A shows the effect of lymphocyte donor serum on inhibition of TSH binding and on cAMP stimulation in TSH receptor transfected CHO cells. In the case of the binding inhibition assay the serum was diluted in a pool of healthy donor sera. For the stimulation assay, the serum was diluted in NaCl free Hanks Buffered Salt Solution. Healthy blood donor sera (n=3) gave responses ranging from 1.1 to 1.3× basal.
Figure 3B:
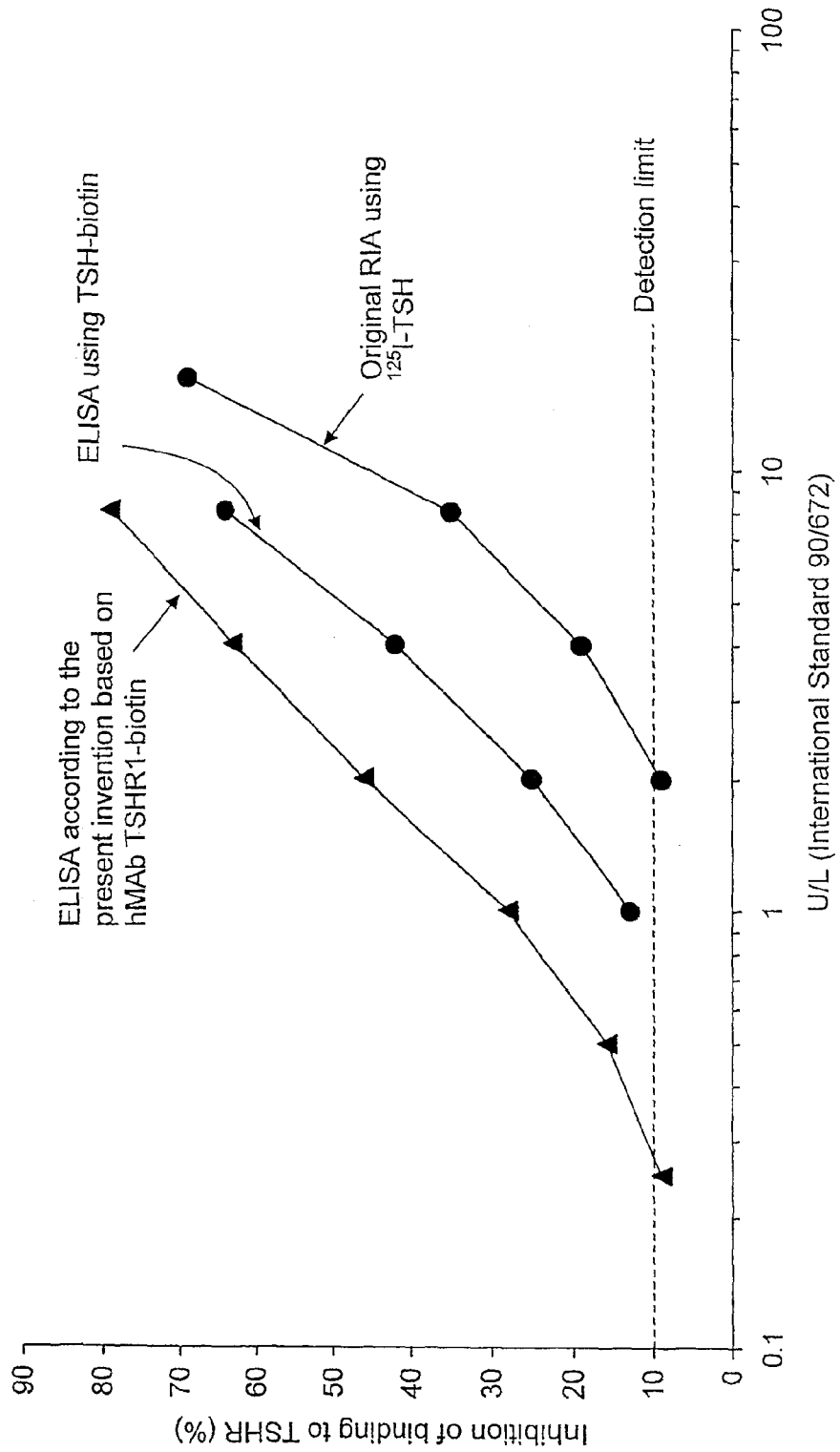
FIG. 3B shows a comparison of an ELISA for TSHR autoantibodies according to the present invention with earlier assays: an ELISA on TSH-biotin described in Bolton et al., Clinical Chemistry (1999) 45: 2285-2287 and the original RIA described by Southgate et al. in Clinical Endocrinology (1984) 20: 539-543.
Figure 3C:
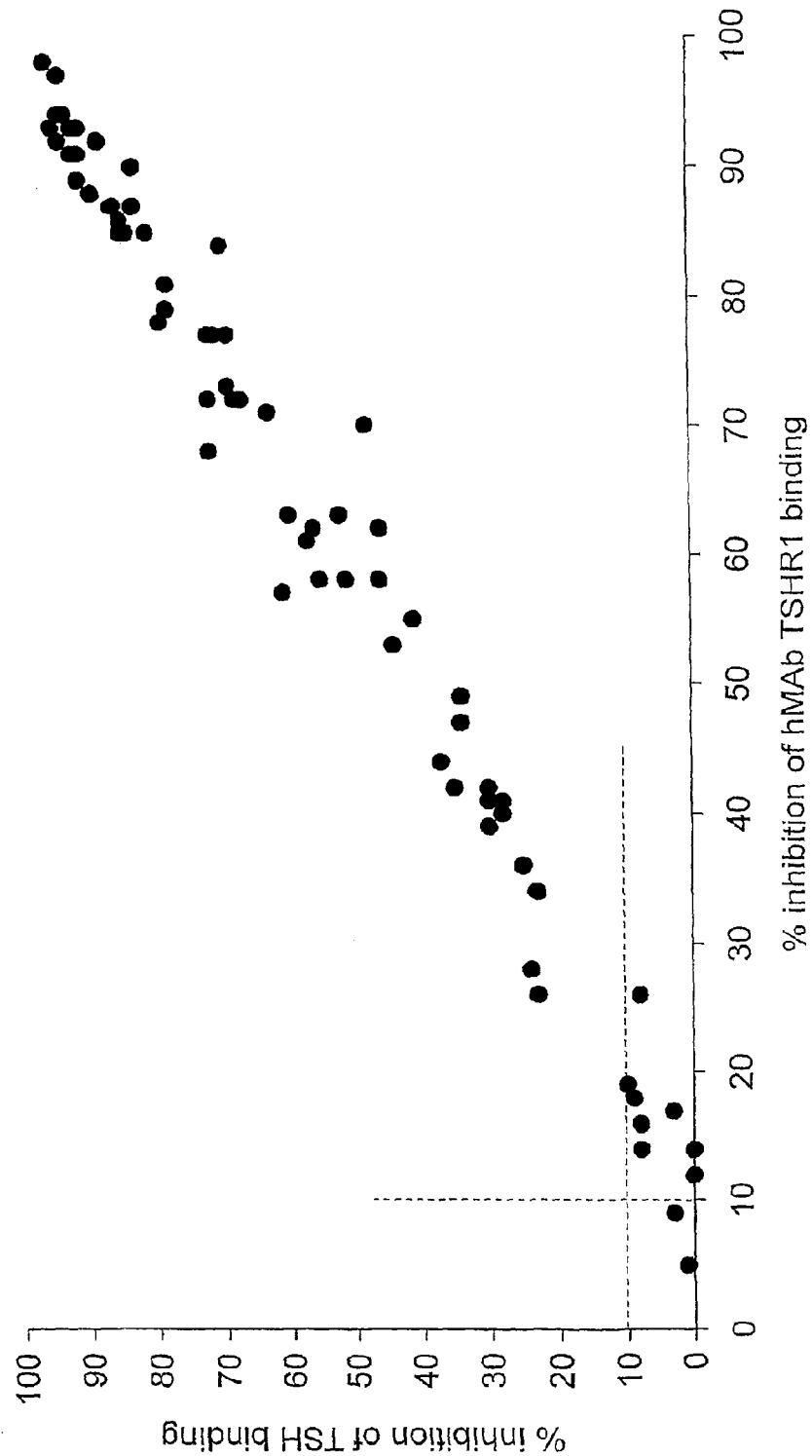
FIG. 3C shows a comparison of an ELISA for TSHR autoantibodies according to the present invention and an ELISA based on TSH biotin as described in Bolton et al., Clinical Chemistry (1999) 45: 2285-2287. Sera from 72 patients with Graves' disease were compared. y=1.1154x−13.032, r=0.99.

A method according to the present invention for the detection of autoantibodies as described above is particularly advantageous in terms of the level of sensitivity that can be achieved by use thereof. This can be further illustrated by reference to the Examples and Figures, where FIG. 3B shows a graphical representation of a comparison between an assay for TSHR autoantibodies based on hMAb TSHR1-biotin and earlier assays. The sensitivity of the assay based on hMAb TSHRI-biotin is clearly superior according to concentration of the international standard NIBSC 90/672 detectable. This was confirmed in a study of sera from 72 patients with Graves' disease shown in FIG. 3C.

There is further provided by the present invention, therefore, a method of screening for autoantibodies to the TSH receptor in a sample of body fluid obtained from a subject suspected of suffering from, susceptible to, having or recovering from autoimmune disease associated with an immune reaction to the TSH receptor, said method comprising:
- (a) providing said sample of body fluid from said subject;
- (b) providing one or more pairs of binding molecules, wherein a first molecule of said binding pair comprises a binding partner or further binding partner for the TSH receptor (typically a human monoclonal or recombinant antibody) according to the present invention and a second molecule of said binding pair comprises a binding region with which said binding partner or further binding partner interacts, wherein the interaction of said binding molecules is such that an autoantibody titer in said sample essentially corresponding to 0.4 U/L of International Standard NIBSC 90/672 is detectable;
- (c) contacting said sample with said one or more pairs of binding molecules so as to permit said second molecule of said binding pair to interact with either (i) autoantibodies to the TSH receptor present in said sample, or (ii) said binding partner or further binding partner for the TSH receptor (typically a human monoclonal or recombinant antibody) according to the present invention; and
- (d) monitoring the interaction of said second molecule of said binding pair with said autoantibodies present in said sample, thereby providing an indication of the presence of said autoantibodies to the TSH receptor in said sample.

The above sensitivity can also be achieved in an assay method or kit according to the present invention by the use of a human or non-human polyclonal antibody to the TSH receptor, TSH or one or more variants, analogs, derivatives or fragments thereof, or a binding partner for the TSH receptor which has an affinity for the TSH receptor of $10^{10}$ molar$^{-1}$ or greater, which generally exhibit a sufficient affinity for the TSH receptor so that a method or kit of the defined sensitivity is provided. The preparation of such polyclonal antibodies, TSH or one or more variants, analogs, derivatives or fragments thereof, is well known in the art. For example, superactive analogs of TSH are described in Nature, Biotechnology, Volume 14, October 1995, pages 1257-1263, although this article does not disclose the use of such superactive TSH in a method or kit as is now provided by the present invention.

There is further provided by the present invention, therefore, a method of screening for autoantibodies to the TSH receptor in a sample of body fluid obtained from a subject suspected of suffering from, susceptible to, having or recovering from autoimmune disease associated with an immune reaction to the TSH receptor, said method comprising:

(a) providing said sample of body fluid from said subject;
(b) providing one or more pairs of binding molecules, wherein a first molecule of said binding pair comprises a human or non-human polyclonal antibody to the TSH receptor and a second molecule of said binding pair comprises a binding region with which said polyclonal antibody interacts, wherein the interaction of said binding molecules is such that an autoantibody titer in said sample essentially corresponding to 0.4 U/L of International Standard NIBSC 90/672 is detectable;
(c) contacting said sample with said one or more pairs of binding molecules so as to permit said second molecule of said binding pair to interact with either (i) autoantibodies to the TSH receptor present in said sample, or (ii) said polyclonal antibody; and
(d) monitoring the interaction of said second molecule of said binding pair with said autoantibodies present in said sample, thereby providing an indication of the presence of said autoantibodies to the TSH receptor in said sample.

There is also provided by the present invention a method of screening for autoantibodies to the TSH receptor in a sample of body fluid obtained from a subject suspected of suffering from, susceptible to, having or recovering from autoimmune disease associated with an immune reaction to the TSH receptor, said method comprising:

(a) providing said sample of body fluid from said subject;
(b) providing one or more pairs of binding molecules, wherein a first molecule of said binding pair comprises TSH or one or more variants, analogs, derivatives or fragments thereof, and a second molecule of said binding pair comprises a binding region with which said TSH or one or more variants, analogs, derivatives or fragments thereof interacts, wherein the interaction of said binding molecules is such that an autoantibody titer in said sample essentially corresponding to 0.4 U/L of International Standard NIBSC 90/672 is detectable;
(c) contacting said sample with said one or more pairs of binding molecules so as to permit said second molecule of said binding pair to interact with either (i) autoantibodies to the TSH receptor present in said sample, or (ii) said TSH or one or more variants, analogs, derivatives or fragments thereof; and
(d) monitoring the interaction of said second molecule of said binding pair with said autoantibodies present in said sample, thereby providing an indication of the presence of said autoantibodies to the TSH receptor in said sample.

There is also still further provided a method of screening for autoantibodies to the TSH receptor in a sample of body fluid obtained from a subject suspected of suffering from, susceptible to, having or recovering from autoimmune disease associated with an immune reaction to the TSH receptor, said method comprising:

(a) providing said sample of body fluid from said subject;
(b) providing one or more pairs of binding molecules, wherein a first molecule of said binding pair comprises a binding partner for the TSH receptor which has an affinity for the TSH receptor of $10^{10}$ molar$^{-1}$ or greater and a second molecule of said binding pair comprises a binding region with which said binding partner interacts, wherein the interaction of said binding molecules is such that an autoantibody titer in said sample essentially corresponding to 0.4 U/L of International Standard NIBSC 90/672 is detectable;
(c) contacting said sample with said one or more pairs of binding molecules so as to permit said second molecule of said binding pair to interact with either (i) autoantibodies to the TSH receptor present in said sample, or (ii) said binding partner for the TSH; and
(d) monitoring the interaction of said second molecule of said binding pair with said autoantibodies present in said sample, thereby providing an indication of the presence of said autoantibodies to the TSH receptor in said sample.

There is also provided by the present invention use of a binding partner or further binding partner for the TSH receptor (typically a human monoclonal or recombinant antibody) according to the present invention, for detecting autoantibodies to the TSH receptor in a sample of body fluid obtained from a subject suspected of suffering from, susceptible to, having or recovering from autoimmune disease associated with an immune reaction to the TSH receptor, wherein the interaction of said binding partner or further binding partner with the TSH receptor is such that an autoantibody titer in said sample essentially corresponding to 0.4 U/L of International Standard NIBSC 90/672 is detectable.

There is also provided use of a human or non-human polyclonal antibody to the TSH receptor, for detecting autoantibodies to the TSH receptor in a sample of body fluid obtained from a subject suspected of suffering from, susceptible to, having or recovering from autoimmune disease associated with an immune reaction to the TSH receptor, wherein the interaction of said polyclonal antibody with the TSH receptor is such that an autoantibody titer in said sample essentially corresponding to 0.4 U/L of International Standard NIBSC 90/672 is detectable.

There is also provided use of TSH or one or more variants, analogs, derivatives or fragments thereof, for detecting autoantibodies to the TSH receptor in a sample of body fluid obtained from a subject suspected of suffering from, susceptible to, having or recovering from autoimmune disease associated with an immune reaction to the TSH receptor, wherein the interaction of said TSH or one or more variants, analogs, derivatives or fragments thereof with the TSH receptor is such that an autoantibody titer in said sample essentially corresponding to 0.4 U/L of International Standard NIBSC 90/672 is detectable.

There is still further provided use of a binding partner for the TSH receptor which has an affinity for the TSH receptor of $10^{10}$ molar$^{-1}$ or greater, for detecting autoantibodies to the TSH receptor in a sample of body fluid obtained from a subject suspected of suffering from, susceptible to, having or recovering from autoimmune disease associated with an immune reaction to the TSH receptor, wherein the interaction of said binding partner with the TSH receptor is such that an autoantibody titer in said sample essentially corresponding to 0.4 U/L of International Standard NIBSC 90/672 is detectable.

It will be appreciated that binding molecules of the one or more binding pairs can be antigen-antibody (for example, [TSH receptor or epitope]-[monoclonal or recombinant TSH receptor antibody]), anti-idiotypic antibody-monoclonal or recombinant TSH receptor antibody or novel TSH receptor antibody binding member-monoclonal or recombinant TSH receptor antibody. Preferably, the binding molecules of the binding pairs are antigen-antibody, namely, [TSH receptor or one or more epitopes thereof]-[monoclonal or recombinant TSH receptor antibody], where the epitopes may be "free standing" or present in a larger scaffold polypeptide or the like.

Preferably, the present invention provides a method of screening for autoantibodies to the TSH receptor in a sample of body fluid obtained from a subject suspected of suffering from, susceptible to, having or recovering from autoimmune disease associated with an immune reaction to a TSH receptor, said method comprising:

(a) providing said sample of body fluid from said subject;
(b) contacting said sample with (i) a full length TSH receptor, or one or more epitopes thereof or a polypeptide comprising one or more epitopes of a TSH receptor, and (ii) a binding partner or further binding partner for the TSH receptor (typically a human monoclonal or recombinant antibody) according to the present invention, under conditions that allow interaction of the TSH receptor with autoantibodies produced in response to the TSH receptor, so as to permit said TSH receptor, or said one or more epitopes thereof or said polypeptide, to interact with either autoantibodies to the TSH receptor present in said sample, or said binding partner or further binding partner for the TSH receptor (typically a human monoclonal or recombinant antibody); and
(c) monitoring the interaction of said TSH receptor, or said one or more epitopes thereof or said polypeptide, with said autoantibodies present in said sample, thereby providing an indication of the presence of said autoantibodies to the TSH receptor in said sample.

In certain embodiments, a method according to the present invention may also employ one or more competitors that compete in the interaction of a polyclonal antibody, TSH or one or more variants, analogs, derivatives or fragments thereof, or a binding partner or further binding partner for the TSH receptor substantially as described above in the specific embodiments of methods as provided by the present invention and the second molecule of the binding pair, or the TSH receptor, or the one or more epitopes thereof or the polypeptide. Such competitors may comprise TSH, or one or more monoclonals reactive with the TSH receptor, such as mouse monoclonals reactive with the TSH receptor.

Preferably, a method according to the present invention as referred to above, further comprises providing labelling means for a binding partner or further binding partner for the TSH receptor (typically a human monoclonal or recombinant antibody) according to the present invention and where appropriate one or more competitors as described above, suitable labelling means including enzymic labels, isotopic labels, chemiluminescent labels, fluorescent labels, dyes and the like.

The present invention also provides, a kit for screening for autoantibodies to the TSH receptor in a sample of body fluid obtained from a subject suspected of suffering from, susceptible to, having or recovering from autoimmune disease associated with an immune reaction to a TSH receptor, said kit comprising:

(a) one or more pairs of binding molecules, wherein a first molecule of said binding pair comprises a binding partner or further binding partner for the TSH receptor (typically a human monoclonal or recombinant antibody) according to the present invention and a second molecule of said binding pair comprises a binding region with which said binding partner or further binding partner interacts;
(b) means for contacting said sample of body fluid from said subject with said one or more pairs of binding molecules so as to permit said second molecule of said binding pair to interact with either (i) autoantibodies to the TSH receptor present in said sample, or (ii) said binding partner or further binding partner for the TSH receptor (typically a human monoclonal or recombinant antibody); and
(c) means for monitoring the interaction of said second molecule of said binding pair with said autoantibodies present in said sample, thereby providing an indication of the presence of said autoantibodies to the TSH receptor in said sample.

The present invention also provides a kit for screening for autoantibodies to the TSH receptor in a sample of body fluid obtained from a subject suspected of suffering from, susceptible to, having or recovering from autoimmune disease associated with an immune reaction to the TSH receptor, said kit comprising:

(a) one or more pairs of binding molecules, wherein a first molecule of said binding pair comprises a binding partner or further binding partner for the TSH receptor (typically a human monoclonal or recombinant antibody) according to the present invention and a second molecule of said binding pair comprises a binding region with which said binding partner or further binding partner interacts, wherein the interaction of said binding molecules is such that an autoantibody titer in said sample essentially corresponding to 0.4 U/L of International Standard NIBSC 90/672 is detectable;
(b) means for contacting said sample of body fluid from said subject with said one or more pairs of binding molecules so as to permit said second molecule of said binding pair to interact with either (i) autoantibodies to the TSH receptor present in said sample, or (ii) said binding partner or further binding partner for the TSH receptor (typically a human monoclonal or recombinant antibody) according to the present invention; and
(c) means for monitoring the interaction of said second molecule of said binding pair with said autoantibodies present in said sample, thereby providing an indication of the presence of said autoantibodies to the TSH receptor in said sample.

There is also provided a kit for screening for autoantibodies to the TSH receptor in a sample of body fluid obtained from a subject suspected of suffering from, susceptible to, having or recovering from autoimmune disease associated with an immune reaction to the TSH receptor, said kit comprising:

(a) one or more pairs of binding molecules, wherein a first molecule of said binding pair comprises a human or non-human polyclonal antibody to the TSH receptor and a second molecule of said binding pair comprises a binding region with which said polyclonal antibody interacts, wherein the interaction of said binding molecules is such that an autoantibody titer in said sample essentially corresponding to 0.4 U/L of International Standard NIBSC 90/672 is detectable;
(b) means for contacting said sample of body fluid from said subject with said one or more pairs of binding molecules so as to permit said second molecule of said binding pair to interact with either (i) autoantibodies to the TSH receptor present, in said sample, or (ii) said polyclonal antibody; and
(c) means for monitoring the interaction of said second molecule of said binding pair with said autoantibodies present in said sample, thereby providing an indication of the presence of said autoantibodies to the TSH receptor in said sample.

There is also provided a kit for screening for autoantibodies to the TSH receptor in a sample of body fluid obtained from a subject suspected of suffering from, susceptible to, having or recovering from autoimmune disease associated with an immune reaction to the TSH receptor, said kit comprising:
  (a) one or more pairs of binding molecules, wherein a first molecule of said binding pair comprises TSH or one or more variants, analogs, derivatives or fragments thereof, and a second molecule of said binding pair comprises a binding region with which said TSH or one or more variants, analogs, derivatives or fragments thereof interacts, wherein the interaction of said binding molecules is such that an autoantibody titer in said sample essentially corresponding to 0.4 U/L of International Standard NIBSC 90/672 is detectable;
  (b) means for contacting said sample of body fluid from said subject with said one or more pairs of binding molecules so as to permit said second molecule of said binding pair to interact with either (i) autoantibodies to the TSH receptor present in said sample, or (ii) TSH or one or more variants, analogs, derivatives or fragments thereof; and
  (c) means for monitoring the interaction of said second molecule of said binding pair with said autoantibodies present in said sample, thereby providing an indication of the presence of said autoantibodies to the TSH receptor in said sample.

There is also provided a kit for screening for autoantibodies to the TSH receptor in a sample of body fluid obtained from a subject suspected of suffering from, susceptible to, having or recovering from autoimmune disease associated with an immune reaction to the TSH receptor, said kit comprising:
  (a) one or more pairs of binding molecules, wherein a first molecule of said binding pair comprises a binding partner for the TSH receptor which has an affinity for the TSH receptor of $10^{10}$ molar$^{-1}$ or greater and a second molecule of said binding pair comprises a binding region with which said binding partner interacts, wherein the interaction of said binding molecules is such that an autoantibody titer in said sample essentially corresponding to 0.4 U/L of International Standard NIBSC 90/672 is detectable;
  (b) means for contacting said sample of body fluid from said subject with said one or more pairs of binding molecules so as to permit said second molecule of said binding pair to interact with either (i) autoantibodies to the TSH receptor present in said sample, or (ii) said binding partner for the TSH receptor; and
  (c) means for monitoring the interaction of said second molecule of said binding pair with said autoantibodies present in said sample, thereby providing an indication of the presence of said autoantibodies to the TSH receptor in said sample.

It will be appreciated that binding molecules of the one or more binding pairs can be antigen-antibody (for example, [TSH receptor or epitope]-[monoclonal or recombinant TSH receptor antibody]), anti-idiotypic antibody-monoclonal or recombinant TSH receptor antibody or novel TSH receptor antibody binding member-monoclonal or recombinant TSH receptor antibody. Preferably, the binding molecules of the binding pairs are antigen-antibody, namely, [TSH receptor or one or more epitopes thereof]-[monoclonal or recombinant TSH receptor antibody], where the epitopes may be "free standing" or present in a larger scaffold polypeptide or the like.

The present invention preferably provides a kit for screening for autoantibodies to the TSH receptor in a sample of body fluid obtained from a subject suspected of suffering from, susceptible to, having or recovering from autoimmune disease associated with an immune reaction to the TSH receptor, said kit comprising:
  (a) a full length TSH receptor, or one or more epitopes thereof or a polypeptide comprising one or more epitopes of the TSH receptor;
  (b) a binding partner or further binding partner for the TSH receptor (typically a human monoclonal or recombinant antibody) according to the present invention;
  (c) means for contacting said sample of body fluid from said subject, said TSH receptor, or said one or more epitopes thereof or said polypeptide, and said binding partner or further binding partner for the TSH receptor (typically a human monoclonal or recombinant antibody), under conditions that allow interaction of the TSH receptor with autoantibodies produced in response to the TSH receptor, so as to permit said TSH receptor, or said one or more epitopes thereof or said polypeptide, to interact with either autoantibodies to a TSH receptor present in said sample, or said binding partner or further binding partner for the TSH receptor (typically a human monoclonal or recombinant antibody); and
  (d) means for monitoring the interaction of said TSH receptor, or said one or more epitopes thereof or said polypeptide, with said autoantibodies present in said sample, thereby providing an indication of the presence of said autoantibodies to the TSH receptor in said sample.

In certain embodiments, a kit according to the present invention may further comprise one or more competitors that compete in the interaction of a polyclonal antibody, TSH or one or more variants, analogs, derivatives or fragments thereof, or a binding partner or further binding partner for the TSH receptor, as respectively defined above, and the second molecule of the binding pair, or the TSH receptor, or the one or more epitopes thereof or the polypeptide. Such competitors may comprise TSH, or one or more monoclonals reactive with the TSH receptor, such as mouse monoclonals reactive with the TSH receptor.

Suitably, a kit as referred to above further comprises labelling means for a binding partner or further binding partner for the TSH receptor (typically a human monoclonal or recombinant antibody) according to the present invention and where appropriate one or more competitors as described above, suitable labelling means being substantially as hereinbefore described.

In the presence of autoantibodies to the TSH receptor, binding of the TSH receptor to a binding partner for the TSH receptor (typically a human monoclonal or recombinant antibody) in a method or kit as described above will be decreased.

A binding partner or further binding partner for the TSH receptor (typically a human monoclonal or recombinant antibody) according to the present invention can also be employed in assay methods and kits substantially as described above for TSH and related ligands.

The present invention also provides, therefore, a method of assaying TSH and related ligands, said method comprising:
  (a) providing a sample suspected of containing or containing TSH or related ligands;
  (b) providing one or more pairs of binding molecules, wherein a first molecule of said binding pair comprises a binding partner or further binding partner for the TSH receptor (typically a human monoclonal or recombinant antibody) according to the present invention and a second molecule of said binding pair comprises a binding region with which said binding partner or further binding partner interacts;

(c) contacting said sample with said one or more pairs of binding molecules so as to permit said second molecule of said binding pair to interact with either (i) TSH or related ligands present in said sample, or (ii) said binding partner or further binding partner for the TSH receptor (typically a human monoclonal or recombinant antibody); and (d) monitoring the interaction of said second molecule of said binding pair with TSH or related ligands present in said sample, thereby providing an indication of the presence of TSH or related ligands in said sample.

The present invention also provides a kit for assaying TSH or related ligands, said kit comprising:
(a) one or more pairs of binding molecules, wherein a first molecule of said binding pair comprises a binding partner or further binding partner for the TSH receptor (typically a human monoclonal or recombinant antibody) according to the present invention and a second molecule of said binding pair comprises a binding region with which said binding partner or further binding partner interacts;
(b) means for contacting a sample suspected of containing or containing TSH or related ligands with said one or more pairs of binding molecules so as to permit said second molecule of said binding pair to interact with either (i) TSH or related ligands present in said sample, or (ii) said binding partner or further binding partner for the TSH receptor (typically a human monoclonal or recombinant antibody); and
(c) means for monitoring the interaction of said second molecule of said binding pair with TSH or related ligands present in said sample, thereby providing an indication of the presence of TSH or related ligands in said sample.

The present invention also further provides a method of identifying a further binding partner for the TSH receptor, which further binding partner is capable of binding to the TSH receptor and which competes for binding to the TSH receptor with a binding partner for the TSH receptor substantially as hereinbefore described, which further binding partner does not comprise TSH, which method comprises:
(a) providing one or more pairs of binding molecules, wherein a first molecule of said binding pair comprises a binding partner for the TSH receptor substantially as hereinbefore described and a second molecule of said binding pair comprises a binding region with which said binding partner interacts;
(b) providing a further binding molecule to be assayed as a potential further binding partner for the TSH receptor which competes for binding to the TSH receptor with said first molecule of said binding pair of (a);
(c) contacting said further binding molecule of (b) with said one or more pairs of binding molecules of (a) so as to permit said second molecule of said binding pair of (a) to interact with either (i) said further binding molecule of (b), or (ii) said first molecule of said binding pair of (a); and
(d) monitoring the interaction of said second molecule of said binding pair of (a) with said further binding molecule of (b), and thereby assessing whether said further binding molecule of (b) competes for binding to the TSH receptor with said first molecule of said binding pair of (a).

The present invention also provides a kit for identifying a further binding partner for the TSH receptor, which further binding partner is capable of binding to the TSH receptor and which competes for binding to the TSH receptor with a binding partner for the TSH receptor substantially as hereinbefore described, which further binding partner does not comprise TSH, which kit comprises:
(a) one or more pairs of binding molecules, wherein a first molecule of said binding pair comprises a binding partner for the TSH receptor substantially as hereinbefore described and a second molecule of said binding pair comprises a binding region with which said binding partner interacts;
(b) means for contacting said one or more pairs of binding molecules of (a) with a further binding molecule to be assayed as a potential further binding partner for the TSH receptor which competes for binding to the TSH receptor with said first molecule of said binding pair of (a), so as to permit said second molecule of said binding pair of (a) to interact with either (i) said further binding molecule, or (ii) said first molecule of said binding pair of (a); and
(c) means for monitoring the interaction of said second molecule of said binding pair of (a) with said further binding molecule, and thereby assessing whether said further binding molecule competes for binding to the TSH receptor with said first molecule of said binding pair of (a).

A further application of a binding partner or further binding partner for the TSH receptor (typically a human monoclonal or recombinant antibody) according to the present invention is its use to identify and provide new types of TSH receptor antibody binding sites. There is further provided by the present invention, therefore, a process of identifying one or more epitope regions of the TSH receptor, which process comprises contacting a binding partner or further binding partner for the TSH receptor (typically a human monoclonal or recombinant antibody) substantially as hereinbefore described with a full length TSH receptor, or one or more fragments thereof, so as to allow interaction of said binding partner or further binding partner for the TSH receptor with said full length TSH receptor, or said one or more fragments thereof, and identifying the amino acids of said full length TSH receptor, or said one or more fragments thereof, with which said binding partner or further binding partner interacts. Suitably, interaction of the binding partner or further binding partner with selected fragments of the TSH receptor and the full length TSH receptor, is analysed, so as to identify the amino acids of the TSH receptor with which the binding partner interacts.

Furthermore, the present invention allows for generation of antibodies to the regions of a monoclonal TSH receptor antibody according to the present invention which bind the TSH receptor. Such anti-idiotypic antibodies produced in this way could have potential as new ligands for assays of TSH receptor autoantibodies, TSH and related compounds. Also they may be effective agents in vivo for regulating the action of TSH receptor autoantibodies, TSH and related compounds. The present invention further provides, therefore, one or more anti-idiotypic antibodies generated to binding regions of a binding partner or further binding partner for the TSH receptor (typically a human monoclonal or recombinant antibody) substantially as hereinbefore described, and the preparation thereof is further described by the Examples.

Other methods of identifying and providing new types of antibody binding sites using monoclonal antibodies are well known. For example by antibody screening of phage-displayed random peptide libraries as described by J C Scott and G P Smith; "Searching for peptide ligands with an epitope library"; Science 1990; 249 (4967): 386-390 and MA Myers, J M Davies, J C Tong, J Whisstock, M Scealy, I R MacKay, M J Rowley; "Conformational epitopes on the diabetes autoantigen $GAD_{65}$ identified by peptide phage display and molecular modelling"; Journal of Immunology 2000; 165: 3830-3838. Antibody screening of non-peptide compounds and libraries of non-peptide compounds can also be carried out.

New types of TSH receptor antibody binding sites identified and provided using these procedures may also be useful as new ligands in assays for TSH receptor autoantibodies, TSH and related compounds. Furthermore they may be effective agents in vivo for regulating the action of TSH receptor autoantibodies, TSH and related compounds.

A binding partner for the TSH receptor or further binding partner (typically a human monoclonal or recombinant antibody) according to the present invention substantially as hereinbefore described can also be usefully employed in therapy. There is, therefore, further provided by the present invention methods of treatment comprising administration of a binding partner or further binding partner for the TSH receptor (typically a human monoclonal or recombinant antibody) substantially as hereinbefore described, pharmaceutical compositions comprising a binding partner or further binding partner for the TSH receptor (typically a human monoclonal or recombinant antibody) substantially as hereinbefore described (together with one or more pharmaceutically acceptable carriers, diluents or excipients therefor), and use of a binding partner or further binding partner for the TSH receptor (typically a human monoclonal or recombinant antibody) substantially as hereinbefore described in the manufacture of a medicament or composition.

A binding partner for the TSH receptor, in particular a human monoclonal antibody to the TSH receptor derived from patients' lymphocytes according to the present invention, is a valuable reagent for understanding the pathogenesis of Graves' disease and for developing new methods of measuring TSH receptor autoantibodies, for example as replacements for TSH in competitive binding assays substantially as hereinbefore described. Also, a stimulating binding partner according to the present invention has in vivo applications when tissue containing the TSH receptor (eg thyroid tissue or thyroid cancer tissue) requires stimulation. The present invention provides, therefore, a medicament or composition for use in stimulating thyroid tissue, and/or tissue containing the TSH receptor. In particular, a stimulating binding partner for the TSH receptor (typically a human monoclonal or recombinant antibody) according to the present invention can be employed in oncology, and in particular for use in the diagnosis, management and treatment of thyroid cancer.

Alternatively, a binding partner or further binding partner for the TSH receptor according to the present invention can be a powerful TSH or autoantibody antagonist (blocking antibody) and such a blocking TSH receptor antibody according to the present invention is valuable for in vivo applications when the activity of tissue containing the TSH receptor (eg thyroid tissue or thyroid cancer tissue) requires inactivation or to be made unresponsive to TSH, TSH receptor autoantibodies or other stimulators.

There is also provided in combination, a binding partner or further binding partner for the TSH receptor substantially as hereinbefore described, together with one or more further agents capable of inactivating or rendering unresponsive, tissue containing a TSH receptor, to TSH, TSH receptor autoantibodies or other stimulators. Typically, the one or more further agents act independently of the TSH receptor.

A particular therapeutic application where TSH receptor autoantibody binding requires inactivation or inhibition is in the treatment of disease of the retro orbital tissues of the eye associated with autoimmunity to the TSH receptor, and the use of a blocking antibody which interacts with the TSH receptor, such as 9D33, so as to inhibit TSH receptor autoantibody binding, thus has important therapeutic utility in the treatment of such disease. Treatment of autoimmune disease which requires inhibition of TSH receptor autoantibody binding, such as the above discussed disease of the retro orbital tissues of the eye associated with autoimmunity to the TSH receptor, may alternatively employ an anti-idiotypic antibody to a binding partner or further binding partner as provided by the present invention, and such anti-idiotypic antibodies form a further aspect of the present invention as described herein and further preparatory details thereof are provided by the Examples.

More specifically, therefore, the present invention provides use in the treatment of disease of the retro orbital tissues of the eye associated with autoimmunity to the TSH receptor, of a further binding partner to the TSH receptor, which further binding partner substantially inhibits binding to the TSH receptor of a binding partner for the TSH receptor (typically a human monoclonal or recombinant antibody) substantially as hereinbefore described. The present invention further provides use in the manufacture of a medicament for the treatment of disease of the retro orbital tissues of the eye associated with activation and/or stimulation of the TSH receptor, of a further binding partner to the TSH receptor, which further binding partner substantially inhibits binding to the TSH receptor of a binding partner for the TSH receptor (typically a human monoclonal or recombinant antibody) substantially as hereinbefore described. There is also provided a method of treating disease of the retro orbital tissues of the eye associated with autoimmunity to the TSH receptor, which method comprises administration to a patient suffering from or susceptible to such disease a therapeutically effective amount of a further binding partner to the TSH receptor, which further binding partner substantially inhibits binding to the TSH receptor of a binding partner for the TSH receptor (typically a human monoclonal or recombinant antibody) substantially as hereinbefore described. A further binding partner for use in these embodiments of the present invention preferably comprises a blocking antibody which can substantially inhibit binding of a binding partner as provided by the present invention, and as such TSH receptor autoantibody binding, to the TSH receptor, and a preferred such antibody can comprise 9D33 as described herein.

The present invention also provides use of an anti-idiotypic antibody generated to a binding region of a binding partner or further binding partner according to the present invention, in the treatment of disease of the retro orbital tissues of the eye associated with autoimmunity to the TSH receptor. The present invention further provides use of an anti-idiotypic antibody generated to a binding region of a binding partner or further binding partner according to the present invention, in the manufacture of a medicament for the treatment of disease of the retro orbital tissues of the eye associated with activation and/or stimulation of the TSH receptor. There is also provided a method of treating disease of the retro orbital tissues of the eye associated with autoimmunity to the TSH receptor, which method comprises administration to a patient suffering from or susceptible to such disease a therapeutically effective amount of an anti-idiotypic antibody generated to a binding region of a binding partner or further binding partner according to the present invention.

One of the major advantages of a monoclonal antibody as provided by the present invention over TSH in such in vitro and/or in vivo applications is the relative ease with which such antibodies can be manipulated. For example, manipulation of the TSH receptor binding region of a monoclonal antibody according to the present invention so as to change the characteristics thereof, such as affinity and biological characteristics, including the degree of TSH agonist or antagonist activities. Also monoclonal antibodies according to the present invention have a much longer half life than TSH in vivo and this may have considerable advantages in in vivo applications. Furthermore, the half life of the antibodies can be manipulated, for example antibody Fab fragments have a much shorter half life than intact IgG.

Pharmaceutical compositions according to the present invention include those suitable for oral, parenteral and topical administration, although the most suitable route will generally depend upon the condition of a patient and the specific disease being treated. The precise amount of a binding partner or further binding partner for the TSH receptor (typically a human monoclonal or recombinant antibody) substantially as hereinbefore described to be administered to a patient will be the responsibility of an attendant physician, although the dose employed will depend upon a number of factors, including the age and sex of the patient, the specific disease being treated and the route of administration substantially as described above.

There is further provided by the present invention a method of stimulating thyroid tissue, and/or tissue containing a TSH receptor, which method comprises administering to a patient in need of such stimulation a diagnostically or therapeutically effective, amount of a binding partner or further binding partner for the TSH receptor (typically a human monoclonal or recombinant antibody) substantially as hereinbefore described.

The present invention also provides in combination, a binding partner for the TSH receptor (typically a human monoclonal or recombinant antibody) substantially as hereinbefore described, together with one or more further agents capable of stimulating thyroid tissue, and/or tissue containing a TSH receptor, for simultaneous, separate or sequential use in stimulating thyroid tissue, and/or tissue containing a TSH receptor. Preferably the one or more further agents comprise recombinant human TSH and/or one or more variants, analogs, derivatives or fragments thereof, or variants, analogs or derivatives of such fragments. Alternatively, the one or more further agents can act independently of binding to the TSH receptor.

A binding partner for the TSH receptor or further binding partner (typically a human monoclonal or recombinant antibody) according to the present invention can also be employed as a replacement source for patient serum required to contain TSH receptor antibody or antibodies for use in commercial kits. Furthermore, a binding partner or further binding partner for the TSH receptor (typically a human monoclonal or recombinant antibody) can be provided according to the present invention in a preparation required to comprise a defined concentration of TSH receptor antibody or antibodies, and in this way there can be provided a preparation with a defined activity, such as stimulatory activity, with respect to the TSH receptor. Optionally, such a preparation may further comprise one or more further human monoclonal antibodies, such as monoclonal antibodies to GAD, TPO or the like.

The following illustrative explanations are provided to facilitate understanding of certain terms used herein. The explanations are provided as a convenience and are not limitative of the invention BINDING PARTNER FOR A TSH RECEPTOR, describes a molecule having a binding specificity for the TSH receptor. A binding partner as described herein may be naturally derived or wholly or partially synthetically produced. Such a binding partner has a domain or region which specifically binds to and is therefore complementary to one or more epitope regions of the TSH receptor. In particular, a binding partner as described herein can be a monoclonal or recombinant antibody to the TSH receptor, and more particularly can be a human monoclonal or recombinant antibody to the TSH receptor.

C DOMAIN denotes a region of relatively constant amino acid sequence in antibody molecules.

CDR denotes complementarity determining regions which are present on both heavy and light chains of antibody molecules and represent regions of most sequence variability. CDRs represent approximately 15 to 20% of variable domains and represent antigen binding sites of an antibody.

FR denotes framework regions and represent the remainder of the variable light domains and variable heavy domains not present in CDRs.

HC denotes part of a heavy chain of an antibody molecule comprising the heavy chain variable domain and the first domain of an IgG constant region.

HOST CELL is a cell which has been transformed or transfected, or is capable of transformation or transfection by an exogenous polynucleotide sequence.

IDENTITY, as known in the art, is the relationship between two or more polypeptide sequences, or two or more polynucleotide sequences, as determined by comparing the sequences.

LC denotes a light chain of an antibody molecule.

NIBSC 90/672 is, an International Standard for thyroid stimulating antibody. The International Standard for thyroid stimulating activity consists of a batch of ampoules containing freeze dried plasma proteins from a single human patient with high TSH receptor autoantibodies. The preparation has been evaluated in an international collaborative study and shown to possess both thyroid stimulating and thyroid receptor binding activity. At the $46^{th}$ meeting in 1995, the Expert Committee on Biological Standardization of WHO established the preparation coded 90/672 as the International Standard for thyroid stimulating antibody. Each ampoule contains freeze-dried residue of 1.0 ml of a solution containing 0.02M phosphate buffer, dialysed human plasma proteins and 0.1 International Units (100 milli-International Units) per ampoule by definition.

STIMULATION OF A TSH RECEPTOR by a human monoclonal antibody as described herein denotes the ability thereof to bind to a TSH receptor and to thereby effect, for example, production of cyclic AMP as a result of such binding to the TSH receptor. Such stimulation is analogous to the responses seen on binding of TSH, or TSH receptor autoantibodies, to the TSH receptor and in this way a human monoclonal antibody as described herein essentially provides the same or similar binding responses as seen with TSH, or TSH receptor autoantibody, binding to a TSH receptor.

V DOMAIN denotes a region of highly variable amino acid sequence in antibody molecules.

$V_H$ DOMAIN denotes variable regions or domains in heavy chains of antibody molecules.

$V_L$ DOMAIN denotes variable regions or domains in light chains of antibody molecules.

The present invention will now be illustrated by the following Figures and Examples, which do not limit the scope of the invention in any way.

EXAMPLES

Materials & Methods

Lymphocyte Isolation and Cloning of Human Monoclonal TSH Receptor Autoantibodies Blood was obtained from a patient with Graves' disease and Type 1 diabetes mellitus who had high levels of serum autoantibodies to the TSH receptor (TRAb). Ethical Committee approval was obtained for the studies. Peripheral blood lymphocytes were isolated on Ficoll-Paque (Amersham Biosciences; Chalfont St Giles, HPS 4SP, UK) from a 20 mL blood sample and then infected with Epstein Barr virus (EBV) (European Collection of Cell Cultures-ECACC; Porton Down, SP4 OJG, UK) and cultured on mouse macrophage feeder layers as described before (N Hayakawa, L D K E Premawardhana, M Powell, M Masuda, C Arnold, J Sanders, M Evans, S Chen, J C Jaume, S Baekkeskov, B Rees Smith, J Furmaniak; "Isolation and characterization of human monoclonal autoantibodies to glutamic acid decarboxylase"; Autoimmunity 2002; 35: 343-355). EBV immortalised B lymphocytes were then fused with the mouse/human hybrid cell line K6H6/B5 (W L Carroll, K Thilemans, J Dilley, R Levy; "Mouse x human heterohybridomas as fusion partners with human B cell tumors"; Journal of Immunological Methods 1986; 89: 61-72) and cloned two times by limiting dilution at 5 cells/well and a final time at ½ cell/well to obtain a single colony (B J Bolton, N K Spurr. "B-lymphocytes" In: R I Freshney, M G Freshney (eds). Culture of immortalized cells. Wiley-Liss, New York 1996; 283-297). The original wells and subsequent clones were screened for TSH receptor autoantibody by inhibition of $^{125}$I-TSH binding to solubilised TSH receptor (see below). The single clones producing TSH receptor autoantibodies were grown up in tissue culture flasks.

Production, Purification and Labelling of Monoclonal TSH Receptor Antibody Preparations Mouse TSH receptor MAbs were produced as described before (Y Oda, J Sanders, M Evans, A Kiddie, A Munkley, C James, T Richards, J Wills, J Furmaniak, B Rees Smith; "Epitope analysis of the human thyrotropin (TSH) receptor using monoclonal antibodies"; Thyroid 2000; 10: 1051-1059) and were also prepared from mice immunised with full length TSHR cDNA cloned in pcDNA3.1 (U A Hasan, A M Abai, D R Harper, B W Wren, W J W Morrow; "Nucleic acid immunization: Concepts and techniques associated with third generation vaccines"; Journal of Immunological Methods 1999; 229: 1-22).

IgGs were purified from tissue culture supernatants using affinity chromatography on Prosep A (Millipore UK Ltd.; Watford, WD18 SYH, UK) according to the manufacturer's instructions and purity assessed by SDS-polyacrylamide gel electrophoresis (PAGE).

Human heavy chain isotype was determined using a radial diffusion assay (The Binding Site; Birmingham, B29 6AT, UK). Human light chain isotype was determined using Western blotting with anti-human kappa chain and anti human lambda chain specific mouse monoclonal antibodies (Sigma-Aldrich Company Ltd; Gillingham, SP8 4XT, UK).

The purified IgG preparations were treated with mercuripapain (Sigma-Aldrich) at an enzyme/protein ratio of between 1:10 and 1:100 (depending on the particular monoclonal antibody) and passed through a Prosep A column to remove any intact IgG or Fc fragment from the Fab preparation (Y Oda, J Sanders, S Roberts, M Maruyama, R Kato, M Perez, V B Petersen, N Wedlock, J Furmaniak, B Rees Smith; "Binding characteristics of antibodies to the TSH receptor"; Journal of Molecular Endocrinology 1998; 20: 233-244). Intact IgG was undetectable by SDS-PAGE in the Fab preparations. IgG and Fab preparations of the monoclonal antibodies were labelled with $^{125}$I as described previously (Y Oda, J Sanders, S Roberts, M Maruyama, R Kato, M Perez, V B Petersen, N Wedlock, J Furmaniak, B Rees Smith; "Binding characteristics of antibodies to the TSH receptor"; Journal of Molecular Endocrinology; 1998; 20: 233-244). IgG preparations were labelled with biotin hydrazide (Pierce Rockford Ill. 61105 USA) according to the manufacturers instructions. Crystals of Fab fragments of the human monoclonal TSH receptor autoantibody were obtained and their crystal structure determined using standard techniques.

Patients

Sera from patients with Graves' disease of different disease duration were studied. The patients' sera studied showed inhibition of $^{125}$I-labelled TSH binding to the TSH receptor (see below). In addition, sera from 2 patients with Addison's disease (A1 and A2) and high levels of autoantibodies to 21-OH (113 and 1970 units per mL, RSR kit) and sera from 2 patients with type 1 diabetes mellitus (D1 and D2) with high levels of $GAD_{65}$ (3700 and 37.5 units per mL; RSR kit) were studied. Informed consent for the study was obtained from the patients. Sera from healthy blood donors (purchased from Golden West Biologicals, Vista, Calif. 92083, USA) were also studied. TRAb first international standard preparation (90/672) was obtained from the National Institute for Biological Standards and Control (NIBSC; Potters Bar, EN6 3QH, UK).

Inhibition of $^{125}$I-TSH and $^{125}$I-Mouse TSHR MAb Binding to the TSH Receptor Binding inhibition assays were carried out using TSH receptor coated tubes as described previously (J Sanders, Y Oda, S Roberts, A Kiddie, T Richards, J Bolton, V McGrath, S Walters, D Jaskolski, J Furmaniak, B Rees Smith; "The interaction of TSH receptor autoantibodies with $^{125}$I-labeled TSH receptor"; Journal of Clinical Endocrinology and Metabolism 1999; 84: 3797-3802) (reagents from RSR Ltd). Briefly, 100 µL of sample (tissue culture supernatant, purified IgG or Fab fragment, patient serum or NIBSC 90/672 standards) were incubated in TSH receptor coated tubes at room temperature for 2 hours with gentle shaking. After aspiration, the tubes were washed twice with 1 mL of assay buffer (50 mmol/L NaCl, 10 mmol/L Tris-HCl pH 7.8, 0.1% Triton X-100) before addition of 100 µL of $^{125}$I-TSH or $^{125}$I-MAb ($5\times10^4$ cpm) and incubation at room temperature for 1 hour with shaking. The tubes were then washed twice with 1 mL of assay buffer, aspirated and counted in a gamma counter.

Inhibition of Binding was Calculated as:—

$$100 \times 1 - \frac{cpm \text{ bound in the presence of test material}}{cpm \text{ bound in the presence of control material}}$$

Control materials used were culture medium, a pool of healthy blood donor sera or as otherwise indicated.

Analysis of Thyroid Stimulating Activities

The ability of monoclonal autoantibody preparations and patient sera to stimulate the production of cyclic AMP (or cAMP) in CHO cells expressing hTSH receptor (approximately 50,000. receptors per cell) (Y Oda, J Sanders, S Roberts, M Maruyama, R Kato, M Perez, V B Petersen, N Wedlock, J Furmaniak, B Rees Smith; "Binding characteristics of antibodies to the TSH receptor"; Journal of Molecular Endocrinology 1998; 20: 233-244) were carried out according to the method of R Latif, P Graves, T F Davies; "Oligomerization of the human thyrotropin receptor"; Journal of Biological Chemistry 2001; 276: 45217-45224. Briefly, CHO cells were seeded into 96 well plates (30,000 cells per well) and incubated for 24 hours in DMEM (Invitrogen Ltd; Paisley PA4 9RF, UK) containing 10% fetal calf serum. Culture was then continued in DMEM without fetal calf serum for a further 24 hours. The DMEM was then removed and test TSH, IgG, Fab and serum (100 µl diluted in NaCl free Hank's Buffered Salts solution containing 1g/L glucose, 20 mmol/L Hepes, 222 mmol/L sucrose, 15 g/L bovine serum albumin (BSA) and 0.5 mmol/L 3 isobutyl-1-methyl xanthine pH 7.4) added and incubated for 1 hour at 37° C. After removal of the test solutions, cells were lysed and assayed for cyclic AMP using a Biotrak enzyme immunoassay system from Amersham Biosciences; Chalfont St Giles, HPS 4SP, UK. In some experiments, the ability of patient sera and mouse monoclonal antibodies to the TSHR to inhibit the stimulating activity of TSH or hMAb TSHR1 was assessed. This was carried out by comparing (a) the stimulatory effects of TSH or hMAb TSHR1 alone with (b) the stimulatory effects of TSH or hMAb TSHR1 in the presence of patient sera or mouse monoclonal antibody.

Variable Region Gene Analysis

Total RNA was prepared from $1 \times 10^7$ cells of a TSH receptor autoantibody producing clone using the acid phenol guanidine method (P Chomczynski, N Sacchi; "Single-step method of RNA isolation by acid guanidinium thiocyanate-phenol-chloroform extraction"; Analytical Biochemistry 1987; 162: 156-159) and mRNA prepared using oligo dT magnetic beads (Dynal Biotech Ltd; Win-al, CH62 3QL, UK). RT-PCR reactions were performed using reagents from Invitrogen Ltd; Paisley PA4 9RF, UK.

Sense strand oligonucleotide primers were designed using the sequences recommended by the Medical Research Council's V-base database (www.mrc-cpe.cam.ac.uk). Antisense primers specific for human IgG1 heavy chain and lambda light chain were based on constant region encoding DNA sequences. Both sense and antisense primers included additional 5' restriction endonuclease site sequences to facilitate cloning of PCR products. IgG1 heavy chain and lambda light chain RT-PCR reactions were performed using the complete panel of appropriate primers. All primers were synthesized by Invitrogen Ltd. The RT reaction took place at 50° C. for 10 minutes followed immediately by 40 cycles of PCR (15 sec 94° C., 30 sec 55° C., 30 sec 72° C.). RT-PCR products were cloned into pUC18 and DNA prepared using the Wizard kit from Promega UK Ltd; Southampton SO 16 7NS, UK and sequenced by the Sanger-Coulson method (F Sanger, S Nicklen, A R Coulson; "DNA sequencing with chain terminating inhibitors"; Proceedings of the National Academy of Sciences of the USA 1977; 74: 5463-5467). V region sequences were compared with available sequences of human Ig genes using Ig blast (www.ncbi.nlm.nih.gov/igblast/igblast.cgi).

Immunoprecipitation Assay (IPA)

The cDNA encoding full length TSH receptor was placed downstream of the T7 promoter in pYES2 (Invitrogen) and used in an in vitro TnT system (Promega UK Ltd) to produce TSH receptor labelled with $^{35}$S-methionine as previously described (L Prentice, J Sanders, M Perez, R Kato, J Sawicka, Y Oda, D Jaskolski, J Furmaniak, B Rees Smith; "Thyrotropin (TSH) receptor autoantibodies do not appear to bind to the TSH receptor produced in an in vitro transcription/translation system"; Journal of Clinical Endocrinology and Metabolism 1997; 82: 1288-1292). Briefly 50 µL, $^{35}$S-labelled TSH receptor (25 000-30 000 cpm) diluted in HSB (150 mmol/L Tris-HCL pH 8. 3.200 mmol/L NaCl and 10 mg/mL bovine serum albumin containing 1% Tween 20) were added to duplicate 50 µL aliquots of diluted test sample and incubated for 2 hours at room temperature. Immune complexes were then precipitated by addition of protein A sepharose (Sigma-Aldrich) and counted in a scintillation counter.

TSH Receptor Preparations and Western Blotting

Full-length human TSH receptor was expressed in CHO-K1 cells, extracted with 1% Triton X-100 and purified by TSH receptor monoclonal antibody affinity chromatography as described previously (Y Oda, J Sanders, M Evans, A Kiddie, A Munkley, C James, T Richards, J Wills, J Furmaniak, B Rees Smith; "Epitope analysis of the human thyrotropin (TSH) receptor using monoclonal antibodies"; Thyroid 2000; 10:1051-1059).

The purified CHO cell produced TSH receptor was run on 9% SDS-PAGE gels, blotted onto nitrocellulose and reacted with test antibodies as described previously (Y Oda, J Sanders, M Evans, A Kiddie, A Munkley, C James, T Richards, J Wills, J Furmaniak, B Rees Smith; "Epitope analysis of the human thyrotropin (TSH) receptor using monoclonal antibodies"; Thyroid 2000; 10: 1051-1059).

Epitope Analysis Using TSH Receptor Peptides

Twenty six peptides each 25aa long covering the whole of the extracellular domain of the human TSH receptor were kindly provided by Dr J Morris (J C Morris, E R Bergert, D J McCormick; "Structure-function studies of the human thyrotropin receptor. Inhibition of binding of labeled thyrotropin (TSH) by synthetic human TSH receptor peptides"; Journal of Biological Chemistry 1993; 268: 10900-10905). A human 21-OH peptide (C1, SSSRVPYKDRARLPL) which binds to an M21-OH5 MAb (S Chen, J Sawicka, L Prentice, J F Sanders, H Tanaka, V Petersen, C Betterle, M Volpato, S Roberts, M Powell, B Rees Smith, J Furmaniak; "Analysis of autoantibody epitopes on steroid 21-hydroxylase using a panel of monoclonal antibodies"; Journal of Clinical Endocrinology and Metabolism 1998; 83: 2977-2986) was used as a positive control and a human monoclonal antibody to $GAD_{65}$ (N Hayakawa, L D K E Premawardhana, M Powell, M Masuda, C Arnold, J Sanders, M Evans, S Chen, J C Jaume, S Baekkeskov, B Rees Smith, J Furmaniak; "Isolation and characterization of human monoclonal autoantibodies to glutamic acid decarboxylase"; Autoimmunity 2002; 35: 343-355) was used as a negative control. The peptide ELISA was carried out as described previously (Y Oda, J Sanders, M Evans, A Kiddie, A Munkley, C James, T Richards, J Wills, J Furmaniak, B Rees Smith; "Epitope analysis of the human thyrotropin (TSH) receptor using monoclonal antibodies"; Thyroid 2000; 10: 1051-1059).

Interaction of Monoclonal TSHR Autoantibody Preparations with the TSH Receptor Coated onto Plastic Tubes or ELISA Plate Wells (a) $^{125}$I-Labelled Autoantibody Test samples including patient sera (100 µL) were incubated in TSH receptor coated tubes (RSR Ltd.) at room temperature for 2 hours with gentle shaking. After aspiration, the tubes were washed twice with 1 mL of assay buffer before addition of 100 µL of labelled autoantibody preparation (30, 000 cpm) and incubation at room temperature for 1 hour with shaking. The tubes were then washed twice with 1 mL of assay buffer, aspirated and counted in a gamma counter. Inhibition of $^{125}$I-labelled autoantibody binding was calculated using the formula as for inhibition of TSH binding (see above).

(b) Biotin Labelled Monoclonal Autoantibody and Biotin Labelled TSH

The procedure described previously (J Bolton, J Sanders, Y Oda, C Chapman, R Konno, J Furmaniak and B Rees Smith;

"Measurement of thyroid-stimulating hormone receptor autoantibodies by ELISA"; Clinical Chemistry, 1999; 45: 2285-2287) was used. Briefly, test samples including patient sera (75 µL) were incubated in TSH receptor coated ELISA plate wells (RSR Ltd) for 2 hours with shaking (200 shakes per minute) on an ELISA plate shaker. Test samples were then removed and the wells washed once with assay buffer. Biotin-labelled monoclonal TSH receptor autoantibody (1 ng in 100 µL) or biotin labelled porcine TSH (RSR Ltd; 5 ng in 100 µL) were then added and incubation continued for 25 minutes at room temperature without shaking. The wells were washed once, 100 µL of streptavidin-peroxidase (RSR Ltd; 10 ng in 100 µL) added and incubation continued for 20 minutes at room temperature without shaking. The wells were then washed 3 times, the peroxidase substrate tetramethyl benzidine (RSR Ltd, 100 µL) added. After incubation for 30 minutes at room temperature without shaking 50 µL of 0.5M $H_2SO_4$ was added to stop the substrate reaction and the absorbance of each well read at 450 nm on an ELISA plate reader. Inhibition of biotinylated MAb or TSH binding was expressed as an index calculated as:—

$$100 \times 1 - \frac{\text{test sample absorbance at 450 nm}}{\text{negative serum control absorbance at 450 nm}}$$

Scatchard Analysis of Monoclonal Autoantibody Binding to TSH Receptor Coated Tubes Unlabelled IgG or Fab in 50 µL of assay buffer and 50 µL of $^{125}$I-labelled hMAb IgG or Fab (30,000 cpm in assay buffer) were incubated for 2 hours at room temperature with gentle shaking, washed twice with 1 mL of assay buffer and counted in a gamma counter. The concentration of IgG or Fab bound vs bound/free was plotted (G Scatchard; "The attraction of proteins for small molecules and ions"; Annals of the New York Academy of Sciences 1949; 51: 660-672) to derive the association constants.

Binding of TSH Receptor to Tubes Coated with Monoclonal TSH Receptor Autoantibodies Test samples including patient sera (100 µl) and detergent solubilised TSH receptor (20 µL) were incubated for 1 hour at room temperature. Duplicate 50 µL aliquots of the incubation mixture were then added to plastic tubes (Nunc Maxisorp) which had been coated with monoclonal TSH receptor autoantibody Fab (200 µL of 10 µg/mL overnight at 4° C. followed by washing and post coating). After incubation for 1 hour at room temperature with gentle shaking, the tubes were washed, 100 µL (40,000 cpm) of $^{125}$I-labelled TSH receptor C terminal monoclonal antibody 4E31 (J Sanders, Y Oda, A Kiddie, T Richards, J Bolton, V McGrath, S Walters, D Jaskolski, J Furmaniak, B Rees Smith; "The interaction of TSH receptor autoantibodies with $^{125}$I-labelled TSH receptor"; Journal of Clinical Endocrinology and Metabolism 1999; 84: 3797-3802) added and incubation continued for a further 1 hour with gentle shaking. Then tubes were washed and counted for $^{125}$I.

Cloning and Expression of Recombinant hMAb TSHR1 Fab in E. coli

The hMAb TSHR1 heavy chain RT-PCR product (see Variable Region Gene Analysis section) was cut with XhoI and SpeI restriction endonucleases and the hMAb TSHR1 light chain PCR product was cut with SacI and XbaI restriction endonucleases and both heavy and light chain cDNAs cloned into the Immunozap H/L vector (Stratagene Europe; Amsterdam, Netherlands) (I Matthew, G Sims, S Ledwidge, D Stott, D Beeson, N Willcox, A Vincent; "Antibodies to acetylcholine receptor in parous women with myasthenia: evidence for immunization by fetal antigen"; Laboratory Investigation 2002; S2: 1-11) under the control of the lacZ promoter. Plasmid DNA was prepared using the Qiagen midi plasmid purification kit (Qiagen Ltd; Crawley, RH10 9AX, UK) and the presence of hMAb TSHR1 heavy and light chain cDNAs confirmed by sequencing using the Sanger-Coulson method (F Sanger, S Nicklen, A R Coulsen; "DNA sequencing with chain terminating inhibitors"; Proceedings of the National Academy of Sciences of the USA 1977; 74: 5463-5467). Plasmid DNA was transformed into 2 different E. coli strains (a) XL1-Blue MRF' (Stratagene) and (b) HB2151 (Amersham Biosciences) and grown overnight at 37° C. on LB ampicillin (Tryptone 10 g/L, Yeast Extract 5 g/L, NaCl 10 g/L, 100 µg/mL final concentration Ampicillin) agar plates (15 g/L agar). Precultures (one colony in 3 mL LB ampicillin+1% glucose) were grown overnight at 37° C. with shaking. Production of the recombinant Fab is inhibited in the presence of glucose. Precultures after overnight incubation were diluted 1/100 (0.5 mL in 50 mL LB ampicillin) and grown at 37° C. until the $OD_{600}$ was between 0.4-0.6. These cultures were placed at 30° C. with shaking for 20 minutes. Thereafter isopropyl-β-D thiogalactoside (IPTG) was added to a final concentration of 1 mmol/L and cultures continued to be incubated overnight (16 hours) at 30° C. with shaking. The cultures were then centrifuged at 3000 rpm for 30 minutes at 4° C. and the culture supernatants and pellets recovered. The pellets, were resuspended in 1 mL of ice cold TES buffer (0.2 mol/L Tris-HCl pH 8.0, 0.5 mol/L EDTA and 0.5 mol/L sucrose) by vortexing. A further 1.5 mL of ice cold TES buffer diluted 5× in $H_2O$ was added, the mixture vortexed again and incubated on ice for 30 minutes then recentrifuged to give a second supernatant or periplasmic fraction (PF). The culture supernatant and PF were filtered through a 0.45 µm filter and dialysed overnight into 10 mmol/L Tris pH 7.5, 50 mmol/L NaCl. Culture supernatant or PF from untransformed XL1-Blue MRF' and HB2151 cells and XL1-Blue MRF' transformed with hMAb TSHR1 plasmid (XL1-Blue MRF'/hMAb TSHR1) and HB2151 transformed with hMAb TSHR1 plasmid (HB2151/hMAb TSHR1) grown with glucose without IPTG ie non-induced were also prepared. The culture supernatants and PF were assayed for (a) their ability to inhibit TSH binding to the TSHR, (b) their ability to stimulate cyclic AMP production in CHO cells expressing TSHR, and (c) total recombinant Fab concentration by radioimmunoassay. In this assay, calibrators and test materials including culture supernatants and PF (100 µL in duplicate) diluted in assay buffer (50 mmol/L NaCl, 10 mmol/L Tris-HCl pH 7.8, 0.1% Triton X-100) were incubated for 1 hour at room temperature in plastic tubes coated with Fab specific goat anti human IgG (from Sigma Aldrich, Poole, BH12 4QH, UK). The tubes were then washed with assay buffer (2×1 mL) and 100 µL of $^{125}$I-labelled hMAb TSHR1 Fab (30,000 cpm) added followed by incubation at room temperature. After 1 hour, the tubes were washed again (2×1 mL) and counted for $^{125}$I. The counts bound were plotted against concentration of Fab (hybridoma produced hMAb TSHR1 Fab) in the calibrators (5-500 ng/mL) and the concentration of recombinant Fab in the various test materials read off this calibration curve. The detection limit for this assay was 5-10 ng/mL of Fab.

Cloning and Expression of Recombinant 4B4 (a Human MAb to Glutamic Acid Decarboxylase or GAD) and Recombinant Hybrid Fabs (Mixed HC and LC of hMAb TSHR1 and 4B4)

Recombinant 4B4 Fab (4B4 is described in detail by N Hayakawa, LDKE Premawardhana, M Powell, M Masuda, C Arnold, J Sanders, M Evans, S Chen, J C Jaume, S Baekkeskov, B Rees Smith, J. Furmaniak. Isolation and characterization of human monoclonal antibodies to glutamic acid decarboxylase. Autoimmunity 2002 volume 35 pp 343-355) and recombinant hybrid Fabs were produced by cloning the respective HC and LC into Immunozap H/L vector and expressed in HB2151 cells as described for recombinant hMAb TSHR1 Fab. The culture supernatants and periplasmic fraction were assayed for their ability to (a) inhibit TSH binding to the TSHR (b) to stimulate cyclic AMP production in CHO cells expressing the TSHR and (c) for total recombinant Fab concentration as described above. In addition, GAD Ab activity was assessed as described below.

Measurement of Recombinant GAD Ab Fab Activity in Culture Supernatants and Periplasmic Fractions An assay based on the ability of GAD Ab Fab preparation to inhibit the binding of $^{125}$I-labelled GAD (from RSR Ltd, Cardiff, CF23 SHE, UK) to the human monoclonal antibody to GAD (4B4) was used. In the assay, test samples diluted in GAD Ab assay buffer (150 mmol/L NaCl, 50 mmol/L Tris-HCl pH 8.0, 1% v/v Tween 20, 1 g/L bovine serum albumin and 0.5 g/L NaN$_3$) were incubated (50 μL in duplicate with $^{125}$I-labelled GAD (30,000 cpm in 50 μL of GAD Ab assay buffer) for 1 hour at room temperature. Then, 50 μL of 4B4 IgG (0.1 μg/mL in GAD Ab assay buffer) was added and incubation continued for 24 hours at room temperature. Solid phase protein A (50 μL in GAD Ab assay buffer; from RSR Ltd) was then added to precipitate complexes of 4B4 IgG-$^{125}$I-labelled GAD (protein A does not react with complexes of Fab and $^{125}$I-labelled GAD). After allowing the reaction with protein A to proceed for 1 hour at room temperature, the precipitates were pelleted by centrifugation (1500 g for 30 minutes at 4° C.), washed with 1 mL of GAD Ab assay buffer and counted for $^{125}$I. $^{125}$I-labelled GAD binding in the absence of 4B4 IgG was 4-5% of the total cpm added.

Production of Anti-Idiotypic Antibodies to hMAb TSHR1

6-8 week old BALB/c mice were immunised intraperitoneally with 50 μg hMAb TSHR1 Fab in complete Freunds adjuvant followed by a second injection with 50 μg hMAb TSHR1 Fab in incomplete Freunds adjuvant after 25 days and a further injection of 50 μg hMAb TSHR1 Fab 4 days before removal of the spleen. The spleen cells from antibody positive mice (see below) were fused with a mouse myeloma cell line and monoclonal antibodies isolated as above for TSHR MAbs. The levels of anti-idiotypic antibody in the mouse sera and cell culture wells were measured by inhibition of $^{125}$I-hMAb TSHR1 Fab binding to TSHR coated tubes. In particular, duplicate 60 μL aliquots of test sample (diluted in assay buffer: 50 mmol/L NaCl, 10 mmol/L Tris-HCl pH 7.8, 0.1% Triton X-100) were incubated with 60 μL of $^{125}$I-hMAb TSHR1 Fab (30000 cpm diluted in assay buffer) for 1 hour at room temperature. 100 μL of the mixture was transferred to duplicate TSHR coated tubes (RSR Ltd) with 20 μL start buffer (see above) and incubation continued for a further two hours at room temperature with shaking. The tubes were then washed with 2×1 mL of assay buffer and counted for $^{125}$I. The presence of anti-idiotypic antibodies reactive with hMAb TSHR1 was evident from the ability of test samples to inhibit the binding of labelled hMAb TSHRI Fab to the TSHR coated tubes.

Results

Lymphocytes (30×10$^6$) obtained from 20 mL of patient's blood were plated out at 1×10$^6$ per well on a 48 well plate with 200 μL of EBV supernatant on feeder layers of mouse macrophages. On day 11 post EBV infection the supernatants were monitored for inhibition of $^{125}$I-TSH binding. One well was found to be positive for inhibition of binding, the levels of inhibition increasing to greater than 90% inhibition by day 16 and stayed at that level until day 24, after which time they decreased. The cultures were expanded and fused with K6H6/B5 cells on day 21, 23, 26 and 27 post EBV infection; in total 7 fusion experiments were carried out. Each fusion was plated across 3×96 well plates (ie 21 plates in total) and one well, stably producing antibodies with $^{125}$I-TSH binding inhibiting activity was obtained. This was followed by 3 rounds of re-cloning to yield a single clone producing a human monoclonal antibody which inhibited labelled TSH binding to the TSH receptor. This human monoclonal TSH receptor autoantibody was designated hMAb TSHR1 and was of subclass IgG1 with a lambda light chain.

Figure 2:
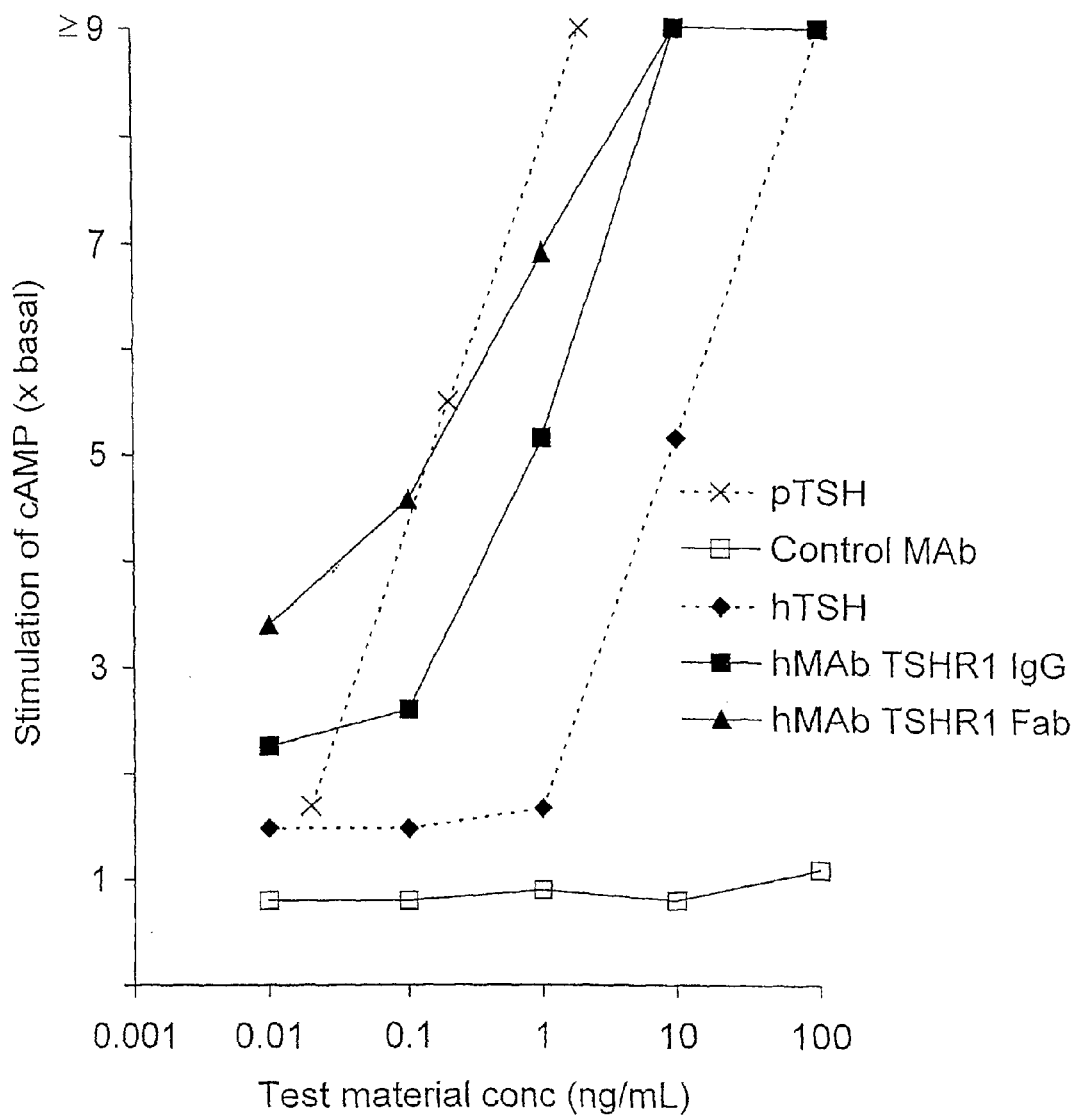
FIG. 2 shows thyroid stimulating activity of hMAb TSHR1 IgG and Fab, porcine TSH (70 units/mg; pTSH) recombinant human TSH (6.7 units/mg; hTSH) and a control monoclonal antibody (MAb; human monoclonal autoantibody to thyroid peroxidase (2G4)). Basal=cAMP produced in the presence of NaCl free Hanks Buffered Salt Solution only.

The ability of different concentrations of hMAb TSHR1 IgG and Fab to inhibit labelled TSH binding to the TSH receptor is shown in FIG. 1. As can be seen in FIG. 1 as little as 1 ng/mL of these preparations inhibited TSH binding with more than 90% inhibition being obtained with 1000 ng/mL. TSMAb TSHR1 IgG and Fab also stimulated cyclic AMP production in CHO cells transfected with the TSH receptor as shown in FIG. 2. As little as 1 ng/mL of hMAb TSHR1 IgG or Fab caused strong stimulation of cyclic AMP. Similar levels of stimulation were observed with 0.1 ng/mL porcine TSH and 10 ng/mL of human TSH. Comparison of the ability of the serum from the original lymphocyte donor (taken at the same time as the blood sample for lymphocyte isolation) to inhibit labelled TSH binding to the TSH receptor and to stimulate cyclic AMP production in TSH receptor transfected CHO cells is shown in FIG. 3A. Inhibition of TSH binding could be detected with serum diluted 500× whereas stimulation of cyclic AMP could be detected with serum diluted 5000×.

$^{125}$I-labelled hMAb TSHR1 IgG bound to TSH receptor coated tubes and Scatchard analysis indicated an association constant of $5×10^{10}$ molar$^{-1}$. This binding was inhibited by sera from patients with Graves' disease who had TSH receptor autoantibodies (detectable by inhibition of labelled TSH binding) (Table 1), $^{125}$I-labelled hMAb TSHR1 Fab also bound to TSH receptor coated tubes (association constant by Scatchard analysis=$4.5×10^{10}$ molar$^{-1}$) and this binding was inhibited by TSH receptor autoantibody positive Graves' sera (Table 2). In addition, detergent solubilised preparations were able to bind to plastic tubes coated with hMAb TSHR1 and this binding could be inhibited by sera containing TSH receptor autoantibodies (Table 3).

As shown in Table 4 hMAb TSHRI-biotin bound to TSH receptor coated ELISA plates and the binding was inhibited by the international reference preparation NIBSC 90/672 and serum from patients with Graves' disease. Inhibition of binding was not observed by sera from healthy blood donors. FIG. 3B shows a graphical representation of a comparison between an assay for TSHR autoantibodies based on hMAb TSHR1-biotin and earlier assays. The sensitivity of the assay based on hMAb TSHR1-biotin is clearly superior according to concentration of the international standard NIBSC 90/672 detectable. This was confirmed in a study of sera from 72 patients with Graves' disease shown in FIG. 3C. Healthy blood donor sera (n=100) and sera from subjects with non-thyroid diseases (n=43) gave respectively values of up to 10% inhibition of hMAb TSHR1 binding and up to 11% inhibition of TSH binding in this study.

hMAb TSHR1 IgG did not react with full length TSH receptor preparations on Western blot analysis nor did it react well with $^{35}$S-labelled full length TSH receptor in the immunoprecipitation assay nor in the TSH receptor peptide ELISA. This lack of reactivity indicates that hMAb TSHR1 reacts with conformational rather than linear epitopes on the TSH receptor.

Sequence analysis of the genes coding for hMAb TSHR1 indicated that the heavy chain V region genes were of the VH5 family, the D gene of the D6-13 family and the J gene of the JH5 family and for the light chain the V-gene region is from the VL1-11 germline and the J-gene region is from the JL3b germline. The heavy chain nucleotide and amino acid sequences are shown in FIGS. 4 and 5 respectively and the light chain nucleotide and amino acid sequences are shown in FIGS. 6 and 7 respectively. These sequences are a refinement of the HC and LC nucleotide sequences determined using PCR primers which are degenerate. In particular a HC sequencing artefact for nucleotides 115-120 was identified. Sequencing indicated cacgtg (transcribed to amino acids His Val) whereas the crystal structure more reliably indicated amino acids Gln Leu (corresponding bases being cagctg). Crystal structure analysis also enabled refinement of the HC and LC derived amino acid sequences particularly in the degenerate PCR primer region. In the case of the LC amino acid 2 was found to be Pro by RT-PCR but was Thr from the crystal structure. In the case of the HC amino acid 2 was found to be Met by RT-PCR but was Val from the crystal structure.

Comparison of the activities of hMAb TSHR1 IgG preparations and the international standard for TSH receptor autoantibodies in terms of inhibition of labelled TSH binding are shown in Table 5. This enabled a specific activity of hMAb TSHR1 IgG to be estimated as 138 units of NIBSC 90/672 per mg of protein when the assays were carried out in serum and 163 units per mg when the assays were carried out in assay buffer (mean of the 2 values=150 units/mg). hMAb TSHR1 Fab preparations were 288 and 309 units per mg in serum and assay buffer respectively (mean of the 2 values=300 units/mg). Table 6 shows a similar analysis of the lymphocyte donor serum and the donor serum IgG. As can be seen the donor serum contains a mean of 0.38 units/mL of NIBSC 90/672 (0.36 and 0.4 in serum and assay buffer respectively) and the donor serum IgG has a mean specific activity of 0.059 units per mg of protein. These results are summarised in Table 7 and comparison with the specific activity of hMAb TSHR1 IgG (150 units/mg) indicates that the monoclonal autoantibody IgG is 2500 times more active than the lymphocyte donor serum IgG in terms of inhibition of TSH binding.

Initial assessment of the activities of the various IgG and serum preparations in terms of stimulation of cyclic AMP in CHO cells transfected with the TSH receptor are also shown in Table 7. The stimulation of cyclic AMP assay is characterized by considerable within assay and between assay variability. This relates to several factors including variation in the number and quality of cells initially seeded into the 96 well plates and variation in growth rate of the seeded cells over the subsequent 48 hours. Consequently the assays of hMAb TSHR1 IgG and Fab, lymphocyte donor serum and serum IgG and NIBSC 90/672 were carried out repeatedly and the results are summarized in Table 8. The specific activity of the hMAb TSHR1 IgG was 318 units per mg in the stimulation assay compared with 0.1 units per mg for the lymphocyte donor serum IgG ie the monoclonal autoantibody IgG was about 3000 times as active as the donor serum IgG in terms of stimulation of cyclic AMP production. This value is in reasonable agreement with the value of 2500 times observed for inhibition of TSH binding measurements (see above and Tables 5 and 6). Table 9 shows a further analysis of the TSH receptor stimulating effects of hMAb TSHR1 IgG and Fab and the lymphocyte donor serum IgG.

The effects of porcine TSH and hMAb TSHR1 IgG on stimulation of cyclic AMP production in CHO cells expressing the TSH receptor were additive as can be seen in the results shown in Table 10.

Typical results observed in the stimulation of cyclic AMP assay with the reference preparation NIBSC 90/672 are shown in Table 11.

Tables 12 and 13 show the effects of the various *E. coli* culture supernatants in terms of inhibition of labelled TSH binding and stimulation of cyclic AMP production respectively. Transformed (with hMAb THSR1 plasmid) and IPTG induced cultures of both strains of *E. coli* produced sufficient amounts of recombinant hMAb TSHR Fab to act as potent inhibitors of TSH binding (Table 12) and powerful stimulators of cyclic AMP production (Table 13). Control culture supernatants (from untransformed cells and transformed but non-induced cells) did not produce detectable levels of binding inhibition (Table 12) or stimulating (Table 13) activities.

In further control experiments, a recombinant human antibody Fab produced by cloning and expression of the HC and LC of a human monoclonal antibody to GAD (4B4) were analysed. Assays of culture supernatants and periplasmic fractions indicated that recombinant 4B4 Fab did not have detectable inhibition of TSH binding activity (Tables 14 and 15) or TSHR stimulating activity (Tables 16 and 17). Furthermore, hybrid Fabs consisting of (a) hMAb TSHR1 HC and 4B4 LC (b) hMAb TSHR1 LC and 4B4 HC did not show interaction with the TSHR in either assay (Tables 14-17). Assays for GAD Ab activity in these various recombinant Fab preparations were only able to detect GAD Ab expression in cells transformed with 4B4 HC and 4B4 LC (Tables 18 and 19). Recombinant hMAb TSHR1 Fab did not show detectable GAD Ab activity and neither did recombinant Fab hybrids consisting of mixtures of 4B4 and hMAb TSHR1 HC and LC (Tables 18 and 19).

Figure 8:
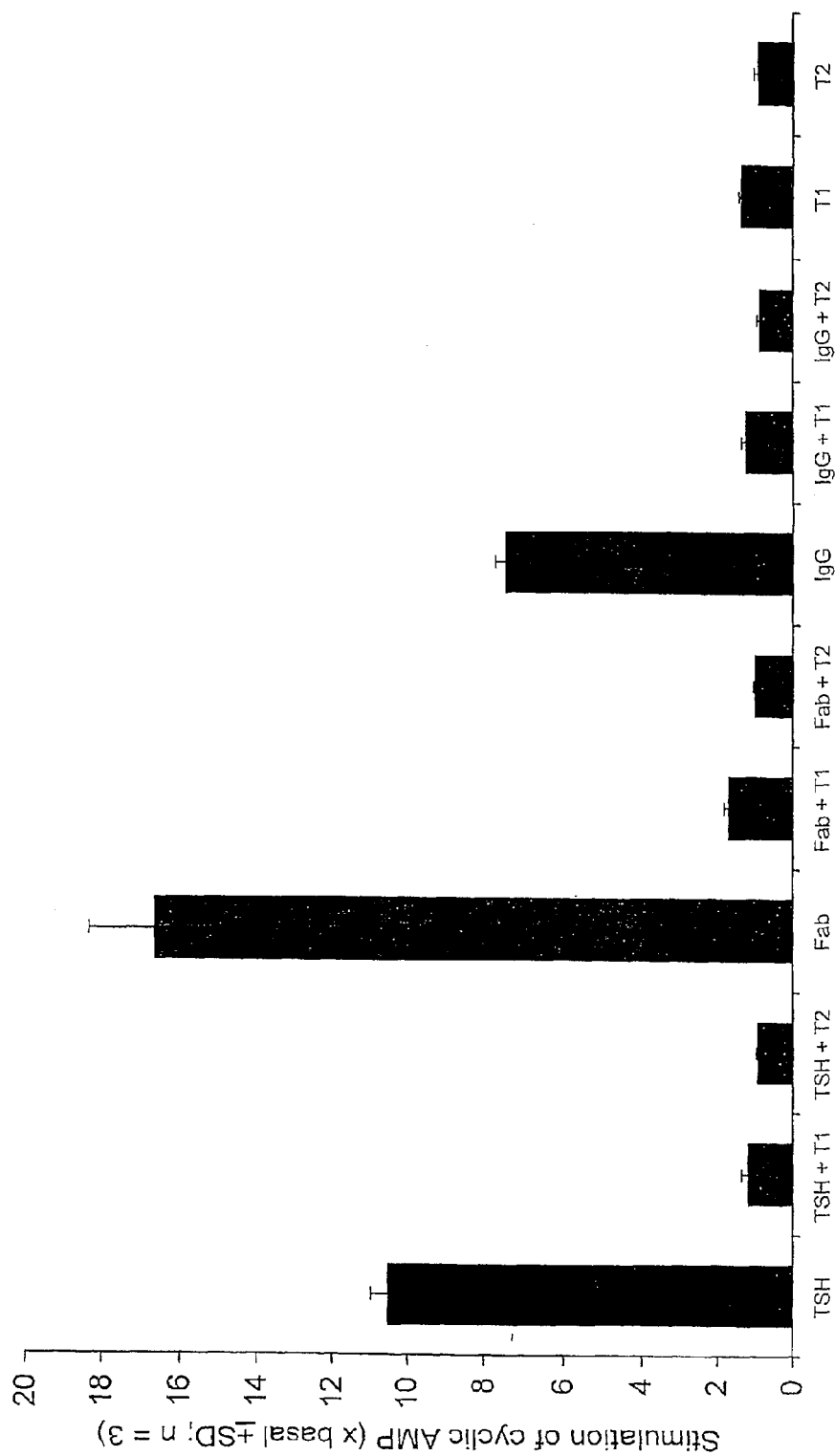
FIG. 8 shows effects of 2 patients sera (T1 and T2 with TSH antagonist activity) on stimulation of cyclic AMP production by pTSH (0.5 ng/ml) and hMAb TSHR1 IgG (10 ng/ml) and Fab (5 ng/ml) in CHO cells transfected with the TSHR.

The ability of hMAb TSHR1 to stimulate cyclic AMP production in CHO cells transfected with the TSHR was inhibited by patient sera containing TSHR autoantibodies which acted as TSH antagonists (FIG. 8). In addition, a mouse monoclonal antibody to the TSHR (9D33) was able to block hMAb TSHR1 stimulating activities (Table 20) whereas another TSHR mouse MAb (2B4) was ineffective (Table 20). However 2B4 was able to block the stimulating activities of TSH as was 9D33 (Table 21). Table 22 shows the ability of 2B4 and 9D33 to inhibit the binding of $^{125}$I-labelled TSH and $^{125}$I-labelled hMAb TSHR1 to TSHR plastic tubes. 9D33 was able to inhibit labelled TSH binding and labelled hMAb TSHR1 binding quite effectively (more than 50% inhibition at 10 µg/mL). 2B4 was an effective inhibitor of labelled TSH binding to the TSHR (more than 80% inhibition at 1 µg/mL) but had only a minor effect on hMAb TSHR1 binding (11% inhibition at 1 µg/mL) or on 9D33 binding (22% inhibition at 1 µg/mL). The binding of labelled 9D33 to TSHR coated tubes was inhibited by sera from patients with Graves' disease containing TSHR autoantibodies (as measured by inhibition of labelled TSH binding to the TSHR) whereas healthy blood donor sera and sera from patients with other autoimmune diseases had little or no effect (Table 23). Labelled 9D33 binding to the TSHR was inhibited by TSHR autoantibodies with TSH agonist or antagonist properties (Table 24) and by the international standard NIBSC 90/672 (Table 25). Scatchard analysis indicated that 9D33 and 2B4 had affinities of $2\times10^{10}$ molar$^{-1}$ and $1\times10^{10}$ molar$^{-1}$ respectively for TSH receptors coated onto plastic tubes.

Immunisation of mice with hMAb TSHR1 Fab resulted in production of antibodies in the mice sera (polyclonal antibodies) which were capable of binding to hMAb TSHRI Fab in such a way as to inhibit the ability of the Fab to bind to the TSHR (Table 26). Furthermore, a monoclonal antibody produced from the spleen cells of a mouse immunised with hMAb TSHR1 Fab was also able to inhibit the Fab binding to the TSHR (Table 27).

Overall our analysis indicates that the human monoclonal autoantibody hMAb TSHR I has the TSH receptor binding and thyroid stimulating characteristics of the TSH receptor autoantibodies in the serum of the lymphocyte donor. As detailed above, the monoclonal antibody was also produced as a recombinant Fab preparation.

CONCLUSIONS (a) We have produced a human monoclonal autoantibody to the TSH receptor which has similar properties to the TSH receptor autoantibody in the donor patient's serum. The monoclonal antibody was also produced as a recombinant Fab preparation.
(b) The monoclonal antibody IgG and Fab and recombinant Fab preparations are powerful thyroid stimulators and effective inhibitors of labelled TSH binding to the TSH receptor.
(c) Binding of labelled MAb IgG and Fab preparations to the TSH receptor is inhibited by TSH receptor autoantibody positive sera from patients with Graves' disease but not by healthy blood donor sera or sera from patients with other autoimmune diseases. Assay systems for TSHR autoantibodies based on inhibition of labelled hMAb TSHR1 binding to the TSH receptor are more sensitive than other assays so far described.
(d) TSH receptor autoantibodies which act as TSH antagonists as well as TSH receptor autoantibodies which act as TSH agonists inhibit labelled hMAb TSHR1 binding to the TSH receptor.
(e) hMAb TSHR1 preparations coated onto plastic tubes bind TSH receptor and this binding is inhibited by TSH receptor autoantibodies in different patient sera.
(f) A mouse monoclonal antibody (9D33) which inhibits hMAb TSHR1 binding to the TSHR was also found to block the stimulating activity of hMAb TSHR1 and TSH.
(g) Mouse polyclonal and monclonal antibodies to hMAb TSHR1 have been produced which bind to hMAb TSHR1 in such a way as to prevent it binding to the TSH receptor. These anti-idiotypic antibodies compete therefore with the TSHR for hMAb TSHR1 and as such they may be useful alternatives to the TSHR in applications where a binding partner for TSHR autoantibodies is required.
(h) These results indicate that hMAb TSHR1 and/or its derivatives and/or its competitors can be used as a replacement for TSH in
(i) assays for TSH receptor autoantibodies, TSH and related ligands
(ii) various in vivo applications involving provision of TSH agonist or TSH antagonist activities.
(iii) identification and provision of new types of TSH receptor autoantibody binding sites.

TABLE 1

Effect of patient sera on $^{125}$I-labelled hMAb TSHR1 IgG binding to the TSH receptor and comparison with effect on $^{125}$I-labelled TSH binding to the TSH receptor

| Test material | inhibition of labelled hMAb TSHR1 binding | inhibition of TSH binding |
|---|---|---|
| G1 | 62 | 80 |
| G2 | 91 | 93 |

TABLE 1-continued

Effect of patient sera on $^{125}$I-labelled hMAb TSHR1 IgG binding to the TSH receptor and comparison with effect on $^{125}$I-labelled TSH binding to the TSH receptor

| Test material | inhibition of labelled hMAb TSHR1 binding | inhibition of TSH binding |
|---|---|---|
| G3 | 91 | 76 |
| G4 | 94 | 92 |
| G5 | 93 | 94 |
| G6 | 76 | 85 |
| G7 | 87 | 90 |
| G8 | 65 | 45 |
| G9 | 88 | 90 |
| G10/10 | 83 | 59 |
| G10/20 | 69 | 43 |
| G10/40 | 56 | 29 |
| G10/80 | 42 | 19 |
| G11/10 | 75 | 73 |
| G11/20 | 59 | 54 |
| G11/40 | 39 | 33 |
| G11/80 | 22 | 18 |
| N1 | 3.1 | 7.7 |
| N2 | 2.4 | 2.6 |
| N3 | −1.0 | 4.5 |
| N4 | −11 | 6.5 |
| N5 | 1.7 | 5.0 |
| N6 | 2.8 | 1.7 |
| N7 | 5.2 | −0.8 |
| N8 | 3.5 | 0.2 |
| N9 | 2.8 | −0.6 |
| N10 | 4.5 | 2.2 |
| D1 | −4.8 | 2.2 |
| A1 | −3.1 | 1.3 |
| A2 | −3.5 | −3.0 |

G1-G11 are sera from patients with a history of Graves' disease.
G9 serum has high levels of TSH blocking (ie TSH antagonist activity).
G10 and G11 have high levels of thyroid stimulating activity.
G10 is the lymphocyte donor serum.
/10, /20 etc indicate dilution factor in a pool of healthy blood donor sera.
N1-N10 are sera from healthy blood donors.
D1 is from a patient with type 1 diabetes mellitus (positive for autoantibodies to glutamic acid decarboxylase).
A1 and A2 are from patients with Addison's disease (positive for steroid 21-hydroxylase autoantibodies).
In the presence of the pool of healthy blood donor sera about 25% of $^{125}$I-labelled MAb IgG bound to the TSHR coated tubes.

TABLE 2

Effect of patient sera on $^{125}$I-labelled hMAb TSHR1 Fab binding to the TSH receptor and comparison with effect on $^{125}$I-labelled TSH binding to the TSH receptor

| Test material | inhibition of labelled Fab binding | inhibition of TSH binding |
|---|---|---|
| NIBSC 90/672 diluted in a pool of healthy blood donor serum | | |
| to 1 U/L | 17 | 13 |
| to 2 U/L | 27 | 24 |
| to 4 U/L | 47 | 44 |
| to 8 U/L | 61 | 65 |
| Healthy blood donor-serum A | −3 | <10 |
| Healthy blood donor serum B | 3 | <10 |
| Healthy blood donor serum C | 4 | <10 |
| Healthy blood donor serum D | −4 | <10 |
| Healthy blood donor serum E | 0 | <10 |
| Graves' serum F | 64 | 78 |
| Graves' serum G | 42 | 54 |
| Graves' serum H | 49 | 69 |
| Graves' serum I | 24 | 36 |
| Graves' serum J | 76 | 88 |

TABLE 3

Binding of TSHR to plastic tubes coated with hMAb TSHR 1 Fab and inhibition of TSHR binding by sera containing TSHR autoantibodies

| Test material | cpm bound[1] |
|---|---|
| Healthy blood donor serum A | 8406 |
| Healthy blood donor serum B | 8430 |
| TSHR autoantibody positive serum 1 | 1527 |
| TSHR autoantibody positive serum 2 | 1131 |
| TSHR autoantibody positive serum 3 | 1199 |

[1]TSHR binding was detected using a $^{125}$I-labelled mouse monoclonal antibody to the TSHR C terminus; total cpm = 39,000 per tube.

TABLE 4

Effect of patient serum samples on binding of biotin labelled hMAb TSHR1 and biotin labelled TSH to ELISA plate wells coated with TSHR

| | hMAb TSHR1 biotin | | TSH biotin | |
|---|---|---|---|---|
| | OD$_{450}$ | % inhibition | OD$_{450}$ | % inhibition |
| HBD pool | 1.852 | 0 | 1.778 | 0 |
| HBD pool plus 1 U/mL | 1.46 | 21 | 1.489 | 16 |
| HBD pool plus 2 U/mL | 1.168 | 37 | 1.304 | 27 |
| HBD pool plus 4 U/mL | 0.792 | 57 | 0.947 | 47 |
| HBD pool plus 8 U/mL | 0.539 | 71 | 0.492 | 72 |
| HBD pool plus 40 U/mL | 0.118 | 94 | 0.233 | 87 |
| Serum P1 | 1.415 | 24 | 1.397 | 21 |
| Serum P2 | 1.264 | 32 | 1.256 | 29 |
| Serum P3 | 0.558 | 70 | 0.408 | 77 |
| Serum P4 | 0.763 | 59 | 0.907 | 49 |
| Serum P5 | 1.047 | 43 | — | |
| Serum P6 | 0.843 | 55 | — | |
| Serum P7 | 1.429 | 23 | — | |
| HBD 1 | 1.745 | 6 | 1.713 | 4 |
| HBD 2 | 1.807 | 2 | — | |
| HBD 3 | 1.779 | 4 | 1.626 | 9 |
| HBD 4 | 1.821 | 2 | — | |
| HBD 5 | 1.841 | 1 | 1.660 | 7 |
| HBD 6 | 1.762 | 5 | 1.777 | 0 |
| HBD 7 | 1.799 | 3 | 1.767 | 1 |
| HBD 8 | 1.783 | 4 | 1.703 | 4 |
| HBD 9 | 1.792 | 3 | 1.669 | 3 |

HBD = healthy blood donor serum
U/mL are units of NIBSC 90/672
Serum P1-P7 are from patients with Graves' disease

TABLE 5

Inhibition of TSH binding by WHO reference preparation NIBSC 90/672 and by hMAb TSHR1 IgG and Fab preparations

| | Samples diluted in serum[1] | | | | Samples diluted in assay buffer | | | |
|---|---|---|---|---|---|---|---|---|
| Sample | % inhibition | units/L | units/mg | mean units/mg | % inhibition | units/L | units/mg | mean units/mg |
| NIBSC 90/672 | | | | | | | | |
| 0.125 units/L | | | | | 2 | | | |
| 0.25 units/L | | | | | 4 | | | |
| 0.5 units/L | | | | | 11 | | | |
| 1.0 units/L | 15 | | | | 19 | | | |
| 2.0 units/L | 28 | | | | 38 | | | |
| 4.0 units/L | 48 | | | | 64 | | | |
| 8.0 units/L | 69 | | | | 83 | | | |
| 40.0 units/L | 95 | | | | 94 | | | |
| hMAb TSHR1 IgG | | | | | | | | |
| 0 ng/mL | 1 | | | | 0 | | | |
| 0.3 ng/mL | 1 | | | | 2 | | | |
| 1 ng/mL | 3 | | | | 3 | | | |
| 3 ng/mL | 7 | | | | 10 | 0.46 | | |
| 10 ng/mL | 21 | 1.48 | 148 | | 33 | 1.73 | 173 | |
| 30 ng/mL | 46 | 3.9 | 130 | 138 | 70 | 4.8 | 160 | 163 |
| 100 ng/mL | 81 | 13.5 | 135 | | 92 | 15.6 | 156 | |
| 300 ng/mL | 92 | | | | 95 | >40 | | |
| hMAb TSHR1 Fab | | | | | | | | |
| 0.3 ng/mL | 5 | | | | −2 | | | |
| 1 ng/mL | 5 | | | | 1 | | | |
| 3 ng/mL | 16 | 1.05 | 351 | | 16 | 0.8 | 265 | |
| 10 ng/mL | 36 | 2.77 | 277 | | 52 | 2.9 | 291 | 309 |
| 30 ng/mL | 69 | 8.0 | 267 | 288 | 86 | 9.6 | 372 | |
| 100 ng/mL | 89 | 23.7 | 237 | | 92 | 16.9 | | |
| 300 ng/mL | 93 | | | | 94 | | | |
| 2G4 IgG[2] | | | | | | | | |
| 0.3 ng/mL | 2 | | | | −3 | | | |
| 3 ng/mL | 1 | | | | −6 | | | |
| 30 ng/mL | 0 | | | | −5 | | | |
| 300 ng/mL | 3 | | | | −4 | | | |

TABLE 5-continued

Inhibition of TSH binding by WHO reference preparation
NIBSC 90/672 and by hMAb TSHR1 IgG and Fab preparations

| | Samples diluted in serum[1] | | | | Samples diluted in assay buffer | | | |
|---|---|---|---|---|---|---|---|---|
| Sample | % inhibition | units/L | units/mg | mean units/mg | % inhibition | units/L | units/mg | mean units/mg |
| 2G4 Fab[2] | | | | | | | | |
| 0.3 ng/mL | 4 | | | | −5 | | | |
| 3 ng/mL | 4 | | | | −6 | | | |
| 30 ng/mL | 1 | | | | −5 | | | |
| 300 ng/mL | 2 | | | | −6 | | | |

[1]Pool of healthy blood donor serum, 14.9% of total cpm bound to the TSHR in the presence of this serum pool only. 14.7% of total cpm bound to the TSHR in the presence of buffer only.
[2]2G4 is a human monoclonal autoantibody to thyroid peroxidase.

TABLE 6

Inhibition of TSH binding by lymphocyte donor serum and donor serum IgG

| | Samples diluted in serum[1] | | | | Samples diluted in assay buffer | | | |
|---|---|---|---|---|---|---|---|---|
| Sample | % inhibition | units/L[2] | units/mg or (units/mL in undiluted serum) | mean units/mg or (units/mL) | % inhibition | units/L[2] | units/mg or (units/mL in undiluted serum) | mean units/mg or (units/mL) |
| Donor serum | | | | | | | | |
| diluted 1000x | 6 | | | | 10 | | | |
| diluted 300x | 18 | 1.2 | (0.36) | | 28 | 1.3 | (0.39) | |
| diluted 100x | 42 | 3.2 | (0.32) | (0.36) | 62 | 3.9 | (0.39) | (0.40) |
| diluted 30x | 78 | 11.3 | (0.39) | | 91 | 13.5 | (0.41) | |
| diluted 10x | 93 | 34 | | | 95 | >40 | | |
| Donor serum IgG | | | | | | | | |
| 0 mg/mL | 0 | 0 | | | 0 | | | |
| 0.01 mg/mL | 7 | | | | 19 | 0.87 | | |
| 0.03 mg/mL | 23 | 1.6 | 0.053 | | 37 | 1.9 | 0.063 | |
| 0.1 mg/mL | 57 | 5.1 | 0.051 | 0.054 | 78 | 6.4 | 0.064 | 0.063 |
| 0.3 mg/mL | 85 | 17 | 0.057 | | 93 | 19 | 0.063 | |
| 1 mg/mL | 96 | 43 | | | 96 | >40 | | |
| Healthy blood donor pool serum | | | | | | | | |
| diluted 1000x | 0 | | | | 3 | | | |
| diluted 100x | 1 | | | | 4 | | | |
| diluted 10x | 1 | | | | 11 | | | |
| Healthy blood donor pool serum IgG | | | | | | | | |
| 0.01 mg/mL | 2 | | | | 2 | | | |
| 0.1 mg/mL | 1 | | | | 5 | | | |
| 1 mg/mL | 3 | | | | 7 | | | |

[1]Pool of healthy blood donor serum, 14.7% of total cpm bound to the TSHR in the presence of this serum pool only. 16.3% of total cpm bound to the TSHR in the presence of buffer only.
[2]Units shown are NIBSC 90/672 international TSHR autoantibody reference preparation.

TABLE 7

Specific activities of hMAb TSHR1 and lymphocyte donor serum and IgG preparations

| Preparation | Inhibition of TSH binding assay | | Stimulation of cyclic AMP assay | |
|---|---|---|---|---|
| | Units/mg[1,2] | Units/nmole[1,2] | Units/mg[1] | Units/nmole[1] |
| hMAb TSHR1 IgG | 150 | 22 | 180 | 26 |
| hMAb TSHR1 Fab | 300 | 15 | 700 | 35 |
| Donor serum IgG | 0.059 | 0.009 | 0.33 | 0.048 |
| Donor serum units/mL | 0.38 | | 1.8 | |

[1]Units shown are NIBSC 90/672.
[2]Values are a mean of results obtained in serum and in assay buffer (see Tables 5 and 6).

TABLE 8

Summary of specific activities of hMAb TSHR1 and lymphocyte donor serum and serum IgG determined in several stimulation of cyclic AMP assays

| Preparation | Mean Units per mg | Number of determinations | Standard Deviation |
|---|---|---|---|
| hMAb TSHR1 IgG | 318 | 16 | 189 |
| hMAb TSHR1 Fab | 492 | 10 | 184 |
| Donor serum IgG | 0.10 | 10 | 0.08 |
| Donor serum units/mL | 0.9 | 4 | 0.6 |

TABLE 9

Further analysis of the effects of hMAb TSHR1 IgG and Fab and lymphocyte donor serum IgG in the cyclic AMP stimulation assay

| Sample | Mean cyclic AMP per well (pmols) | number of determinations | Standard Deviation |
|---|---|---|---|
| hMAb TSHR1 IgG | | | |
| 0 ng/mL | 0.96 | 6 | 0.048 |
| 0.3 ng/mL | 1.25 | 6 | 0.12 |
| 1 ng/mL | 1.84 | 6 | 0.16 |
| 3 ng/mL | 3.4 | 5 | 0.37 |
| 10 ng/mL | 6.6 | 5 | 0.62 |
| hMAb TSHR1 Fab | | | |
| 0 ng/mL | 0.60 | 6 | 0.068 |
| 0.3 ng/mL | 1.11 | 6 | 0.11 |
| 1 ng/mL | 1.99 | 6 | 0.39 |
| 3 ng/mL | 4.9 | 6 | 0.44 |
| 10 ng/mL | 10.6 | 6 | 0.86 |
| Control human MAb (2G4)[1] | | | |
| IgG 0 ng/mL | 0.72 | 11 | 0.19 |
| IgG 10 ng/mL | 0.61 | 11 | 0.16 |
| Fab 10 ng/mL | 0.61 | 4 | 0.044 |
| Lymphocyte donor serum IgG | | | |
| 3 µg/mL | 1.67 | 6 | 0.38 |
| 10 µg/mL | 4.20 | 6 | 0.93 |
| 30 µg/mL | 6.22 | 6 | 0.73 |
| Healthy blood donor pool serum IgG | | | |
| 30 µg/mL | 0.38 | 6 | 0.10 |

[1]2G4 is a human monoclonal autoantibody to thyroid peroxidase

TABLE 10

Additive effect of TSH and hMAb TSHR1 IgG in stimulation of cyclic AMP assays

| Experiment 1 | | | Experiment 2 | | |
|---|---|---|---|---|---|
| | Sample | cyclic AMP[1] (pmols per well) | | Sample | cyclic AMP[1] (pmols per well) |
| A | Buffer only | 0.57 | A | Buffer only | 0.42 |
| B | Porcine TSH 0.1 ng/mL | 1.07 | B | Porcine TSH 0.05 ng/mL | 1.07 |
| C | hMAb TSHR1 1 ng/mL | 1.41 | C | hMAb TSHR1 0.5 ng/mL | 0.92 |
| B plus C | | 2.08 | B plus C | | 1.92 |

[1]Values shown are means of closely agreeing duplicate determinations

TABLE 11

Effects of NIBSC 90/672 in the cyclic AMP stimulation assay

| Sample | Mean cyclic AMP per well (pmols) | number of determinations | Standard Deviation |
|---|---|---|---|
| Buffer only | 0.60 | 6 | 0.068 |
| 0.1 units/L | 1.09 | 6 | 0.085 |
| 0.3 units/L | 1.49 | 5 | 0.11 |
| 1.0 units/L | 3.52 | 5 | 0.46 |
| 3.0 units/L | 8.16 | 6 | 1.39 |

TABLE 12

Inhibition of $^{125}$I-TSH binding to TSHR coated tubes by recombinant hMAb TSHR1 Fab expressed in 2 different *E coli* strains (XL1-Blue MRF' and HB2151 cells)

| Sample | Culture supernatant dilution[2] | % binding | % inhibition[3] |
|---|---|---|---|
| Assay buffer only[1] | | 12.1 | 0 |
| Untransformed XL1-Blue MRF' cell culture supernatant | 4x | 11.6 | 3.9 |
| | 8x | 11.5 | 4.5 |
| | 16x | 11.9 | 1.5 |
| | 32x | 11.9 | 1.5 |
| | 64x | 11.9 | 1.0 |
| | 128x | 12.1 | −0.5 |
| Transformed but non-induced XL1-Blue MRF' cell culture supernatant | 4x | 11.5 | 5.0 |
| | 8x | 11.6 | 4.2 |
| | 16x | 11.8 | 2.2 |
| | 32x | 11.1 | 8.4 |
| | 64x | 11.7 | 3.4 |
| | 128x | 11.1 | 8.0 |
| Transformed and induced XL1-Blue MRF' cell culture supernatant | 4x | 1.5 | 87.4 |
| | 8x | 2.3 | 81.3 |
| | 16x | 4.7 | 60.9 |
| | 32x | 7.2 | 40.2 |
| | 64x | 8.9 | 26.4 |
| | 128x | 10.3 | 14.8 |
| Untransformed HB2151 cell culture supernatant | x4 | 11.2 | 7.3 |
| | x8 | 11.1 | 8.1 |
| | x16 | 10.9 | 9.7 |
| | x32 | 10.8 | 10.2 |
| | x64 | 10.8 | 10.2 |
| | x128 | 10.6 | 12.3 |
| Transformed but non-induced HB2151 cell culture supernatant | 4x | 10.7 | 11.6 |
| | 8x | 10.5 | 13.3 |
| | 16x | 10.6 | 11.8 |
| | 32x | 10.7 | 11.4 |
| | 64x | 10.9 | 9.6 |
| | 128x | 10.6 | 11.8 |

TABLE 12-continued

Inhibition of $^{125}$I-TSH binding to TSHR coated tubes by recombinant hMAb TSHR1 Fab expressed in 2 different *E coli* strains (XL1-Blue MRF' and HB2151 cells)

| Sample | Culture supernatant dilution[2] | % binding | % inhibition[3] |
|---|---|---|---|
| Transformed and induced HB2151 cell culture supernatant | 4x | 1.0 | 92.0 |
| | 8x | 1.0 | 91.4 |
| | 16x | 1.3 | 89.0 |
| | 32x | 2.2 | 82.0 |
| | 64x | 4.3 | 64.1 |
| | 128x | 6.7 | 44.8 |

[1]Assay buffer = 50 mmol/L NaCl, 10 mmol/L Tris-HCl pH 7.8
[2]All dilutions were in assay buffer
[3]Inhibition of binding was calculated using the formula:

$$\% \text{ inhibition} = 100 - \left(\frac{A}{B} \times 100\right)$$

where A = binding in the presence of test sample
B = binding in the presence of assay buffer

TABLE 13

Stimulation of cAMP production in CHO cells transfected with the TSHR by recombinant hMAb TSHR1 Fab expressed in 2 different *E coli* strains (XL1-Blue MRF' and HB2151 cells)

| Sample | Culture supernatant dilution[2] | pmol/cell well | mean | x basal[3] |
|---|---|---|---|---|
| Assay buffer only[1] | | 0.54 | 0.49 | 1 |
| | | 0.44 | | |
| Untransformed XL1-Blue MRF' cell culture supernatant | 10x | 0.32 | 0.33 | 0.68 |
| | | 0.35 | | |
| Transformed but non-induced XL1-Blue MRF' cell culture supernatant | 10x | 0.52 | 0.62 | 1.3 |
| | | 0.73 | | |
| | 50x | 0.50 | 0.49 | 0.99 |
| | | 0.48 | | |
| Transformed and induced XL1-Blue MRF' cell culture supernatant | 10x | >6.4 | >6.4 | >13.1 |
| | | >6.4 | | |
| | 50x | 3.5 | 3.6 | 7.3 |
| | | 3.6 | | |
| Untransformed HB2151 cell culture supernatant | 10x | 0.39 | 0.37 | 0.76 |
| | | 0.35 | | |
| Transformed but non-induced HB2151 cell culture supernatant | 10x | 0.29 | 0.37 | 0.76 |
| | | 0.45 | | |
| | 50x | 0.37 | 0.37 | 0.76 |
| | | 0.37 | | |
| Transformed and induced HB2151 cell culture supernatant | 10x | >6.4 | >6.4 | >13.1 |
| | | >6.4 | | |
| | 50x | >6.4 | >6.4 | >13.1 |
| | | >6.4 | | |

[1]Assay buffer = Hanks' buffered salt solution (NaCl free) containing 1 g/L glucose, 20 mmol/L HEPES, 222 mmol/L sucrose, 15 g/L bovine serum albumin (BSA) and 0.5 mmol/L 2 isobutyl-1-methyl xanthine pH 7.4
[2]Dilutions in assay buffer
[3]Basal = cAMP produced in the presence of assay buffer only

TABLE 14

Inhibition of $^{125}$I-TSH binding to TSHR coated tubes by recombinant hMAb TSHR1 Fab, recombinant 4B4 Fab (a human MAb to GAD) and recombinant hybrid Fabs (mixed HC and LC of the 2 Fabs). Expression in *E coli* HB2151 cells
ASSAYS OF PERIPLASMIC FRACTIONS

| Test sample | Periplasmic fraction (PF) dilution and (total Fab concentration in undiluted PF) | % $^{125}$I-TSH binding | % inhibition[1] |
|---|---|---|---|
| Assay buffer only | | 11.5 | 0 |
| Untransformed cells | 4x (ud) | 11.8 | −2.7 |
| | 8x | 11.8 | −2.7 |
| | 16x | 12.2 | −5.9 |
| hMAb TSHR1 HC/LC transformed but non-induced cells | 4x (177 ng/mL) | 1.6 | 86[a] |
| | 8x | 3.6 | 68 |
| | 16x | 6.4 | 45 |
| hMAb TSHR1 HC/LC transformed and induced cells | 4x (364 ng/mL) | 0.95 | 92 |
| | 8x | 1.4 | 88 |
| | 16x | 2.7 | 77 |
| hMAb TSHR1 HC/4B4 LC transformed but non-induced cells | 4x (ud) | 12.0 | −3.9 |
| | 8x | 12.1 | −4.8 |
| | 16x | 12.4 | −7.8 |
| hMAb TSHR1 HC/4B4 LC transformed and induced cells | 4x (83 ng/mL) | 11.4 | 0.9 |
| | 8x | 11.8 | −2.1 |
| | 16x | 11.7 | −1.8 |
| 4B4 HC/hMAb TSHR1 LC transformed but non-induced cells | 4x (ud) | 11.9 | −3.5 |
| | 8x | 12.2 | −6.1 |
| | 16x | 12.4 | −7.8 |
| 4B4 HC/hMAb TSHR1 LC transformed and induced cells | 4x (850 ng/mL) | 11.8 | −2.8 |
| | 8x | 11.2 | 3.1 |
| | 16x | 11.9 | −3.2 |
| 4B4 HC/LC transformed but non induced cells | 4x (ud) | 12.1 | −5.4 |
| | 8x | 12.0 | −4.0 |
| | 16x | 12.1 | −4.8 |
| 4B4 HC/LC transformed and induced cells | 4x (265 ng/mL) | 11.7 | −1.2 |
| | 8x | 11.7 | −1.4 |
| | 16x | 12.0 | −4.2 |

[1]Inhibition of binding was calculated using the formula:

$$\% \text{ inhibition} = 100 - \left(\frac{A}{B} \times 100\right)$$

where A = % $^{125}$I-TSH binding in the presence of test sample
B = % $^{125}$I-TSH binding in the presence of assay buffer
[a]Detection of TSHR Ab activity in the non-induced cells was due to constitutive activity of the promoter giving low level expression of Fab in the absence of IPTG.
ud = undetectable

TABLE 15

Inhibition of $^{125}$I-TSH binding to TSHR coated tubes by recombinant hMAb TSHR1 Fab, recombinant 4B4 Fab (a human MAb to GAD) and recombinant hybrid Fabs (mixed HC and LC of the 2 Fabs). Expression in *E coli* HB2151 cells
ASSAYS OF CULTURE SUPERNATANTS

| Test sample | Culture supernatant dilution and (total Fab concentration in undiluted supernatant) | % $^{125}$I-TSH binding | % inhibition[1] |
|---|---|---|---|
| Assay buffer only | | 11.1 | 0 |
| Untransformed cells | 4x (ud) | 11.8 | −6.5 |
| | 8x | 13.1 | −18 |
| | 16x | 11.1 | −0.3 |
| hMAb TSHR1 HC/LC transformed but non-induced cells | 4x (ud) | 10.8 | 2.1 |
| | 8x | 12.1 | −9.8 |
| | 16x | 11.9 | −8.1 |
| hMAb TSHR1 HC/LC transformed and induced cells | 4x (421 ng/mL) | 1.1 | 91 |
| | 8x | 1.2 | 90 |
| | 16x | 1.1 | 90 |
| hMAb TSHR1 HC/4B4 LC transformed but non-induced cells | 4x (ud) | 11.8 | −7.0 |
| | 8x | 12.5 | −13.0 |
| | 16x | 12.0 | −1.3 |

TABLE 15-continued

Inhibition of $^{125}$I-TSH binding to TSHR coated tubes by recombinant hMAb TSHR1 Fab, recombinant 4B4 Fab (a human MAb to GAD) and recombinant hybrid Fabs (mixed HC and LC of the 2 Fabs). Expression in *E coli* HB2151 cells
ASSAYS OF CULTURE SUPERNATANTS

| Test sample | Culture supernatant dilution and (total Fab concentration in undiluted supernatant) | | % $^{125}$I-TSH binding | % inhibition[1] |
|---|---|---|---|---|
| hMAb TSHR1 HC/4B4 LC transformed and induced cells | 4x<br>8x<br>16x | (262 ng/mL) | 10.8<br>11.1<br>11.3 | 2.7<br>−0.4<br>−2.6 |
| 4B4 HC/hMAb TSHR1 LC transformed but non-induced cells | 4x<br>8x<br>16x | (ud) | 11.9<br>12.7<br>11.8 | −7.4<br>−15<br>−7.0 |
| 4B4 HC/hMAb TSHR1 LC transformed and induced cells | 4x<br>8x<br>16x | (84 ng/mL) | 10.5<br>10.8<br>11.2 | 4.8<br>2.4<br>−0.9 |
| 4B4 HC/LC transformed but non-induced cells | 4x<br>8x<br>16x | (ud) | 11.9<br>12.6<br>12.0 | −7.5<br>−14<br>−9.0 |
| 4B4 HC/LC transformed and induced cells | 4x<br>8x<br>16x | (522 ng/mL) | 10.5<br>11.0<br>11.0 | −4.7<br>0.7<br>0.5 |

[1]see footnote to Table 14
ud = undetectable

TABLE 16

Stimulation of cyclic AMP production in CHO Cells transfected with the TSHR by recombinant hMAb TSHR1 Fab, recombinant 4B4 Fab (a human MAb to GAD) and recombinant hybrid Fabs (mixed HC and LC of the 2 Fabs). Expression in *E coli* HB2151 cells
ASSAYS OF CULTURE SUPERNATANTS

| Test sample[1] | Dilution[2] of culture supernatant and (total Fab concentration in undiluted supernatants) | | pmol cyclic AMP/cell well | mean pmol cyclic AMP/cell well | x basal stimulation[3] |
|---|---|---|---|---|---|
| Assay buffer[1] only | | | 0.35<br>0.25<br>0.33 | 0.31 | 1 |
| Untransformed cells | 10x | (ud) | 0.51<br>0.67<br>0.48 | 0.55 | 1.8 |
| hMAb TSHR1 HC/LC transformed but non-induced cells | 10x | (ud) | 0.84<br>1.80<br>2.13 | 1.59 | 5.1[a] |
| hMAb TSHR1 HC/LC transformed and induced cells | 10x | (421 ng/mL) | >6.4<br>>6.4<br>>6.4 | >6.4 | >20 |
| hMAb TSHR1 HC/4B4 LC transformed but non-induced cells | 10x | (ud) | 0.55<br>0.63<br>0.58 | 0.59 | 1.9 |
| hMAb TSHR1 HC/4B4 LC transformed and induced cells | 10x | (262 ng/mL) | 0.47<br>0.47<br>0.52 | 0.48 | 1.6 |
| 4B4 HC/hMAb TSHR1 LC transformed but non-induced cells | 10x | (ud) | 0.65<br>0.59<br>0.60 | 0.61 | 2.0 |
| 4B4 HC/hMAb TSHR1 LC transformed and induced cells | 10x | (84 ng/mL) | 0.51<br>0.37<br>0.38 | 0.42 | 1.4 |
| 4B4 HC/LC transformed but non induced cells | 10x | (ud) | 0.65<br>0.73<br>0.64 | 0.67 | 2.2 |
| 4B4 HC/LC transformed and induced cells | 10x | (522 ng/mL) | 0.55<br>0.41<br>0.35 | 0.44 | 1.4 |

[1]Assay buffer: Hanks' buffered salt solution (NaCl free) containing 1 g/L glucose, 20 mmol/L HEPES, 222 mmol/L sucrose, 15 g/L bovine serum albumin (BSA) and 0.5 mmol/L 2 isobutyl-1-methyl xanthine pH 7.4
[2]Dilutions in assay buffer
[3]Basal = cyclic AMP production in the presence of assay buffer only
[a]Detection of cyclic AMP stimulation activity in the non-induced cells was due to constitutive activity of the promoter giving low level expression of Fab in the absence of IPTG. Total recombinant Fab levels were undetectable (detection limit = 5-10 ng/mL) whereas the stimulation of cyclic AMP assay can detect as little as 0.3 ng/mL of hMAb TSHR1 Fab.
ud = undetectable

TABLE 17

Stimulation of cyclic AMP production in CHO Cells transfected with the TSHR by recombinant hMAb TSHR1 Fab, recombinant 4B4 Fab (a human MAb to GAD) and recombinant hybrid Fabs (mixed HC and LC of the 2 Fabs), Expression in *E coli* HB2151 cells
ASSAYS OF PERIPLASMIC FRACTIONS

| Test sample | Periplasmic fraction (PF) dilution[2] and (total Fab concentration in undiluted PF) | | pmol cyclic AMP/cell well | mean pmol cyclic AMP/ cell well | x basal stimulation[3] |
|---|---|---|---|---|---|
| Assay buffer[1] only | | | 0.35 | 0.31 | 1 |
| | | | 0.25 | | |
| | | | 0.33 | | |
| Untransformed cells | 10x | (ud) | 0.31 | 0.29 | 0.9 |
| | | | 0.22 | | |
| | | | 0.35 | | |
| hMAb TSHR1 HC/LC transformed but non-induced cells | 10x | (177 ng/mL) | >6.4 | >6.4 | >20.6[a] |
| | | | >6.4 | | |
| | | | >6.4 | | |
| hMAb TSHR1 HC/LC transformed and induced cells | 10x | (364 ng/mL) | >6.4 | >6.4 | >20.6 |
| | | | >6.4 | | |
| | | | — | | |
| hMAb TSHR1 HC/4B4 LC transformed but non-induced cells | 10x | (ud) | 0.40 | 0.35 | 1.1 |
| | | | 0.33 | | |
| | | | 0.33 | | |
| hMAb TSHR1 HC/4B4 LC transformed and induced cells | 10x | (83 ng/mL) | 0.31 | 0.34 | 1.1 |
| | | | 0.31 | | |
| | | | 0.41 | | |
| 4B4 HC/hMAb TSHR1 LC transformed but non-induced cells | 10x | (ud) | 0.29 | 0.30 | 1.0 |
| | | | 0.31 | | |
| | | | 0.29 | | |
| 4B4 HC/hMAb TSHR1 LC transformed and induced cells | 10x | (850 ng/mL) | 0.23 | 0.24 | 0.8 |
| | | | 0.25 | | |
| | | | 0.24 | | |
| 4B4 HC/LC transformed but non induced cells | 10x | (ud) | 0.33 | 0.32 | 1.0 |
| | | | 0.35 | | |
| | | | 0.29 | | |
| 4B4 HC/LC transformed and induced cells | 10x | (265 ng/mL) | 0.40 | 0.37 | 1.2 |
| | | | 0.38 | | |
| | | | 0.32 | | |
| hMAb TSHR1 IgG 1 ng/ml (hybridoma produced) | | | 2.0 | 2.0 | 6.4 |
| | | | 2.0 | | |
| | | | 2.0 | | | ud = undetectable;
[1,2,3] see footnote to Table 16
[a] Detection of TSHRAb activity in the non-induced cells was due to constitutive activity of the promoter giving low level expression in the absence of IPTG.

TABLE 18

Inhibition of 4B4 IgG (a hybridoma produced human MAb to GAD) binding to $^{125}$I-GAD by recombinant hMAb TSHR1 Fab, recombinant 4B4 Fab and recombinant hybrid Fab's (mixed HC and LC of the 2 Fabs). Expression in *E coli* HB2151 cells
ASSAYS OF PERIPLASMIC FRACTIONS

| Test sample added with 4B4 IgG and $^{125}$I-GAD | Periplasmic fraction (PF) dilution and (total Fab concentration in undiluted PF) | % $^{125}$I-GAD binding | % inhibition[1] |
|---|---|---|---|
| GAD Ab Assay buffer | | 28 | 0 |
| 4B4 F(ab')2 (hybridoma produced) | 1 µg/ml | 5.5 | 80 |
| | 0.1 µg/ml | 12 | 57 |
| | 0.01 µg/ml | 24 | 14 |
| | 0.001 µg/ml | 29 | -3.9 |
| Untransformed cells | 4x (ud) | 27 | 0.9 |
| | 8x | 28 | -1.7 |
| | 16x | 29 | -6.3 |
| hMAb TSHR1 HC/LC transformed but non-induced cells | 4x (177 ng/mL) | 28 | -2.6 |
| | 8x | 28 | -0.5 |
| | 16x | 28 | -0.8 |
| hMAb TSHR1 HC/LC transformed and induced cells | 4x (364 ng/mL) | 27 | 0.7 |
| | 8x | 27 | 1.4 |
| | 16x | 29 | -4.2 |
| hMAb TSHR1 HC/4B4 LC transformed but non-induced cells | 4x (ud) | 28 | -1.1 |
| | 8x | 28 | -0.2 |
| | 16x | 27 | 1.1 |
| hMAb TSHR1 HC/4B4 LC transformed and induced cells | 4x (83 ng/mL) | 28 | -1.4 |
| | 8x | 28 | -0.7 |
| | 16x | 28 | -2.4 |
| 4B4 HC/hMAb TSHRI LC transformed but non-induced cells | 4x (ud) | 28 | -2.9 |
| | 8x | 28 | -3.2 |
| | 16x | 28 | -3.1 |
| 4B4 HC/hMAb TSHR1 LC transformed and induced cells | 4x (850 ng/mL) | 27 | 1.7 |
| | 8x | 28 | -0.2 |
| | 16x | 28 | -1.0 |

TABLE 18-continued

Inhibition of 4B4 IgG (a hybridoma produced human MAb to GAD) binding to $^{125}$I-GAD by recombinant hMAb TSHR1 Fab, recombinant 4B4 Fab and recombinant hybrid Fab's (mixed HC and LC of the 2 Fabs). Expression in *E coli* HB2151 cells
ASSAYS OF PERIPLASMIC FRACTIONS

| Test sample added with 4B4 IgG and $^{125}$I-GAD | Periplasmic fraction (PF) dilution and (total Fab concentration in undiluted PF) | % $^{125}$I-GAD binding | % inhibition[1] |
|---|---|---|---|
| 4B4 HC/LC transformed but non induced cells | 4x (ud) | 29 | −4.4 |
| | 8x | 28 | −1.5 |
| | 16x | 27 | 1.7 |
| 4B4 HC/LC transformed and induced cells | 4x (265 ng/mL) | 21 | 23.2 |
| | 8x | 24 | 12.5 |
| | 16x | 26 | 5.6 |

[1]Inhibition of binding was calculated using the formula:

$$\% \text{ inhibition} = 100 - \left(\frac{A}{B} \times 100\right)$$

where A = $^{125}$I-GAD binding in the presence of test sample
B = $^{125}$I-GAD binding in the presence of assay buffer
ud = undetectable

TABLE 19

Inhibition of 4B4 IgG (a hybridoma produced human MAb to GAD) binding to $^{125}$I-GAD by recombinant hMAb TSHR1 Fab, recombinant 4B4 Fab and recombinant hybrid Fabs (mixed HC and LC of the 2 Fabs). Expression in *E coli* HB2151
ASSAYS OF CULTURE SUPERNATANTS

| Test sample added with 4B4 IgG and $^{125}$I-GAD | Culture supernatant dilution and (total Fab concentration in undiluted supernatant) | % $^{125}$I-GAD binding | % inhibition[1] |
|---|---|---|---|
| Assay buffer | | 26 | 0 |
| 4B4 F(ab')$_2$ | 1 µg/ml | 5.2 | 80 |
| (hybridoma | 0.1 µg/ml | 11 | 58 |
| produced) | 0.01 µg/ml | 22 | 15 |
| | 0.001 µg/ml | 28 | −5.2 |
| Untransformed HB2151 cells | 4x (ud) | 28 | −5.5 |
| | 8x | 29 | −9.1 |
| | 16x | 28 | −6.3 |
| hMAb TSHR1 HC/LC transformed but non-induced cells | 4x (ud) | 28 | −7.0 |
| | 8x | 29 | −9.5 |
| | 16x | 28 | −5.2 |
| hMAb TSHR1 HC/LC transformed and induced cells | 4x (421 ng/mL) | 28 | −7.0 |
| | 8x | 28 | −6.4 |
| | 16x | 28 | −5.6 |
| hMAb TSHR1 HC/4B4 LC transformed but non-induced cells | 4x (ud) | 29 | −9.0 |
| | 8x | 29 | −7.9 |
| | 16x | 28 | −7.6 |
| hMAb TSHR1 HC/4B4 LC transformed and induced cells | 4x (262 ng/mL) | 27 | −2.2 |
| | 8x | 28 | −5.5 |
| | 16x | 28 | −5.1 |
| 4B4 HC/hMAb TSHR1 LC transformed but non-induced cells | 4x (ud) | 28 | −4.4 |
| | 8x | 28 | −7.0 |
| | 16x | 28 | −5.5 |
| 4B4 HC/hMAb TSHR1 LC transformed and induced cells | 4x (84 ng/mL) | 27 | −2.0 |
| | 8x | 28 | −5.7 |
| | 16x | 27 | −2.5 |
| 4B4 HC/LC transformed but non induced cells | 4x (ud) | 28 | −4.8 |
| | 8x | 28 | −4.8 |
| | 16x | 27 | −1.7 |
| 4B4 HC/LC transformed and induced cells | 4x (522 ng/mL) | 11 | 59 |
| | 8x | 14 | 46 |
| | 16x | 17 | 34 |

[1]see footnote to Table 18
ud = undetectable

TABLE 20

Effects of mouse monoclonal antibodies to the TSHR on hMAb TSHR1 induced stimulation of cyclic AMP production in CHO cells expressing the TSHR

| Test sample[1] | pmol cyclic AMP/cell well | mean pmol cyclic AMP/cell well | SD | x basal stimulation[2] |
|---|---|---|---|---|
| hMAb TSHR1 Fab 5 ng/mL plus: - | | | | |
| (a) Assay buffer[1] | 3.252 | 2.835 | — | 3.9 |
| | 2.418 | | | |
| (b) 2G2[3] | 4.278 | 3.595 | 0.496 | 4.9 |
| | 3.392 | | | |
| | 3.116 | | | |
| (c) 2B4[4] | 3.320 | 2.939 | 0.286 | 4.0 |
| | 2.632 | | | |
| | 2.864 | | | |
| (d) 9D33[4] | 0.506 | 0.443 | 0.047 | 0.61 |
| | 0.394 | | | |
| | 0.428 | | | |
| Assay buffer alone[1] | 0.696 | 0.727 | 0.02 | 1 |
| | 0.742 | | | |
| | 0.742 | | | |
| 2G2 alone[3] | 0.252 | 0.311 | 0.051 | 0.43 |
| | 0.306 | | | |
| | 0.376 | | | |
| 2B4 alone[4] | 0.298 | 0.331 | 0.033 | 0.46 |
| | 0.318 | | | |
| | 0.376 | | | |
| 9D33 alone[4] | 0.280 | 0.313 | 0.025 | 0.43 |
| | 0.318 | | | |
| | 0.340 | | | |

[1]All dilutions were made in assay buffer (Hanks' buffered salt solution (NaCl free) containing 1 g/L glucose, 20 mmol/L HEPES, 222 mmol/L sucrose, 15 g/L bovine serum albumin (BSA) and 0.5 mmol/L 2 isobutyl-1-methyl xanthine pH 7.4)
[2]Basal = cyclic AMP production in the presence of assay buffer only
[3]2G2 is a mouse monoclonal antibody to thyroglobulin (100 µg/mL of IgG preparation)
[4]2B4 and 9D33 are mouse monoclonal antibodies to the TSHR (100 µg/mL of IgG preparations)

TABLE 21

Effects of mouse monoclonal antibodies to the TSHR on pTSH induced stimulation of cyclic AMP production in CHO cells expressing the TSHR

| Test sample[1] | pmol cyclic AMP/cell well | mean pmol cyclic AMP/cell well | SD | x basal stimulation[2] |
|---|---|---|---|---|
| pTSH 0.5 ng/mL plus: - | | | | |
| (a) Assay buffer[1] | 4.016 | 3.91 | 0.91 | 11.5 |
| | 2.746 | | | |
| | 4.960 | | | |
| (b) 2B4[4] | 0.878 | 0.78 | 0.07 | 2.3 |
| | 0.710 | | | |
| | 0.742 | | | |
| (c) 9D33[4] | 0.436 | 0.43 | 0.01 | 1.3 |
| | 0.436 | | | |
| | 0.410 | | | |
| Assay buffer alone[1] | 0.384 | 0.34 | 0.03 | 1 |
| | 0.318 | | | |
| | 0.318 | | | |
| 2B4 alone[4] | 0.446 | 0.49 | 0.04 | 1.4 |
| | 0.486 | | | |
| | 0.552 | | | |
| 9D33 alone[4] | 0.332 | 0.33 | 0.02 | 0.97 |
| | 0.362 | | | |
| | 0.304 | | | |

[1,2,4]See footnotes for Table 20. In a separate experiment a control mouse MAb to thyroglobulin (2G2 IgG 100 µg/mL) was shown to have no effect on pTSH (0.5 ng/mL) stimulation of cyclic AMP production (pTSH plus assay buffer = 12.7 × basal; pTSH plus 2G2 = 11.7 × basal)

TABLE 22

Inhibition by various MAbs of $^{125}$I-TSH, $^{125}$I-hMAb TSHR1 or $^{125}$I-9D33 binding to TSHR coated tubes

| Test IgG and concentration (µg/mL)[1] | | Inhibition of $^{125}$I-TSH binding[2] | Inhibition of $^{125}$I-hMAb TSHR1 binding[2] | Inhibition of $^{125}$I-9D33 binding[2] |
|---|---|---|---|---|
| 9D33 IgG | 0.001 | 0 | 0 | 4 |
| | 0.01 | 17 | 3 | 9 |
| | 0.1 | 34 | 21 | 35 |
| | 1 | 58 | 44 | 64 |
| | 10 | 68 | 56 | 71 |
| 2B4 IgG | 0.001 | 15 | 0 | 4 |
| | 0.01 | 36 | 0 | 5 |
| | 0.1 | 62 | 0 | 15 |
| | 1 | 83 | 11 | 22 |
| | 10 | 85 | 18 | 22 |
| hMAb TSHR1 IgG | 0.001 | 13 | 41 | 1.1 |
| | 0.01 | 60 | 70 | 18 |
| | 0.1 | 89 | 88 | 72 |
| | 1 | 94 | 93 | 90 |
| | 10 | 95 | 94 | 93 |

[1] All dilutions were in a pool of healthy blood donor sera (HBD pool)
[2] Inhibition of binding was calculated using the formula:

$$\% \text{ inhibition} = 100 - \left(\frac{A}{B} \times 100\right)$$

where A = % binding in the presence of test sample
B = % binding in the presence of HBD pool
The control mouse MAb to thyroglobulin (2G2 0.001-100 µg/mL) had no effect on the binding of labelled TSH, hMAb TSHR1 or 9D33

TABLE 23

Effect of patient sera on $^{125}$I-9D33 binding and $^{125}$I-TSH binding to TSHR coated tubes

| Test serum[1] | $^{125}$I-9D33 bound (% total counts added) | Inhibition of $^{125}$I-9D33 binding (%)[2] | Inhibition of $^{125}$I-TSH binding (%)[2] |
|---|---|---|---|
| HBD pool | 11 | 0 | 0 |
| G1 | 2.2 | 79 | 90 |
| G2 | 4.3 | 74 | 59 |
| G3 | 3.2 | 69 | 78 |
| G4 | 5.8 | 45 | 50 |
| G5 | 4.0 | 62 | 78 |
| G6 | 5.1 | 67 | 51 |
| G7 | 5.9 | 44 | 74 |
| G8 | 2.6 | 75 | 82 |
| G9 | 2.0 | 81 | 90 |
| G10 | 5.5 | 48 | 62 |
| G11 | 3.1 | 62 | 59 |
| G12 | 4.0 | 43 | 51 |
| G13 | 6.0 | 50 | 59 |
| G14 | 5.3 | 71 | 80 |
| G15 | 3.1 | 77 | 98 |
| G16 | 2.4 | 80 | 93 |
| G17 | 2.1 | 84 | 94 |
| G18 | 1.7 | 73 | 83 |
| G19 | 2.9 | 80 | 94 |
| G20 | 2.1 | 71 | 80 |
| A1 | 10 | 1.9 | 0 |
| A2 | 10 | 2.3 | 0 |
| D1 | 11 | 0 | 0 |
| D2 | 10 | 4.5 | 0 |
| N1 | 12 | −15 | 6.7 |
| N2 | 7.9 | 25 | 4.1 |
| N3 | 11 | 0 | 6.3 |
| N4 | 11 | −5.0 | 6.5 |
| N5 | 9.1 | 14 | 6.3 |
| N6 | 11 | −2.1 | 7.2 |
| N7 | 14 | −37 | −1.4 |
| N8 | 11 | −2.1 | 5.9 |
| N9 | 12 | −9.8 | 6.7 |

[1] HBD pool = pool of healthy blood donor sera
G1-G20 are sera from patients with Graves' disease
D1 and D2 are from patients with type 1 diabetes mellitus (positive for autoantibodies to glutamic acid decarboxylase)
A1 and A2 are from patients with Addison's disease (positive for steroid 21-hydroxylase autoantibodies)
N1-N9 are from individual healthy blood donors
[2] Inhibition of binding was calculated using the formula:

$$\% \text{ inhibition} = 100 - \left(\frac{A}{B} \times 100\right)$$

where A = % binding in the presence of test serum
B = % binding in the presence of a pool of healthy blood donor sera

TABLE 24

Effect of patient sera with TSH agonist and TSH antagonist activities on $^{125}$I-9D33 binding to TSHR coated tubes

| Test sample and dilution[1] | | $^{125}$I-9D33 bound (% total counts added) | Inhibition of $^{125}$I-9D33 binding (%)[2] |
|---|---|---|---|
| HBD pool | | 11 | 0 |
| Serum A | 1:320 | 6.4 | 39 |
| | 1:160 | 4.7 | 55 |
| | 1:80 | 3.3 | 69 |
| | 1:40 | 2.8 | 73 |
| | 1:20 | 2.4 | 77 |
| | 1:10 | 2.0 | 82 |
| Serum B | 1:320 | 9.1 | 13 |
| | 1:160 | 8.3 | 21 |
| | 1:80 | 6.4 | 39 |
| | 1:40 | 4.9 | 53 |
| | 1:20 | 3.8 | 64 |
| | 1:10 | 2.5 | 76 |
| Serum C | 1:320 | 9.7 | 7.6 |
| | 1:160 | 8.9 | 15 |
| | 1:80 | 8.0 | 24 |
| | 1:40 | 6.3 | 40 |
| | 1:20 | 5.1 | 51 |
| | 1:10 | 3.7 | 65 |
| Serum D | 1:320 | 9.4 | 11 |
| | 1:160 | 8.2 | 22 |
| | 1:80 | 7.2 | 32 |
| | 1:40 | 5.2 | 51 |
| | 1:20 | 4.3 | 59 |
| | 1:10 | 3.3 | 69 |

[1] HBD pool = pool of healthy blood donor sera, test sera were diluted in this pool sera A and B have TSH antagonist activity sera C and D have TSH agonist activity
[2] Inhibition of binding was calculated with the formula used in Table 23

TABLE 25

Effect of NIBSC 90/672 on $^{125}$I-9D33 binding and $^{125}$I-TSH binding to TSHR coated tubes

| Concentration of 90/672[1] | $^{125}$I-9D33 bound (% total counts added) | Inhibition of $^{125}$I-9D33 binding[2] (%) | Inhibition of $^{125}$I-TSH binding[2] (%) |
|---|---|---|---|
| 40 U/L | 4.1 | 72 | 92 |
| 8 U/L | 7.1 | 52 | 68 |

TABLE 25-continued

Effect of NIBSC 90/672 on $^{125}$I-9D33 binding and $^{125}$I-TSH binding to TSHR coated tubes

| Concentration of 90/672[1] | $^{125}$I-9D33 bound (% total counts added) | Inhibition of $^{125}$I-9D33 binding[2] (%) | Inhibition of $^{125}$I-TSH binding[2] (%) |
|---|---|---|---|
| 2 U/L | 11 | 28 | 23 |
| 1 U/L | 13 | 10 | 12 |
| 0 U/L | 15 | 0 | 0 |

[1]90/672 diluted in a pool of healthy blood donor sera
[2]Inhibition of binding was calculated with the formula used in Table 23

TABLE 26

Inhibition of $^{125}$I-hMAb TSHR1 Fab binding to TSHR coated tubes by polyclonal hMAb TSHR1 anti idiotypic antibodies in sera from a mouse immunised with hMAb TSHR1 Fab

| Test sample | Dilution[1] of test sample | % inhibition[2] of $^{125}$I-hMAb TSHR1 Fab binding to the TSHR |
|---|---|---|
| Assay buffer |  | 0 |
| Sera from a mouse immunised with hMAb TSHR1 Fab | 1:100 000 | 1.3 |
|  | 1:50 000 | 7.9 |
|  | 1:10 000 | 49.8 |
|  | 1:5 000 | 73.0 |
|  | 1:1 000 | 94.8 |

TABLE 26-continued

Inhibition of $^{125}$I-hMAb TSHR1 Fab binding to TSHR coated tubes by polyclonal hMAb TSHR1 anti idiotypic antibodies in sera from a mouse immunised with hMAb TSHR1 Fab

| Test sample | Dilution[1] of test sample | % inhibition[2] of $^{125}$I-hMAb TSHR1 Fab binding to the TSHR |
|---|---|---|
| Non-immunised mouse serum | 1:500 | −0.8 |

[1]Test samples diluted in assay buffer. Binding in the presence of assay buffer was 43%
[2]Inhibition of binding was calculated using the formula:

$$\% \text{ inhibition} = 100 - \left(\frac{A}{B} \times 100\right)$$

where A = % $^{125}$I-hMAb TSHR1 Fab binding in the presence of test sample
B = % $^{125}$I-hMAb TSHR1 Fab binding in the presence of assay buffer

TABLE 27

Inhibition of $^{125}$I-hMAb TSHR1 Fab binding to TSHR coated tubes by a mouse monoclonal anti idiotypic antibody 7E51 IgG

| Test sample |  | % binding of $^{125}$I-hMAb TSHR1 Fab to the TSHR | % inhibition[1] of $^{125}$I-hMAb TSHR1 Fab binding |
|---|---|---|---|
| Assay buffer alone |  | 16.3 | 0 |
| 7E51 IgG | 1 µg/mL | 14.5 | 11.0 |
| diluted in | 10 µg/mL | 6.4 | 60.7 |
| assay buffer | 100 µg/mL | 1.7 | 89.4 |

[1]see footnote to Table 26

The invention claimed is:

1. An isolated or purified binding partner comprising an antibody or one or more antibody fragments, wherein
   (a) the binding partner binds to human TSH receptor;
   (b) the binding partner inhibits TSH binding to the human TSH receptor; and
   (c) the binding partner competes with hMAb TSHR1 (Seq ID Nos. 1-9) for binding to the TSH receptor, wherein the binding partner has an inhibitory activity with respect to $^{125}$I-labeled TSH binding to the TSH receptor of at least 15 units of International Standard NIBSC 90/672 per mg.

2. The binding partner of claim 1, wherein the binding partner has an inhibitory activity with respect to $^{125}$I-labeled TSH binding to the TSH receptor of at least 30 units of International Standard NIBSC 90/672 per mg.

3. The binding partner of claim 1, wherein the binding partner has an inhibitory activity with respect to $^{125}$I-labeled TSH binding to the TSH receptor of at least 120 units of International Standard NIBSC 90/672 per mg.

4. The binding partner of claim 1, wherein the binding partner has a stimulatory activity with respect to cAMP production by cells expressing the TSH receptor, of at least 30 units of International Standard NIBSC 90/672 per mg.

5. The binding partner of claim 4, wherein the binding partner has a stimulatory activity with respect to cAMP production by cells expressing the TSH receptor, of at least 60 units of International Standard NIBSC 90/672 per mg.

6. The binding partner of claim 4, wherein the binding partner has a stimulatory activity with respect to cAMP production by cells expressing the TSH receptor, of at least 120 units of International Standard NIBSC 90/672 per mg.

7. The binding partner of claim 1, comprising Seq ID No. 19.

8. The binding partner of claim 7, further comprising Seq ID No. 24.

9. The binding partner of claim 7, further comprising one or more of Seq ID Nos. 25, 26 and 27.

10. The binding partner of claim 1, comprising one or more of Seq ID Nos. 20, 21 and 22.

11. The binding partner of claim 10, further comprising Seq ID No. 24.

12. The binding partner of claim 10, further comprising one or more of Seq ID Nos. 25, 26 and 27.

13. The binding partner of claim 1, comprising Seq ID No. 24.

14. The binding partner of claim 1, comprising one or more of Seq ID Nos. 25, 26 and 27.

15. The binding partner of claim of claim 1, wherein the binding partner is an antibody comprising Seq ID Nos. 20-23 and 25-28.

16. The binding partner of claim 1, wherein the binding partner has an inhibitory activity with respect to $^{125}$I-labeled TSH binding to the TSH receptor of at least 60 units of International Standard NIBSC 90/672 per mg.

17. An isolated or purified nucleic acid encoding a binding partner comprising an antibody or one or more antibody fragments, wherein
   (a) the binding partner binds to human TSH receptor;
   (b) the binding partner inhibits TSH binding to the human TSH receptor; and
   (c) the binding partner competes with hMAb TSHR1 (Seq ID Nos. 1-9) for binding to the TSH receptor, wherein the binding partner has an inhibitory activity with respect to $^{125}$I-labeled TSH binding to the TSH receptor of at least 15 units of International Standard NIBSC 90/672 per mg.

18. The isolated or purified nucleic acid of claim 17, wherein the nucleic acid encodes an amino acid sequence comprising one or more of Seq ID Nos. 19-27.

19. The isolated or purified nucleic acid of claim 18, wherein the nucleic acid comprises one or more of Seq ID Nos. 29-37.

20. The isolated or purified nucleic acid of claim 18, wherein the nucleic acid comprises Seq ID Nos. 29-38.

21. A kit comprising in combination for simultaneous or sequential use,
 (a) an isolated or purified binding partner comprising an antibody or one or more antibody fragments, wherein
  the binding partner binds to human TSH receptor;
  the binding partner inhibits TSH binding to the human TSH receptor; and
  the binding partner competes with hMAb TSHR1 (Seq ID Nos. 1-9) for binding to the TSH receptor, wherein the binding partner has an inhibitory activity with respect to $^{125}$I-labeled TSH binding to the TSH receptor of at least 15 units of International Standard NIBSC 90/672 per mg; and
 (b) an agent, different from the binding partner of (a), for stimulating TSH receptors.

22. The kit of claim 21, wherein the agent, different from the binding partner of (a), is recombinant human TSH.

* * * * *